United States Patent
Casorati et al.

(10) Patent No.: US 12,364,757 B2
(45) Date of Patent: Jul. 22, 2025

(54) TCR AND USES THEREOF

(71) Applicants: Ospedale San Raffaele S.r.l., Milan (IT); Fondazione Centro San Raffaele, Milan (IT)

(72) Inventors: Giulia Casorati, Milan (IT); Paolo Dellabona, Milan (IT); Claudia De Lalla, Milan (IT); Claudio Garavaglia, Milan (IT); Michela Consonni, Milan (IT)

(73) Assignees: OSPEDALE SAN RAFFAELE S.R.L, Milan (IT); FONDAZIONE CENTRO SAN RAFFAELE, Milan (IT)

(*) Notice: Subject to any disclaimer, the term of this patent is extended or adjusted under 35 U.S.C. 154(b) by 934 days.

(21) Appl. No.: 15/763,419

(22) PCT Filed: Oct. 3, 2016

(86) PCT No.: PCT/EP2016/073584
§ 371 (c)(1),
(2) Date: Mar. 26, 2018

(87) PCT Pub. No.: WO2017/055635
PCT Pub. Date: Apr. 6, 2017

(65) Prior Publication Data
US 2018/0305432 A1     Oct. 25, 2018

(30) Foreign Application Priority Data
Oct. 1, 2015   (EP) .................................. 15187993

(51) Int. Cl.
| | | |
|---|---|---|
| A61K 40/32 | (2025.01) | |
| A61K 40/11 | (2025.01) | |
| A61K 40/42 | (2025.01) | |
| A61K 40/50 | (2025.01) | |
| A61P 35/02 | (2006.01) | |
| C07K 14/725 | (2006.01) | |
| C12N 5/0783 | (2010.01) | |

(52) U.S. Cl.
CPC .............. *A61K 40/32* (2025.01); *A61K 40/11* (2025.01); *A61K 40/4224* (2025.01); *A61P 35/02* (2018.01); *C07K 14/7051* (2013.01); *C12N 5/0636* (2013.01); *A61K 40/50* (2025.01); *A61K 2239/48* (2023.05)

(58) Field of Classification Search
CPC .... A61K 40/32; A61K 40/11; A61K 40/4224; A61K 40/50; A61K 2239/48; A61P 35/02; C07K 14/7051; C12N 5/0636
USPC ................ 424/93.21, 93.71; 435/325, 320.1; 530/350
See application file for complete search history.

(56) References Cited

U.S. PATENT DOCUMENTS

| | | | | |
|---|---|---|---|---|
| 10,377,808 | B2* | 8/2019 | Blankenstein | ..... C07K 14/7051 |
| 2013/0274203 | A1* | 10/2013 | Morgan | .................. A61P 25/00 |
| | | | | 514/19.5 |

FOREIGN PATENT DOCUMENTS

| | | | |
|---|---|---|---|
| JP | 2015-62419 A | | 4/2015 |
| WO | WO 2008/028601 A2 | | 3/2008 |
| WO | WO 2012/038055 | * | 3/2012 |
| WO | WO 2013/039889 A1 | | 3/2013 |
| WO | WO 2015/009606 A1 | | 1/2015 |
| WO | WO 2015/077615 A1 | | 5/2015 |
| WO | WO 2015/113140 A1 | | 8/2015 |
| WO | WO 2015/181274 A1 | | 12/2015 |
| WO | WO 2016/070119 A1 | | 5/2016 |
| WO | WO 2017/055635 A1 | | 4/2017 |

OTHER PUBLICATIONS

Roy et al. (2014) PNAS Oct. 28, 2014 111 (43) E4648-E4657; first published Oct. 8, 2014; https://doi.org/10.1073/pnas.1408549111.*
Roy et al. (2014), PNAS, www.pnas.org/cgi/doi/10.1073/pnas.1408549111, e4648-e4657.*
Baker et al. (2012) Immunol. Rev., vol. 250, 10-31.*
Lepore et al. (Jun. 16, 2014) J. Exp. Med., vol. 211(7), 1363-1377.*
Low et al. (2012) PLoS ONE vol. 7(12):e51397. doi:10.1371/journal.pone.0051397, pp. 1-11.*
Laugel et al. (2005) Biol. Chem., vol. 280(3), 1882-1892.*
Saito H. et al. (1984) Nature 309:757-762.*
International Search Report for International Application No. PCT/EP2016/073584, mailed Dec. 8, 2016 in 3 pages.
Giulia Casorati (2018) Dichiarazione 1$^{st}$ Cuneo city Immunotherapy Conference (CCITC)—Immunotherapy in Hematological Malgnancies 2018.
Donermeyer et al. (2006) The study of high-affinity TCRs reveals duality in T cell recognition of antigen: specificity and degeneracy. The Journal of Immunology, 2006, 177:6911-6919.
Chinese Office Action for Application No. 201680070422.3 dated Nov. 13, 2020 with English Translation.

* cited by examiner

*Primary Examiner* — Anne Marie S Wehbe
(74) *Attorney, Agent, or Firm* — LUCAS & MERCANTI, LLP

(57) ABSTRACT

The present invention relates to a TCR or functional variant thereof having antigenic specificity for CD1c molecules associated with a self-lipid, preferably (mLPA) or derivative thereof, to relative polypeptide, protein, nucleic acid, recombinant expression vector, host cell, population of cells, antibody and pharmaceutical composition. The present invention also relates to the uses of said TCR and relative products, in particular for use in the treatment and/or prevention of an hematological disorder.

Figure 1:
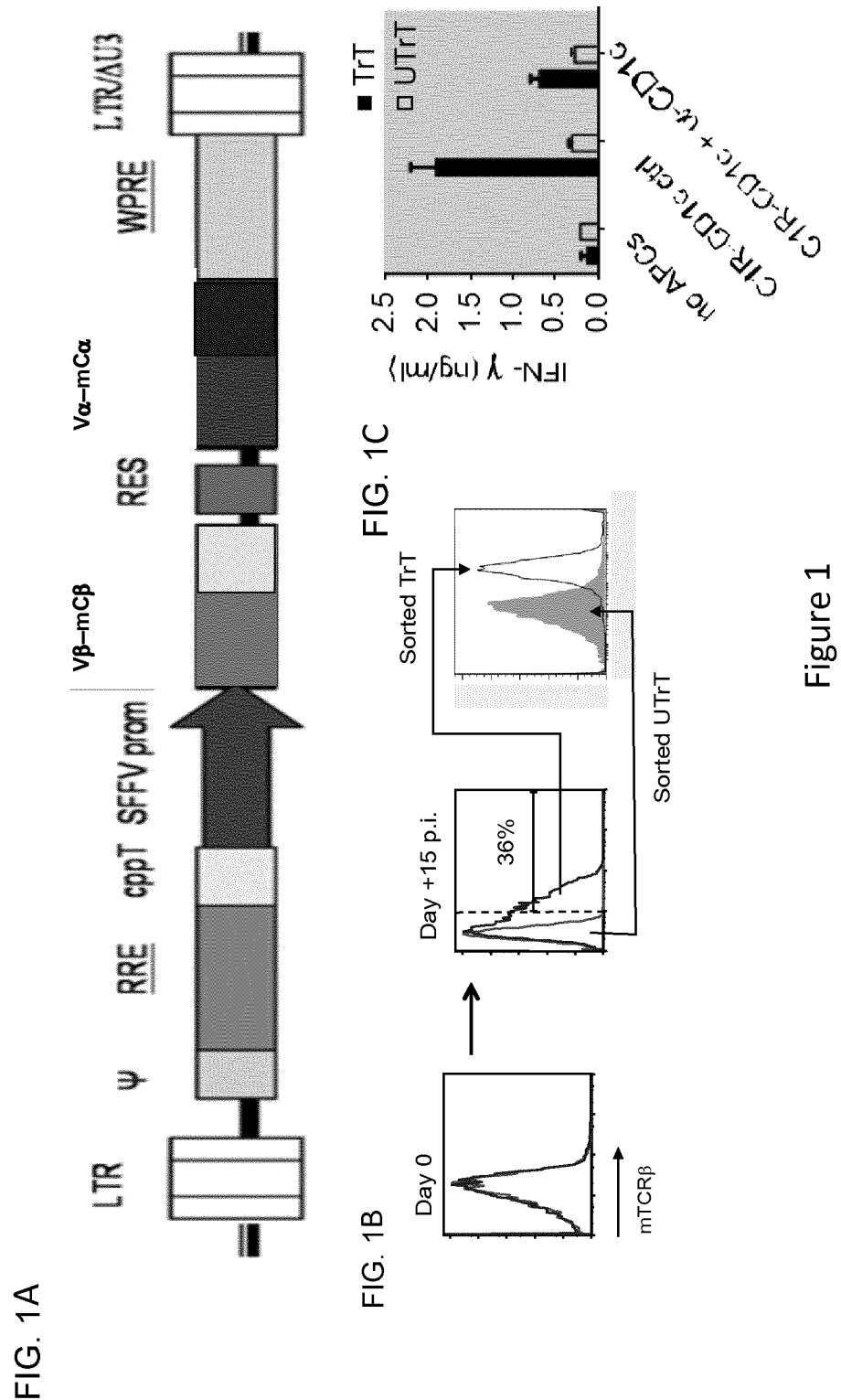

25 Claims, 15 Drawing Sheets
Specification includes a Sequence Listing.

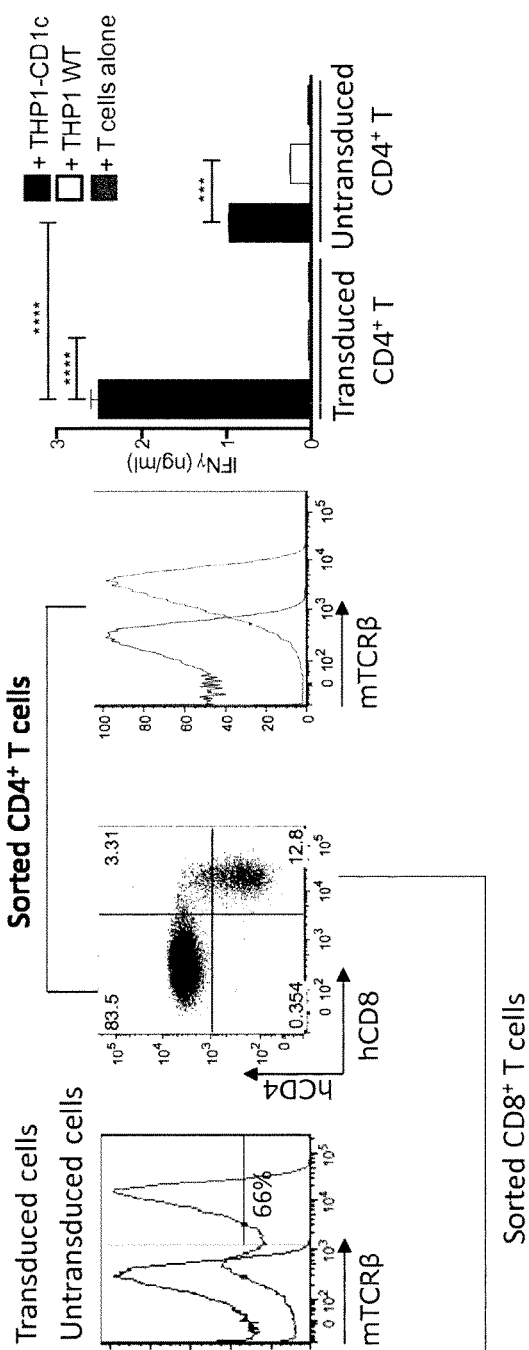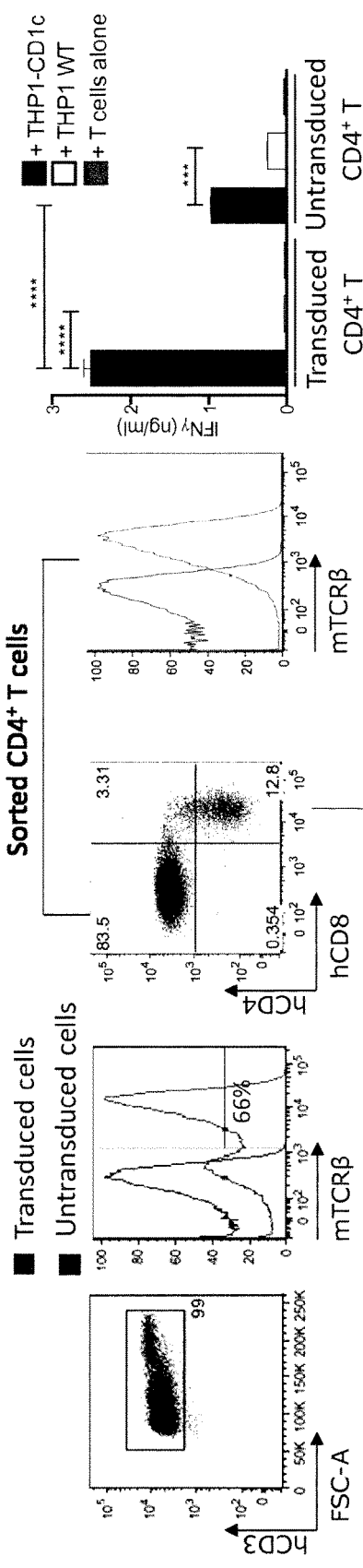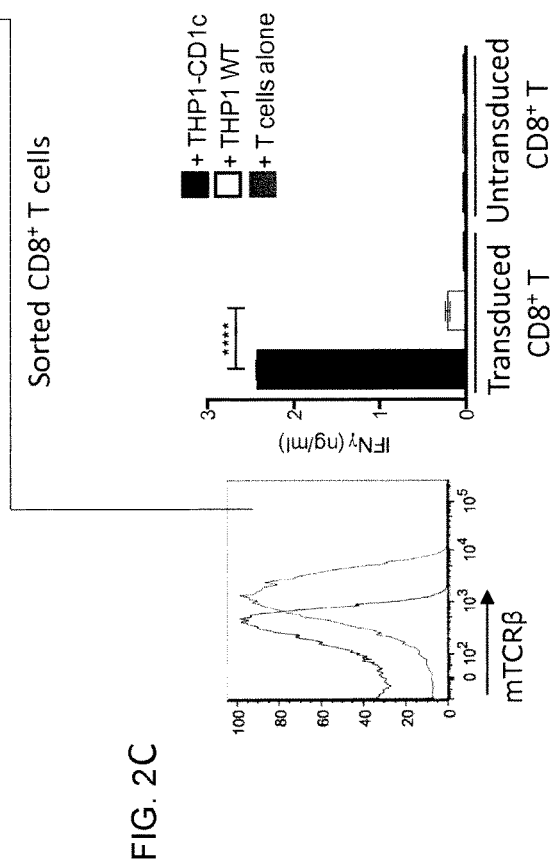
FIG. 2A
FIG. 2B
FIG. 2C
Figure 2

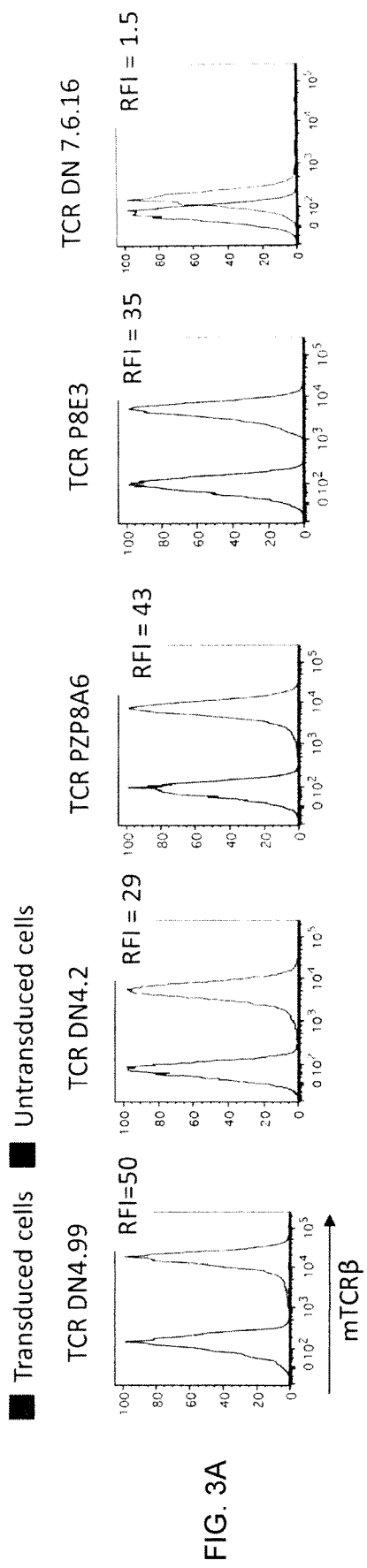
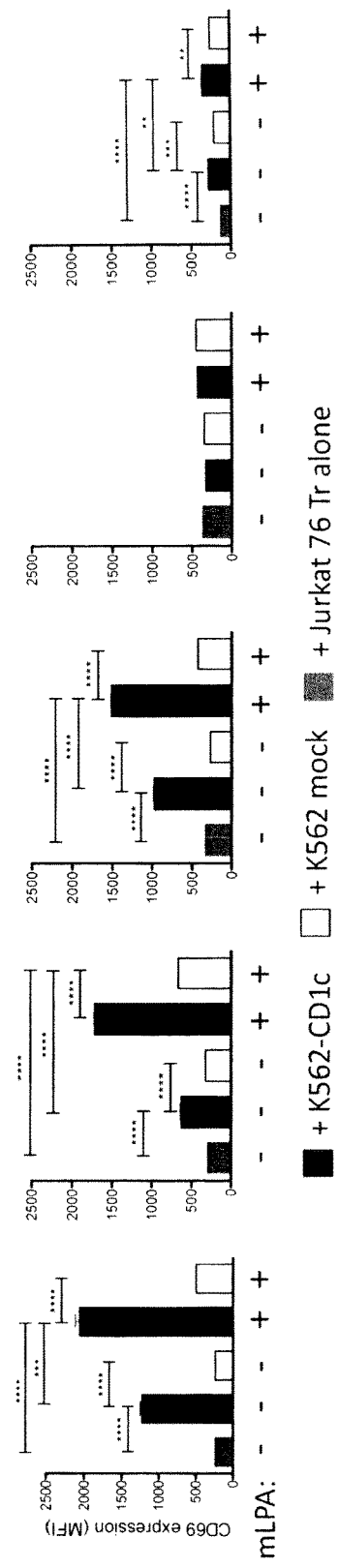
Figure 3

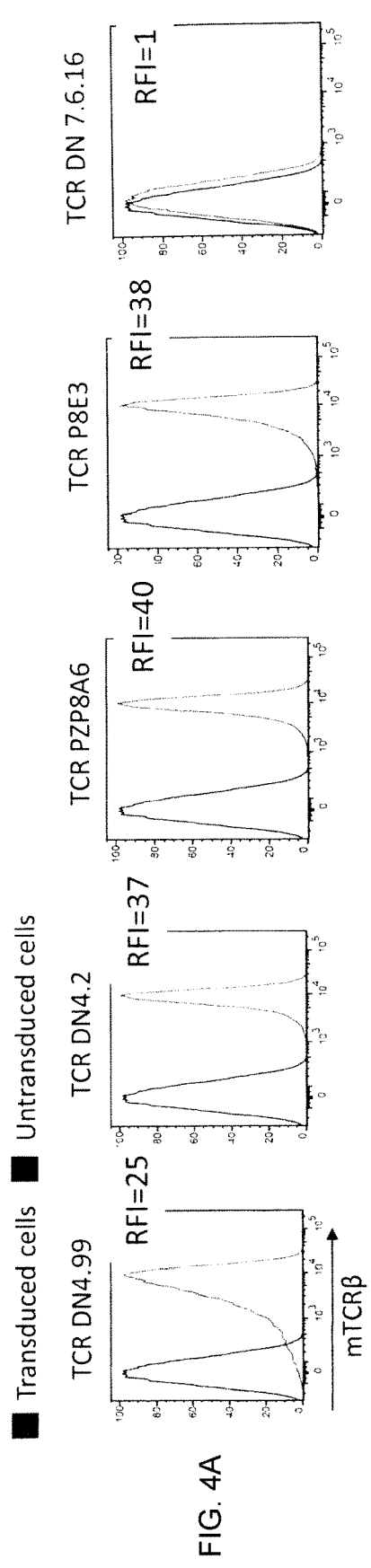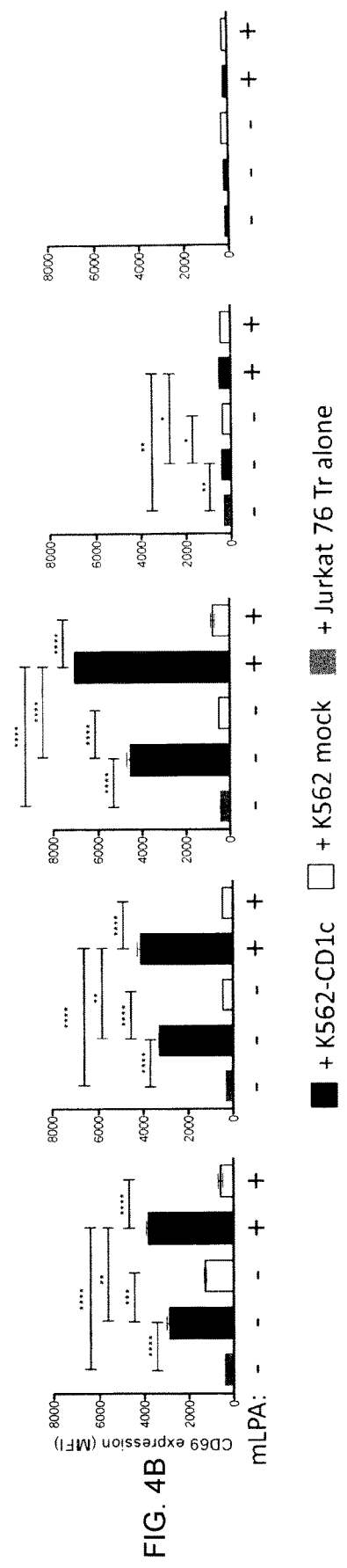
Figure 4

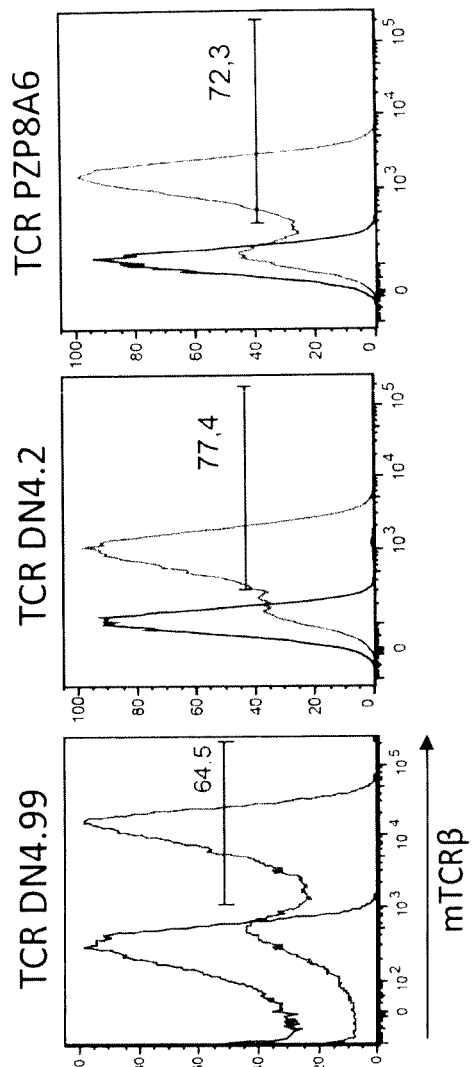
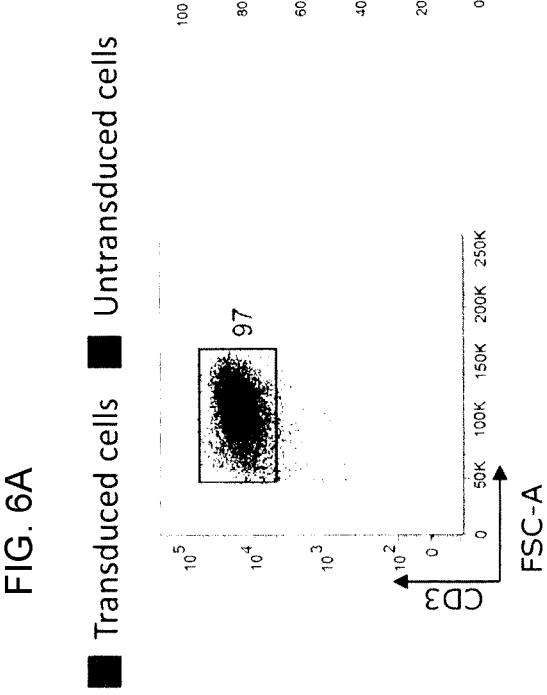
Figure 6

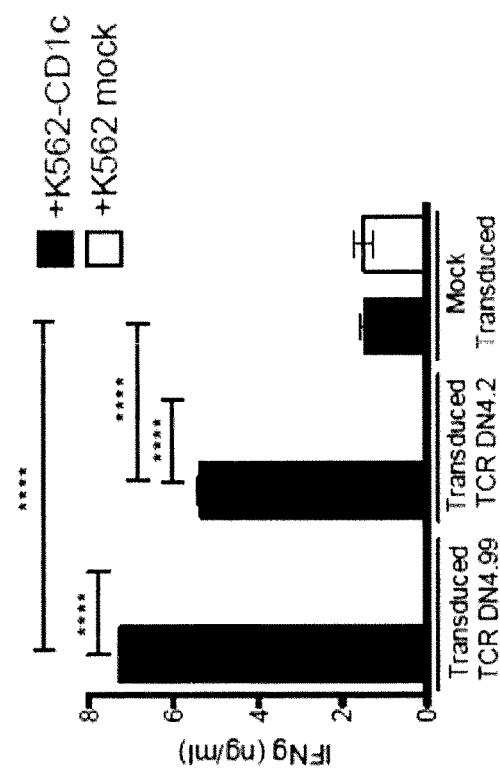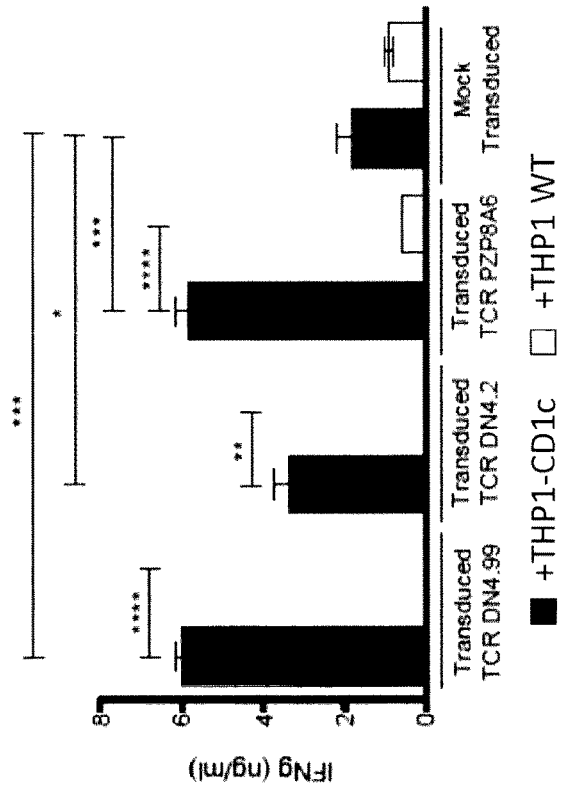
Figure 6

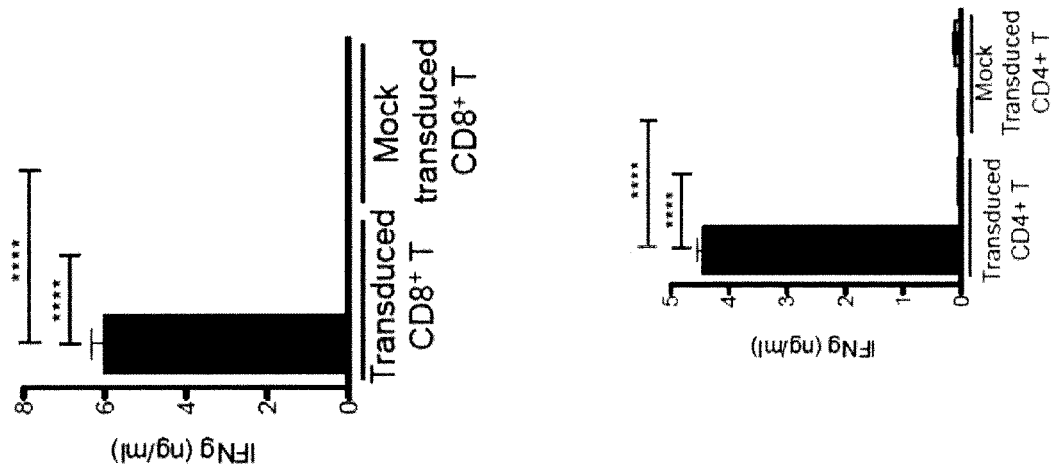
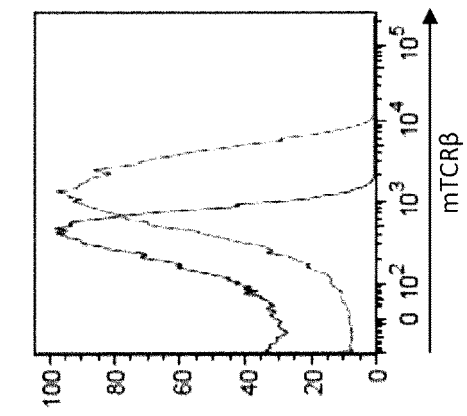
FIG. 7A - Sorted transduced CD8+ T cells
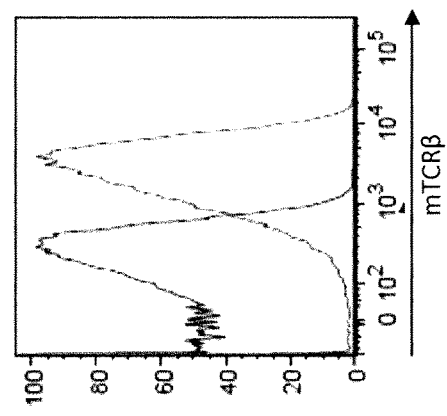
FIG. 7B - Sorted transduced CD4+ T cells
Figure 7 (1/2)

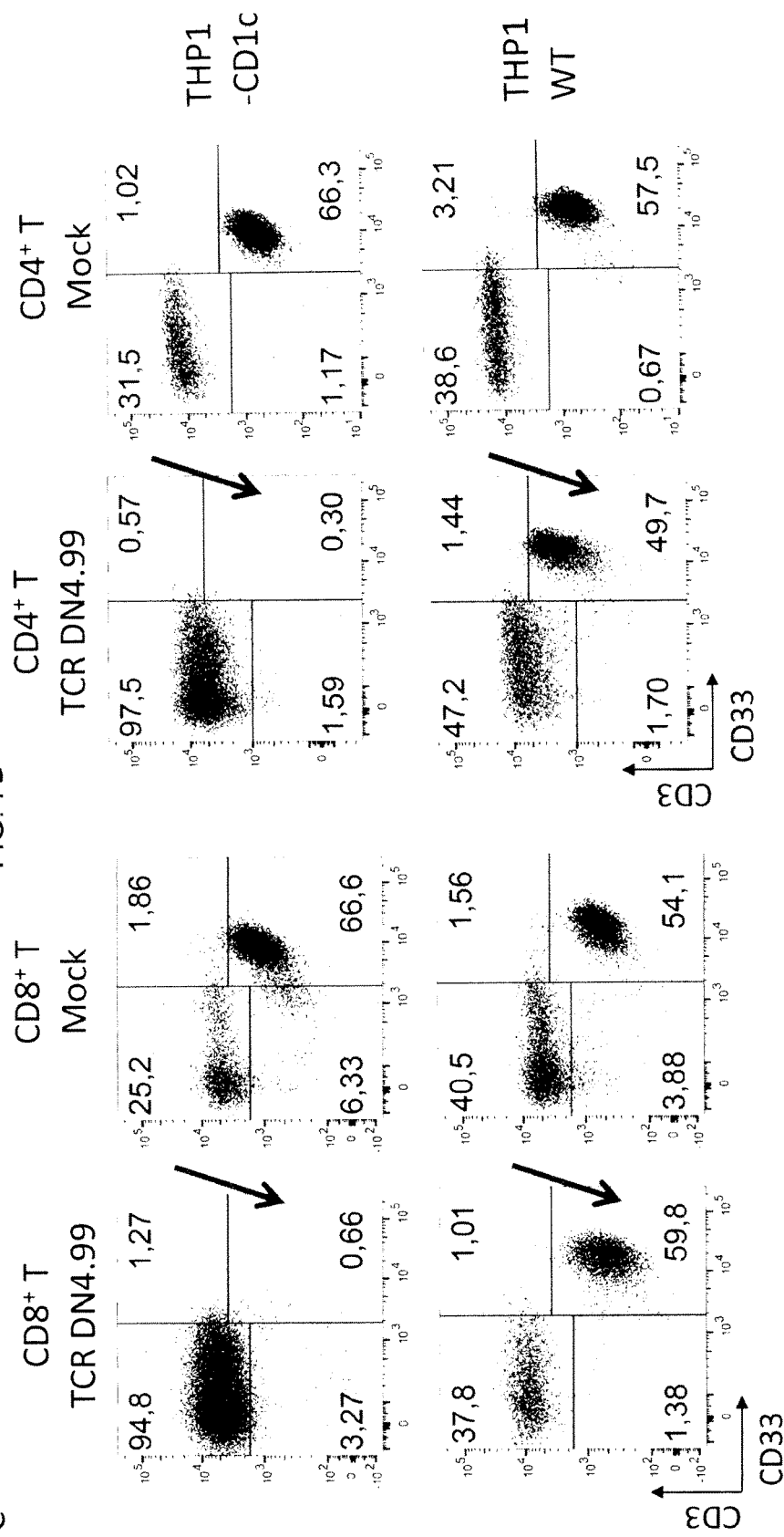
Figure 7 (2/2)

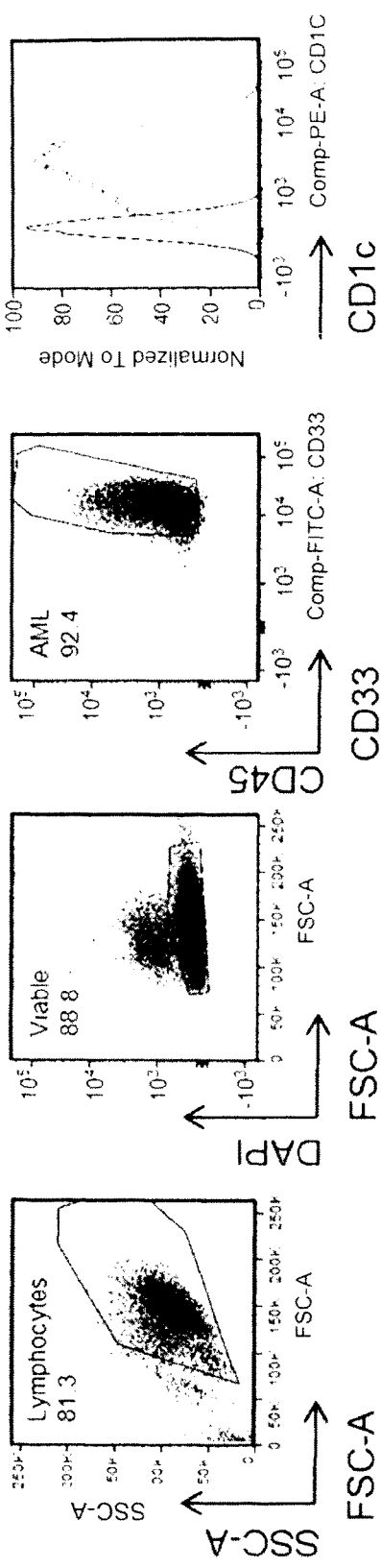
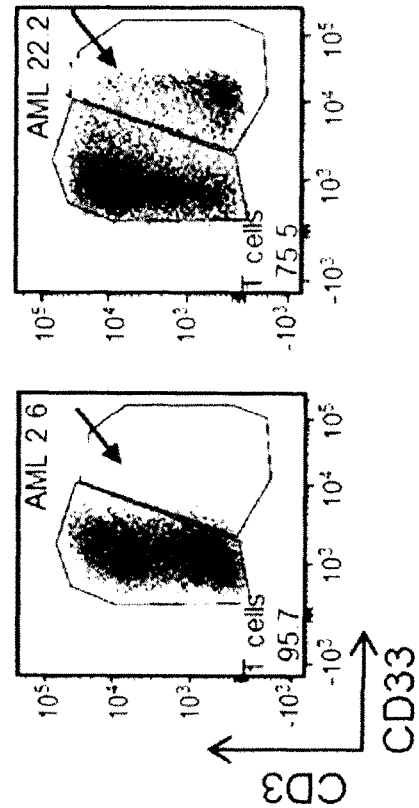
FIG. 8A
FIG. 8B
Figure 8

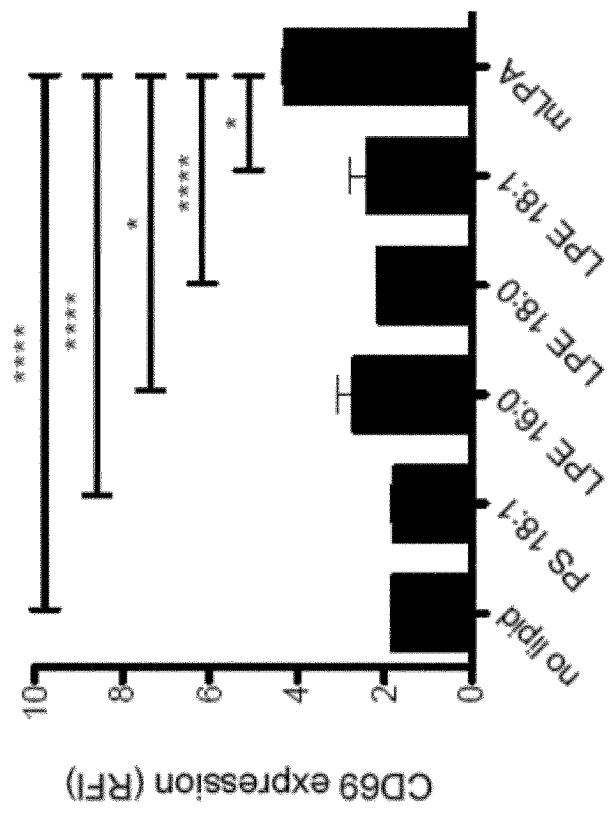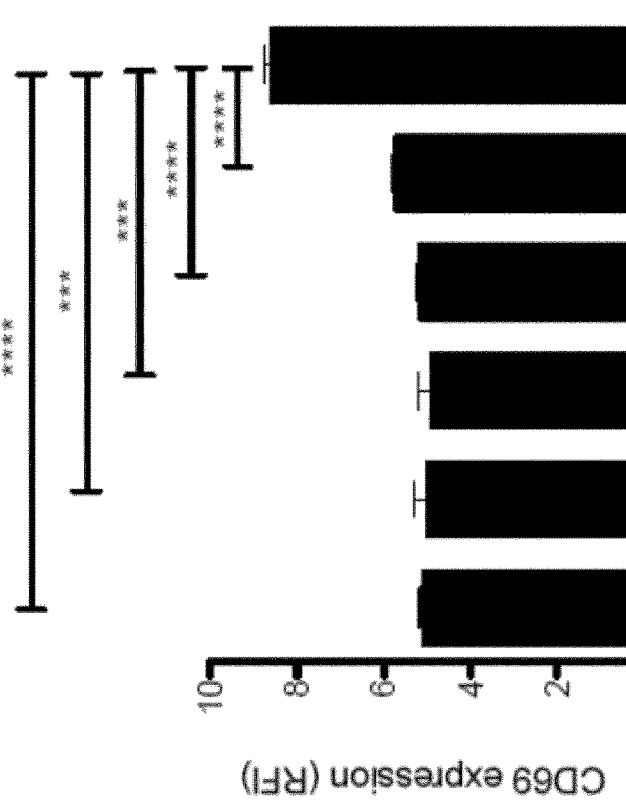
Figure 11

TCR AND USES THEREOF

TECHNICAL FIELD

The present invention relates to a TCR or functional variant thereof having antigenic specificity for CD1c molecules associated with a self-lipid, preferably (mLPA) or derivative thereof, to relative polypeptide, protein, nucleic acid, recombinant expression vector, host cell, population of cells, antibody and pharmaceutical composition. The present invention also relates to the uses of said TCR and relative products, in particular for use in the treatment and/or prevention of an hematological disorder.

BACKGROUND OF THE INVENTION

The immune system plays a critical role in controlling the growth of malignant cells by sensing antigenic differences generated during the oncogenic process. Tumor-specific T cells and antigens are actively exploited in cancer immunotherapy, a treatment that can attain therapeutic efficacy with minimal side effects. The discovery of T cells that recognize lipid antigens presented by CD1 molecules has opened new perspectives for basic and translational immunology. The four CD1a-d isotypes are non-polymorphic antigen-presenting molecules that follow distinct intracellular trafficking routes to survey the endocytic pathway and intersect diverse lipid Ags. CD1-restricted T cells are characterized by marked autoreactivity compared with MHC-restricted T cells and directly recognize CD1-expressing cells. The inventors have recently shown that CD1 self-reactive T cells account for a relevant fraction of the circulating T cell repertoire. They hypothesize that this CD1 "self-reactive" T cell response might participate in tumor immune surveillance, where self-antigens are targets of immune responses. The inventors have found that acute leukemia blasts express different CD1 isotypes and have isolated T cell clones capable of recognizing leukemia cells in a CD1-dependent manner, suggesting that lipid antigens of cancer origin could be the target of specific response. Furthermore, they have isolated and molecularly characterized a leukemia-derived lipid antigen recognized by self-reactive T cell clones restricted for CD1c, a CD1 isotype frequently expressed by acute myeloid leukemia (AML) and B-cell acute lymphoblastic leukemia (B-ALL). Harnessing CD1-restricted T cell responses to self-lipid antigens is an attractive option for adoptive immunotherapy of leukemia, because CD1 molecules are expressed essentially only on mature leukocytes, thus minimizing the risk of systemic GVHD. Moreover they are not polymorphic and therefore the same CD1 isotype would present the same lipid antigens in all individuals. This represents a further advantage considering adoptive immunotherapy strategies in the context of hematopoietic stem cell transplantation, which are successful in the treatment of hematological malignancies, because the same allogeneic CD1 self-reactive T cell could be utilized to treat leukemia in different patients.

The inventors have further shown that mLPA-specific T cells limit leukemia progression in vivo, in an immunodeficient mouse model, suggesting the possibility to harness these T cells for the adoptive immunotherapy of $CD1c^+$ acute leukemia. To generate large quantities of tumor-reactive T cells to use for adoptive immunotherapy approaches, it is possible to generate T lymphocytes expressing recombinant antigen specific T cell receptors (TCRs). TCRs occur in two forms, as either αβ heterodimer or γδ heterodimers.

These four chains display a characteristic structure consisting of an "immunoglobulin V region-like" (V) N-terminal domain connected to an "immunoglobulin C-region-like" (C) second domain. Each of these domains has a characteristic intradomain disulphide bridge. The V-region is formed by rearrangement of V-segments with J- or D-segments and is the part of the molecules that confers the antigen specificity to T cells. Also the CD1c-self reactive TCRs are formed by α and β chains each consisting of V regions, which together impart specificity for lipid antigens bound in CD1c molecules and C regions. It is possible to clone and transfer the TCR expressed by CD1c self-reactive T cell clones into polyclonal T cells to redirect them against leukemia cells.

Each TCR peptide contains variable complementarity determining regions (CDRs), as well as framework regions (FRs) and a constant region. The sequence diversity of αβ T cells is largely determined by the amino acid sequence of the third complementarity-determining region (CDR3) loops of the a and β chain variable domains, which diversity is a result of recombination between variable (Vb), diversity (Db), and joining (Jb) gene segments in the β chain locus, and between analogous Va and Ja gene segments in the a chain locus, respectively. The existence of multiple such gene segments in the TCR a and β chain loci allows for a large number of distinct CDR3 sequences to be encoded. CDR3 sequence diversity is further increased by independent addition and deletion of nucleotides at the Vb-Db, Db-Jb, and Va-Ja junctions during the process of TCR gene rearrangement. In this respect, immunocompetence is reflected in the diversity of TCRs.

SUMMARY OF THE INVENTION

The inventors found that CD1c self-reactive T-cells recognize a novel class of self-lipids, identified as methyl-lysophosphatidic acids, which are accumulated in leukemia cells. Primary acute myeloid and B-cell acute leukemia blasts express CD1 molecules. Methyl-lysophosphatidic acid-specific T-cells efficiently kill CD1c+ acute leukemia cells, poorly recognize non-transformed CD1c-expressing cells, and protect immune-deficient mice against CD1c+ human leukemia cells. The identification of immunogenic self-lipid antigens accumulated in leukemia cells and the observed leukemia control by lipid-specific T-cells in vivo provide a new conceptual framework for leukemia immune surveillance and possible immunotherapy.

In the present invention different CD1c self-reactive T cell clones have been isolated from healthy donors and leukemia patients that selectively recognize novel self-lipid tumor-associated antigens (TAA) that represent a potential target for novel immunotherapies. In particular the TAA is methyl lysophosphatidic acid (mLPA), C16-methyl-lysophosphatidic acid (C16-mLPA) or C18-methyl-lysophosphatidic acid (C18-mLPA), belonging to a novel class of lipids that can act as T cell-stimulatory antigens only when presented by CD1c+ cells. The TCRs have been cloned from five independent CD1c self-reactive T cell clones. The TCRs may be used for adoptive immunotherapy, for cell therapy, for the treatment of leukemia, for the prevention of leukemia relapse following hematopoietic stem cell transplantation (HSCT) (at present no therapy is available) and improvement of efficacy of HSCT.

Then the invention provides an isolated or purified T-cell receptor (TCR) comprising:
a complementary determining region (CDRa1) amino acid sequence having at least 80% identity to an amino acid sequence selected from the group consisting of: SEQ. ID NO: 25, 31, 37, 43 and 49 and;

a complementary determining region (CDRa2) amino acid sequence having at least 80% identity to an amino acid sequence selected from the group consisting of: SEQ. ID NO: 26, 32, 38, 44 and 50 and;

a complementary determining region (CDRa3) amino acid sequence having at least 80% identity to an amino acid sequence selected from the group consisting of: SEQ. ID NO: 27, 33, 39, 45 and 51 and;

a complementary determining region (CDRb1) amino acid sequence having at least 80% identity to an amino acid sequence selected from the group consisting of: SEQ. ID NO: 28, 34, 40, 46 and 52 and;

a complementary determining regions (CDRb2) amino acid sequence having at least 80% identity to an amino acid sequence selected from the group consisting of: SEQ. ID NO: 29, 35, 41, 47 and 53 and;

complementary determining regions (CDRb3) amino acid sequence having at least 80% identity to an amino acid sequence selected from the group consisting of: SEQ. ID NO: 30, 36, 42, 48 and 54.

Preferably the isolated or purified T-cell receptor (TCR) comprises:

amino acid sequence having at least 80% identity to SEQ ID NO: 25, and amino acid sequence having at least 80% identity to SEQ ID NO: 26 and amino acid sequence having at least 80% identity to SEQ ID NO: 27 or amino acid sequence having at least 80% identity to SEQ ID NO: 28, and amino acid sequence having at least 80% identity to SEQ ID NO: 29 and amino acid sequence having at least 80% identity to SEQ ID NO: 30 or amino acid sequence having at least 80% identity to SEQ ID NO: 31, and amino acid sequence having at least 80% identity to SEQ ID NO: 32 and amino acid sequence having at least 80% identity to SEQ ID NO: 33 or amino acid sequence having at least 80% identity to SEQ ID NO: 34, and amino acid sequence having at least 80% identity to SEQ ID NO: 35 and amino acid sequence having at least 80% identity to SEQ ID NO: 36 or amino acid sequence having at least 80% identity to SEQ ID NO: 37, and amino acid sequence having at least 80% identity to SEQ ID NO: 38 and amino acid sequence having at least 80% identity to SEQ ID NO: 39 or amino acid sequence having at least 80% identity to SEQ ID NO: 40, and amino acid sequence having at least 80% identity to SEQ ID NO: 41 and amino acid sequence having at least 80% identity to SEQ ID NO: 42 or amino acid sequence having at least 80% identity to SEQ ID NO: 43, and amino acid sequence having at least 80% identity to SEQ ID NO: 44 and amino acid sequence having at least 80% identity to SEQ ID NO: 45 or amino acid sequence having at least 80% identity to SEQ ID NO: 46, and amino acid sequence having at least 80% identity to SEQ ID NO: 47 and amino acid sequence having at least 80% identity to SEQ ID NO: 48 or amino acid sequence having at least 80% identity to SEQ ID NO: 49, and amino acid sequence having at least 80% identity to SEQ ID NO: 50 and amino acid sequence having at least 80% identity to SEQ ID NO: 51 or amino acid sequence having at least 80% identity to SEQ ID NO: 52, and amino acid sequence having at least 80% identity to SEQ ID NO: 53 and amino acid sequence having at least 80% identity to SEQ ID NO: 54.

Preferably the isolated or purified T-cell receptor (TCR) comprises:

an amino acid sequence having at least 80% identity to SEQ ID NO: 25, and an amino acid sequence having at least 80% identity to SEQ ID NO: 26 and an amino acid sequence having at least 80% identity to SEQ ID NO: 27 and an amino acid sequence having at least 80% identity to SEQ ID NO: 28, and an amino acid sequence having at least 80% identity to SEQ ID NO: 29 and an amino acid sequence having at least 80% identity to SEQ ID NO: 30 or an amino acid sequence having at least 80% identity to SEQ ID NO: 31, and an amino acid sequence having at least 80% identity to SEQ ID NO: 32 and an amino acid sequence having at least 80% identity to SEQ ID NO: 33 and an amino acid sequence having at least 80% identity to SEQ ID NO: 34, and an amino acid sequence having at least 80% identity to SEQ ID NO: 35 and an amino acid sequence having at least 80% identity to SEQ ID NO: 36 or an amino acid sequence having at least 80% identity to SEQ ID NO: 37, and an amino acid sequence having at least 80% identity to SEQ ID NO: 38 and an amino acid sequence having at least 80% identity to SEQ ID NO: 39 and an amino acid sequence having at least 80% identity to SEQ ID NO: 40, and an amino acid sequence having at least 80% identity to SEQ ID NO: 41 and an amino acid sequence having at least 80% identity to SEQ ID NO: 42 or an amino acid sequence having at least 80% identity to SEQ ID NO: 43, and an amino acid sequence having at least 80% identity to SEQ ID NO: 44 and an amino acid sequence having at least 80% identity to SEQ ID NO: 45 and an amino acid sequence having at least 80% identity to SEQ ID NO: 46, and an amino acid sequence having at least 80% identity to SEQ ID NO: 47 and an amino acid sequence having at least 80% identity to SEQ ID NO: 48 or an amino acid sequence having at least 80% identity to SEQ ID NO: 49, and an amino acid sequence having at least 80% identity to SEQ ID NO: 50 and an amino acid sequence having at least 80% identity to SEQ ID NO: 51 and an amino acid sequence having at least 80% identity to SEQ ID NO: 52, and an amino acid sequence having at least 80% identity to SEQ ID NO: 53 and an amino acid sequence having at least 80% identity to SEQ ID NO: 54.

Preferably the isolated or purified T-cell receptor (TCR) comprises:

SEQ ID NO: 25, and SEQ ID NO: 26 and SEQ ID NO: 27 and SEQ ID NO: 28, and SEQ ID NO: 29 and SEQ ID NO: 30 or SEQ ID NO: 31, and SEQ ID NO: 32 and SEQ ID NO: 33 and SEQ ID NO: 34, and SEQ ID NO: 35 and SEQ ID NO: 36 or SEQ ID NO: 37, and SEQ ID NO: 38 and SEQ ID NO: 39 and SEQ ID NO: 40, and SEQ ID NO: 41 and SEQ ID NO: 42 or SEQ ID NO: 43, and SEQ ID NO: 44 and SEQ ID NO: 45 and SEQ ID NO: 46, and SEQ ID NO: 47 and SEQ ID NO: 48 or SEQ ID NO: 49, and SEQ ID NO: 50 and SEQ ID NO: 51 and SEQ ID NO: 52, and SEQ ID NO: 53 and SEQ ID NO: 54.

Still preferably the isolated or purified TCR comprises (a) an amino acid sequence having at least 80% identity to a sequence selected from the group consisting of SEQ ID NOs: 1, 3, 5, 7 or 9 and (b) an amino acid sequence having at least 80% identity to selected from the group consisting of SEQ ID Nos: 2, 4, 6, 8 or 10.

Still preferably the isolated or purified TCR or functional variant comprises an amino acid sequence having at least 80% identity to SEQ ID No. 1 and an amino acid sequence having at least 80% identity to SEQ ID No. 2 or an amino acid sequence having at least 80% identity to SEQ ID No. 3 and an amino acid sequence having at least 80% identity to SEQ ID No. 4 or an amino acid sequence having at least 80% identity to SEQ ID No. 5 and an amino acid sequence having at least 80% identity to SEQ ID No. 6 or an amino acid sequence having at least 80% identity to SEQ ID No. 7 and an amino acid sequence having at least 80% identity to SEQ ID No. 8 or an amino acid sequence having at least 80% identity to SEQ ID No. 9 and an amino acid sequence having at least 80% identity to SEQ ID No. 10.

Preferably it comprises:
SEQ ID NO: 1, and SEQ ID NO: 2 or
SEQ ID NO: 3, and SEQ ID NO: 4 or
SEQ ID NO: 3, and SEQ ID NO: 6 or
SEQ ID NO: 7, and SEQ ID NO: 8 or
SEQ ID NO: 9, and SEQ ID NO: 10.

Yet preferably the isolated or purified TCR comprises a murine, a human or a humanized amino acid sequence of a constant region. This means that any of the above indicated sequence may be humanized. The TCR of the invention may comprise both murine and human sequences, only human sequences or only murine sequences or a combination of human or mouse sequence with humanize sequences.

Preferably the isolated or purified TCR comprises an amino acid sequence having at least 80% identity to SEQ ID No. 11 or an amino acid sequence having at least 80% identity to SEQ ID No. 12, preferably it comprises an amino acid sequence having at least 80% identity to SEQ ID No. 13 or an amino acid sequence having at least 80% identity to SEQ ID No. 14.

Preferably the isolated or purified TCR is in a multimeric form. Preferably it has specificity for CD1c molecule associated with a self-lipid. Preferably the self-lipid is a methyl-lysophosphatidic acid or derivative thereof. Preferably the methyl-lysophosphatidic acid is selected from the group consisting of: methyl-lysophosphatidic acid (mLPA), C16-methyl-lysophosphatidic acid (C16-mLPA) or C18-methyl-lysophosphatidic acid (C18-mLPA) or a derivative thereof.

The invention also provides an isolated or purified nucleic acid comprising a nucleotide sequence encoding the TCR as defined above. Preferably the nucleotide sequence is codon-optimized. Still preferably the nucleotide sequence comprises a) a nucleotide sequence having at least 80% identity to a sequence selected from the group consisting of SEQ ID NOs: 15, 17, 19, 21 or 23 and b) a nucleotide sequence having at least 80% identity to a sequence selected from the group consisting of SEQ ID NOs: 16, 18, 20, 22, or 24.

The invention also provides a recombinant expression vector comprising the nucleic acid of the invention as defined above.

The invention also provides an isolated host cell comprising the recombinant expression vector of the invention, preferably the host cell is a T cell, preferably it is a mammal T cell, preferably an human T cell.

The invention also provides a pharmaceutical composition comprising the TCR, the nucleic acid, the recombinant expression vector, the host cell as defined above and a pharmaceutically acceptable carrier.

Preferably the composition further comprises methyl lysophosphatidic acid (mLPA).

The invention also provides the isolated or purified T-cell receptor (TCR), the nucleic acid, the recombinant expression vector, the host cell or the pharmaceutical composition of the invention as defined above, for use in the treatment and/or prevention of an hematological disorder.

Preferably the hematological disorder is characterized by blood and bone marrow accumulation of immature and abnormal cells derived from hematopoietic precursors.

Preferably the hematological disorder is acute leukemia, preferably primary acute myeloid leukemia or B-cell acute leukemia.

Preferably the isolated or purified T-cell receptor (TCR), the nucleic acid, the recombinant expression vector, the host cell or the pharmaceutical composition for use as defined above further comprises the administration of an agent or a therapeutic treatment, preferably the agent is methyl lysophosphatidic acid (mLPA) or preferably the therapeutic treatment is hematopoietic stem cell transplantation (HSCT) or a chemotherapeutic treatment, preferably the chemotherapeutic treatment is selected from the group consisting of: asparaginase, busulfan, carboplatin, cisplatin, daunorubicin, doxorubicin, fluorouracil, gemcitabine, hydroxyurea, methotrexate, paclitaxel, rituximab, vinblastine, vincristine, azacytidine.

The invention also provides the isolated or purified T-cell receptor (TCR), the nucleic acid, the recombinant expression vector, the host cell or the pharmaceutical composition as defined above, for use in a method to prevent an hematological disorder relapse following hematopoietic stem cell transplantation (HSCT). Preferably the method also comprises the administration of mLPA.

The invention also provides the isolated or purified T-cell receptor (TCR) as defined above for use in a method for the diagnosis of an hematological disorder, preferably the hematological disorder is characterized by blood and bone marrow accumulation of immature and abnormal cells derived from hematopoietic precursors, preferably the hematological disorder is acute leukemia, preferably primary acute myeloid leukemia or B-cell acute leukemia.

Preferably the method comprises adding methyl lysophosphatidic acid (mLPA).

Preferably the TCR is in a soluble and/or multimeric form.

The invention also provides a method for the production of a host cell as defined above comprising the step of transducing said host cell with the TCR as defined above or the nucleic acid as defined above or the vector as defined above.

Preferably the method further comprises expanding said host cell, preferably in the presence of methyl lysophosphatidic acid (mLPA), for instance with anti-CD3 and anti-CD28 beads in the presence of human recombinant cytokines such as IL-2 and/or IL-7 and/or IL-15.

The present invention also concerns functional variants of the TCR as defined above.

The invention further provides related polypeptides and proteins, as well as related nucleic acids, recombinant expression vectors, host cells, and populations of cells. Further provided by the invention are antibodies, or antigen binding portions thereof, and pharmaceutical compositions relating to the TCRs (including functional portions and functional variants thereof) of the invention.

Methods of detecting a leukemia cell and methods of treating or preventing an hematological disorder in a mammal are further provided by the invention. The inventive method of detecting a leukemia cell comprises (i) contacting a sample comprising leukemia cells with any of the inventive TCRs (including functional portions and functional variants thereof), polypeptides, proteins, nucleic acids, recombinant expression vectors, host cells, populations of host cells, or antibodies, or antigen binding portions thereof, described herein, thereby forming a complex, and (ii) detecting the complex, wherein detection of the complex is indicative of the presence of a leukemia cell.

The inventive method of treating or preventing an hematological disorder in a mammal comprises administering to the mammal any of the TCRs (including functional portions and functional variants thereof), polypeptides, or proteins described herein, any nucleic acid or recombinant expression vector comprising a nucleotide sequence encoding any of the TCRs (including functional portions and functional variants thereof), polypeptides, proteins described herein, or any host cell or population of host cells comprising a recombinant vector which encodes any of the TCRs (including functional portions and functional variants thereof), polypeptides, or proteins described herein, in an amount effective to treat or prevent the hematological disorder in the mammal.

The invention provides an isolated or purified T cell receptor (TCR), and functional portions and functional variants thereof, having antigenic specificity for mLPA associated with CD1c molecules.

In an embodiment of the invention, the isolated or purified TCR has antigenic specificity for mLPA. mLPA is a lipid tumour-associated antigen (TAA), that can act as T cell-stimulatory antigen only when presented by CD1c+ cells.

TCR in a soluble form is a TCR molecule where the transmembrane and intracellular sequences of the constant regions are eliminated to permit the secretion of the monomer.

The TCR may be recombinant.

A TCR is in a multimeric form when multiple numbers of soluble TCR monomeric molecules, preferably recombinant are bound via their truncated constant regions to a defined matrix (such as avidin or streptavidin, proteoglycans, nanoparticles) and are free to bind to their targets (mLPA bound to CD1c) via the antigen-binding variable segments.

The TCRs (including functional portions and functional variants thereof) of the invention provide many advantages, including when used for adoptive cell transfer or therapy. For example, by targeting mLPA that is presented in the context of CD1c+ cells, the inventive TCRs (including functional portions and functional variants thereof) make it possible to treat patients bearing CD1c+ leukemia cells recognised by inventive TCRs. CD1c is frequently expressed by AML and B-ALL. Accordingly, the inventive TCRs (including functional portions and functional variants thereof) advantageously greatly expand the patient population that can be treated. Additionally, without being bound by a particular theory, it is believed that because mLPA is expressed by specific cells, the inventive TCRs (including functional portions and functional variants thereof) advantageously provide the ability to destroy specifically such cells and, accordingly, treat or prevent leukemia. Additionally, without being bound to a particular theory, it is believed that because CD1c expression is absent from parenchimatous organs and/or because mLPA are leukemia antigens that are expressed mainly in tumor cells, the inventive TCRs (including functional portions and functional variants thereof) advantageously target the destruction of cancer cells while minimizing or eliminating the destruction of normal, non-cancerous cells, thereby reducing, for example, by minimizing or eliminating, toxicity and minimizing graft vs. host disease (GVHD).

The phrase "antigenic specificity" as used herein means that the TCR can specifically bind to and immunologically recognize mLPA in combination with CD1c with high avidity. For example, a TCR may be considered to have "antigenic specificity" for mLPA if T cells expressing the TCR express defined membrane markers, such as CD69, HLA-DR, CD137 when cultured with leukemia cells that express CD1c and contain natural mLPA, or with mammalian cells that express CD1c and are loaded with synthetic mLPA. Alternatively or additionally, a TCR may be considered to have "antigenic specificity" for mLPA if T cells expressing the TCR produce cytokines, such as IL-2, IFNγ, IL-4 when cultured with leukemia cells that express CD1c and contain natural mLPA, or with mammalian cells that express CD1c and are loaded with synthetic mLPA. Alternatively or additionally, a TCR may be considered to have "antigenic specificity" for mLPA if T cells expressing the TCR kill leukemia cells that express CD1c and contain natural mLPA, or mammalian cells that express CD1c and are loaded with synthetic mLPA.

The inventive TCRs (including functional portions and functional variants thereof) are able to recognize mLPA in a human CD1c+ restricted manner. "CD1c+ restricted manner," as used herein, means that the TCR elicits an immune response upon binding to a mLPA within the context of a CD1c+ target cell.

The invention provides a TCR comprising two polypeptides (i.e., polypeptide chains), such as an alpha (α or a) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for mLPA in the context of CD1c restricted T cell.

In an embodiment of the invention, the TCR comprises two polypeptide chains, each of which comprises a variable region comprising a complementarity determining region (CDR) CDR1, a CDR2, and a CDR3 of a TCR. In an embodiment of the invention, the TCR comprises a first polypeptide chain comprising a CDR1 (CDR1 of α chain), a CDR2 (CDR2 of α chain) and a CDR3 (CDR3 of α chain) CDR sequences are underlined in the TCRa sequences below, and a second polypeptide chain comprising a CDR1 (CDR1 of β chain), a CDR2 (CDR2 of β chain), and a CDR3 (CDR3 of β chain). CDR sequences are underlined in the TCRb sequences below. In this regard, the inventive TCR can comprise any one or more of the amino acid sequences selected from the group consisting of any one or more of SEQ ID NOs: 3 to 10.

Alternatively or additionally, the TCR can comprise an amino acid sequence of a variable region of a TCR comprising the CDRs set forth above.

Alternatively or additionally, the TCR can comprise an α chain of a TCR and a β chain of a TCR. Each of the α chain and β chain of the inventive TCR can independently comprise any amino acid sequence. Preferably, the a chain comprises the variable region of an α chain as set forth above. An α chain of this type can be paired with any β chain of a TCR. Preferably, the β chain of the inventive TCR comprises the variable region of a β chain as set forth above.

Included in the scope of the invention are functional variants of the inventive TCRs described herein. The term "functional variant" as used herein refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to mLPA for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 95%, 96%, 97%, 98%, 99% or more identical in amino acid sequence to the parent TCR, polypeptide, or protein.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, He, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gin, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

Like the TCRs of the invention, the functional variants described herein comprise two polypeptide chains, each of which comprises a variable region comprising a CDR1, a CDR2, and a CDR3 of a TCR. Preferred sequences of CDRs are underlined in the sequences reported below. The preferred CDRs may comprise such sequences or a functional fragment thereof. In this regard, the inventive functional variant of a TCR can comprise the amino acid sequences selected from the group consisting of SEQ ID NOs: 1 to 10. Alternatively or additionally, the functional variant of a TCR can comprise a substituted amino acid sequence of a variable region of a TCR comprising the CDRs set forth below.

Alternatively or additionally, the functional variant of a TCR can comprise a substituted α chain of a TCR and a β chain of a TCR. Each of the α chain and β chain of the inventive TCR can independently comprise any amino acid sequence. Preferably, the substituted α chain comprises a substituted variable region of an α chain as set forth above. An inventive substituted α chain of this type can be paired with any β chain of a TCR. Preferably, the β chain of the inventive TCR comprises the variable region of a β chain as set forth below.

In an embodiment of the invention, the TCR (or functional variant thereof) may comprise a human constant region. In this regard, the TCR (or functional variant thereof) can comprise a human constant region comprising SEQ ID NO: 13 (human constant region of an α chain), SEQ ID NO: 14 (human constant region of β chain), both SEQ ID NOs: 13 and 14. Preferably, the TCR (or functional variant thereof) comprises both SEQ ID NOs: 13 and 14.

In another embodiment of the invention, the TCR (or functional variant thereof) can comprise a human/mouse chimeric TCR (or functional variant thereof). In this regard, the TCR (or functional variant thereof) can comprise a mouse constant region comprising SEQ ID NO: 11 (mouse constant region of an α chain), SEQ ID NO: 12 (mouse constant region of β chain), or both SEQ ID NOs: 11 and 12. Preferably, the TCR (or functional variant thereof) comprises both SEQ ID NOs: 11 and 12.

The inventive human/mouse chimeric TCR (or functional variant or functional portion thereof) can comprise any of the CDRs set forth above. In this regard, the inventive human/mouse chimeric TCR (or functional variant or functional portion thereof) can comprise the amino acid sequences selected from the group consisting of SEQ ID NOs: 11; SEQ ID NOs: 12; SEQ ID NOs: 13; SEQ ID NOs: 14.

Alternatively or additionally, the human/mouse chimeric TCR (or functional variant or functional portion thereof) can comprise any of the variable regions set forth above. In this regard, the inventive human/mouse chimeric TCR (or functional variant or functional portion thereof) can comprise the substituted amino acid sequence of the substituted variable region of an α chain, the variable region of a β chain, the substituted amino acid sequence of the substituted variable region of a β chain, the variable region of an α chain. Alternatively or additionally, the human/mouse chimeric TCR (or functional variant or functional portion thereof) can comprise an α chain of a TCR (or functional variant or functional portion thereof) and a β chain of a TCR (or functional variant or functional portion thereof). Each of the α chain and β chain of the inventive human/mouse chimeric TCR (or functional variant or functional portion thereof) can independently comprise any amino acid sequence. Preferably, the α chain comprises the variable region of an α chain as set forth above. In this regard, the inventive human/mouse chimeric TCR (or functional variant or functional portion thereof) can comprise the amino acid sequence of reported below. An inventive human/mouse chimeric TCR (or functional variant or functional portion thereof) of this type can be paired with any β chain of a TCR (or functional variant or functional portion thereof). Preferably, the β chain of the inventive human/mouse chimeric TCR (or functional variant or functional portion thereof) comprises the variable region of a β chain as set forth above. In this regard, the inventive human/mouse chimeric TCR (or functional variant or functional portion thereof) can comprise the amino acid sequence as reported below. The inventive human/mouse chimeric TCR (or functional variant or functional portion thereof), therefore, can comprise the amino acid sequence of SEQ ID NO: 1 to 10 or a combination thereof.

Also provided by the invention is a polypeptide comprising a functional portion of any of the TCRs or functional variants described herein. The term "polypeptide" as used herein includes oligopeptides and refers to a single chain of amino acids connected by one or more peptide bonds.

With respect to the inventive polypeptides, the functional portion can be any portion comprising contiguous amino acids of the TCR (or functional variant thereof) of which it is a part, provided that the functional portion specifically binds to mLPA associated with CD1c. The term "functional portion" when used in reference to a TCR (or functional variant thereof) refers to any part or fragment of the TCR (or functional variant thereof) of the invention, which part or fragment retains the biological activity of the TCR (or functional variant thereof) of which it is a part (the parent TCR or parent functional variant thereof). Functional portions encompass, for example, those parts of a TCR (or functional variant thereof) that retain the ability to specifically bind to mLPA (e.g., in an CD1c restricted manner) or detect, treat, or prevent hematological disorder, to a similar extent, the same extent, or to a higher extent, as the parent TCR (or functional variant thereof). In reference to the parent TCR (or functional variant thereof), the functional portion can comprise, for instance, about 10%, 25%, 30%, 50%, 68%, 80%, 90%, 95%, or more, of the parent TCR (or functional variant thereof). The functional portion can comprise additional amino acids at the amino or carboxy terminus of the portion, or at both termini, which additional amino acids are not found in the amino acid sequence of the parent TCR or functional variant thereof. Desirably, the additional amino acids do not interfere with the biological function of the functional portion, e.g., specifically binding to mLPA in association with CD1c; and/or having the ability to detect hematological disorder, treat or prevent an hematological disorder, etc. More desirably, the additional amino acids enhance the biological activity, as compared to the biological activity of the parent TCR or functional variant thereof.

The polypeptide can comprise a functional portion of either or both of the α and β chains of the TCRs or functional variant thereof of the invention, such as a functional portion comprising one or more of CDR1, CDR2, and CDR3 of the variable region(s) of the α chain and/or β chain of a TCR or functional variant thereof of the invention. In this regard, the polypeptide can comprise a functional portion comprising the amino acid sequence of CDR1 of α chain, CDR2 of α chain, CDR3 of α chain, CDR1 of β chain, CDR2 of β chain and CDR3 of β chain, or a combination thereof. Alternatively or additionally, the inventive polypeptide can comprise, for instance, the variable region of the inventive TCR or functional variant thereof comprising a combination of the CDR regions set forth above.

Alternatively or additionally, the inventive polypeptide can comprise the entire length of an α or β chain of one of the TCRs or functional variant thereof described herein. In this regard, the inventive polypeptide can comprise an amino acid sequence of SEQ ID NOs: 1 to 10. Alternatively, the polypeptide of the invention can comprise α and β chains of the TCRs or functional variants thereof described herein.

The invention further provides a protein comprising at least one of the polypeptides described herein. By "protein" is meant a molecule comprising one or more polypeptide chains.

In an embodiment, the protein of the invention can comprise a first polypeptide chain comprising the amino acid sequences of SEQ ID NOs: 1, 3, 5, 7, 9 and a second polypeptide chain comprising the amino acid sequence of SEQ ID NOs: 2, 4, 6, 8, 10. The protein of the invention can, for example, comprise a first polypeptide chain comprising the amino acid sequence of SEQ ID NO: 1 and a second polypeptide chain comprising the amino acid sequence of SEQ ID NO: 2. In this instance, the protein of the invention can be a TCR. Alternatively, if, for example, the protein comprises a single polypeptide chain comprising SEQ ID NO: 1 and SEQ ID NO: 2 or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, TCR constant gamma, TCR constant delta, CD3, CD28, CD137, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. See, for instance, Choi et al., Mol. Biotechnol. 31: 193-202 (2005).

In some embodiments of the invention, the TCRs (and functional portions and functional variants thereof), polypeptides, and proteins of the invention may be expressed as a single protein comprising a linker peptide linking the α chain and the β chain. In this regard, the TCRs (and functional variants and functional portions thereof), polypeptides, and proteins of the invention comprising SEQ ID NO: 1 to 10 may further comprise a linker peptide. The linker peptide may advantageously facilitate the expression of a recombinant TCR (including functional portions and functional variants thereof), polypeptide, and/or protein in a host cell. Upon expression of the construct including the linker peptide by a host cell, the linker peptide may be cleaved, resulting in separated α and β chains.

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab) 2' fragment of an antibody, etc. The polypeptide chain of an antibody, or portion thereof, can exist as a separate polypeptide of the recombinant antibody.

Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

The TCR (or functional variant thereof), polypeptide, or protein can consist essentially of the specified amino acid sequence or sequences described herein, such that other components of the TCR (or functional variant thereof), polypeptide, or protein, e.g., other amino acids, do not materially change the biological activity of the TCR (or functional variant thereof), polypeptide, or protein. In this regard, the inventive TCR (or functional variant thereof), polypeptide, or protein can, for example, consist essentially of the amino acid sequence of SEQ ID NO: 1 to 10.

The TCRs, polypeptides, and proteins of the invention (including functional variants thereof) can be of any length, i.e., can comprise any number of amino acids, provided that the TCRs, polypeptides, or proteins (or functional variants thereof) retain their biological activity, e.g., the ability to specifically bind to mLPA-enriched CD1c-expressing cells; detect hematological disorder in a mammal; or treat or prevent cancer in a mammal, etc. For example, the polypeptide can be in the range of from about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention (including functional variants thereof) of the invention can comprise synthetic amino acids in place of one or more naturally-occurring amino acids. Such synthetic amino acids are known in the art, and include, for example, aminocyclohexane carboxylic acid, norleucine, a-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, ocaminocyclopentane carboxylic acid, a-aminocyclohexane carboxylic acid, a-aminocycloheptane carboxylic acid, a-(2-amino-2-norbornane)-carboxylic acid, α,γ-diaminobutyric acid, α,β-diaminopropionic acid, homophenylalanine, and -tert-butylglycine.

The TCRs, polypeptides, and proteins of the invention (including functional variants thereof) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention (including functional variants thereof) can be obtained by methods known in the art. Suitable methods of de novo synthesizing polypeptides and proteins are described in references, such as Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3$^{rd}$ ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Further, some of the TCRs, polypeptides, and proteins of the invention (including functional variants thereof) can be isolated and/or purified from a source, such as a plant, a bacterium, an insect, a mammal, e.g., a rat, a human, etc. Methods of isolation and purification are well-known in the art. Alternatively, the TCRs, polypeptides, and/or proteins described herein (including functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs (including functional variants thereof), polypeptides, and proteins can be synthetic, recombinant, isolated, and/or purified.

Included in the scope of the invention are conjugates, e.g., bioconjugates, comprising any of the inventive TCRs, polypeptides, or proteins (including any of the functional variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., Methods Mol. Biol. 298: 209-223 (2005) and Kirin et al, Inorg Chem. 44(15): 5405-5415 (2005)).

"nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N <6>-isopentenyladenine, 1-methylguanine, 1-methylinosine, 2,2-dimethylguanine, 2-methyladenine, 2-methylguanine, 3-methylcytosine, 5-methylcytosine, N<6>-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6- isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the TCRs, polypeptides, proteins, or functional variants thereof described herein. For example, the nucleic acid can comprise, consist, or consist essentially of any one or more of the nucleotide sequence SEQ ID NOs: 15 to 24 or a combination thereof.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs (including functional portions and functional variants thereof). It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91% o, about 92%, about 93%, about 94%, about 95%, about 96%, about 97%, about 98%, or about 99% identical to any of the nucleic acids described herein.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, Lajolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λΘTIO, λσII, ZapII (Stratagene), EMBL4, and λNMI 149, also can be used. Examples of plant expression vectors include pBIOl, pBI101.2, pBI101.3, pBI121 and pBΓN19 (Clontech). Examples of animal expression vectors include pEUK-Cl, pMAM and pMAMneo (Clontech). Preferably, the recombinant expression vector is a viral vector, e.g., a retroviral or a lentiviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like. Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or normative promoter operably linked to the nucleotide sequence encoding the TCR, polypeptide, or protein (including functional variants thereof), or to the nucleotide sequence which is complementary to or which hybridizes to the nucleotide sequence encoding the TCR, polypeptide, or protein (including functional variants thereof). The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. Cancer Research UK Centre for Cancer Therapeutics at the Institute of Cancer Research, Sutton, Surrey, UK, Humana Press, 2004) and include, for example, the Herpes Simplex Virus (HSV) thymidine kinase (TK) gene, cytosine daminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a E. coli cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5oc cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, CD4+CD8+ double positive T cells, CD4+ helper T cells, e.g., Th1 and Th 2cells, CD8+ T cells (e.g., cytotoxic T cells), CD3+ T cells, Natural Killer T (NKT) cells, tumor infiltrating lymphocytes (TILs), memory T cells (e.g., central memory T cells and effector memory T cells), naive T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The invention further provides an antibody, or antigen binding portion thereof, which specifically binds to a functional portion of any of the TCRs (or functional variant thereof) described herein. Preferably, the functional portion specifically binds to the cancer antigen, e.g., the functional portion comprising the amino acid sequence of CDR1 of α chain, of CDR2 of α chain, of CDR3 of α chain, of CDR1 of β chain, of CDR2 of β chain, of CDR3 of β chain, of variable region of α chain, of variable region of β chain or a combination thereof, e.g., In a preferred embodiment, the antibody, or antigen binding portion thereof, binds to an epitope which is formed by all 6 CDRs (CDR1-3 of the alpha chain and CDR1-3 of the beta chain). The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive TCR (or functional variant thereof). Desirably, the antibody is specific for the functional portion of the inventive TCR (or functional variants thereof), such that there is minimal cross-reaction with other peptides or proteins.

Methods of testing antibodies for the ability to bind to any functional portion or functional variant of the inventive TCR are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Kohler and Milstein, Eur. J. Immunol., 5, 511-519 (1976), Harlow and Lane (eds.), Antibodies: A Laboratory Manual, CSH Press (1988), and C. A. Janeway et al. (eds.), Immunobiology, 5th Ed., Garland Publishing, New York, NY (2001)). Alternatively, other methods, such as EBV-hybridoma methods (Haskard and Archer, J. Immunol. Methods, 74(2), 361-67 (1984), and Roder et al., Methods Enzymol., 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1.

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, 3$^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al, supra. Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in, for example, U.S. Pat. No. 5,639,641 and Pedersen et al., J. Mol. Biol., 235, 959-973 (1994). [0088] The invention also provides antigen binding portions of any of the antibodies described herein. The antigen binding portion can be any portion that has at least one antigen binding site, such as Fab, F(ab') 2, dsFv, sFv, diabodies, and triabodies. A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., Protein Engineering, 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive TCRs, polypeptides, proteins, (including functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70%, 80%, 90%, 95%, or can be 100%.

The inventive TCRs, polypeptides, proteins (including functional variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, functional portions, functional variants, nucleic acids, expression vectors, host cells (including populations thereof), and antibodies (including antigen binding portions thereof), and a pharmaceutically acceptable carrier. The inventive pharmaceutical compositions containing any of the inventive TCR materials can comprise more than one inventive TCR material, e.g., a polypeptide and a nucleic acid, or two or more different TCRs (including functional portions and functional variants thereof). Alternatively, the pharmaceutical composition can comprise an inventive TCR material in combination with another pharmaceutically active agents or drugs, such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for oral, aerosol, parenteral, subcutaneous, intravenous, intramuscular, intraarterial, intrathecal, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell expressing the inventive TCR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumin. In an embodiment of the invention, the pharmaceutical composition may further comprise another therapeutic agent such as a chemotherapeutic agent.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a hematological antigen, or detect, treat or prevent hematological disorder in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ or IL-6 is secreted by T cells expressing the inventive TCR (or functional variant or functional portion thereof), polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ or IL-6 is secreted upon administration of a certain dose can be assayed by methods known in the art. The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the condition being treated. In an embodiment in which the inventive TCR material is a population of cells, the number of cells administered per infusion may vary, e.g., from about $1\times10^6$ to about $1\times10^{11}$ cells or more.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a targeting moiety. The practice of conjugating compounds, e.g., inventive TCR materials, to targeting moieties is known in the art. See, for instance, Wadwa et al, J. Drug Targeting 3: 111 (1995) and U.S. Pat. No. 5,087,616. The term "targeting moiety" as used herein, refers to any molecule or agent that specifically recognizes and binds to a cell-surface receptor, such that the targeting moiety directs the delivery of the inventive TCR materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B– cell receptor (BCR), CD28, Platelet-derived Growth Factor Receptor (PDGF), nicotinic acetylcholine receptor (nAChR), etc.). The term "bridge" as used herein, refers to any agent or molecule that links the inventive TCR materials to the targeting moiety. One of ordinary skill in the art recognizes that sites on the inventive TCR materials, which are not necessary for the function of the inventive TCR materials, are ideal sites for attaching a bridge and/or a targeting moiety, provided that the bridge and/or targeting moiety, once attached to the inventive TCR materials, do(es) not interfere with the function of the inventive TCR materials, i.e., the ability to bind to mLPA; or to detect, treat or prevent a hematological disorder.

It is contemplated that the inventive pharmaceutical compositions, TCRs (including functional variants thereof), polypeptides, proteins, nucleic acids, recombinant expression vectors, host cells, or populations of cells can be used in methods of treating or preventing a hematological disorder. Without being bound to a particular theory, the inventive TCRs (and functional variants thereof) are believed to bind specifically to mLPA, such that the TCR (or related inventive polypeptide or protein and functional variants thereof) when expressed by a cell is able to mediate an immune response against a target cell expressing mLPA. In this regard, the invention provides a method of treating or preventing a hematological disorder in a mammal, comprising administering to the mammal any of the pharmaceutical compositions, TCRs (and functional variants thereof), polypeptides, or proteins described herein, any nucleic acid or recombinant expression vector comprising a nucleotide sequence encoding any of the TCRs (and functional variants thereof), polypeptides, proteins described herein, or any host cell or population of cells comprising a recombinant vector which encodes any of the TCRs (and functional variants thereof), polypeptides, or proteins described herein, in an amount effective to treat or prevent an hematological disorder in the mammal.

In an embodiment of the invention, the inventive methods of treating or preventing hematological disorder may further comprise co-administering MHC Class I restricted TCRs, or polypeptides, proteins, nucleic acids, or recombinant expression vectors encoding MHC Class I restricted TCRs, or host cells or populations of cells expressing MHC Class I restricted TCRs, to the mammal.

In an embodiment of the invention, the inventive methods of treating or preventing hematological disorder may further comprise co-administering CD d restricted invariant NKT cell TCRs, or polypeptides, proteins, nucleic acids, or recombinant expression vectors encoding CD1d restricted invariant NKT cell TCRs, or host cells or populations of cells expressing CD1d restricted invariant NKT cell TCRs, to the mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal.

Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof. Also provided is a method of detecting the presence of an hematological disorder in a mammal. The method comprises (i) contacting a sample comprising cells of the hematological disorder with any of the inventive TCRs (and functional variants thereof), polypeptides, proteins, nucleic acids, recombinant expression vectors, host cells, populations of cells, or antibodies, or antigen binding portions thereof, described herein, thereby forming a complex, and detecting the complex, wherein detection of the complex is indicative of the presence of the hematological disorder in the mammal.

With respect to the inventive method of detecting hematological disorder in a mammal, the sample of cells of the cancer can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro. Also, detection of the complex can occur through any number of ways known in the art. For instance, the inventive TCRs (and functional variants thereof), polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The present invention will be illustrated by means of non limiting examples in reference to the following figures.

FIG. 1. Peripheral blood-derived T cells transduced with the CD1c self-reactive TCR DN 4.99 are efficiently retargeted against the CD1c-expressing acute leukemia cell line THP1. FIG. 1A Map of the bi-cistronic lentivirus vector pHR-SINEGFP carrying the chimeric TCR V-(D)-J segments from the mLPA-specific T cell clone DN4.99, fused with the mouse TCR Cα or Cβ cDNAs. Both chains are expressed from the internal Spleen Focus Forming Virus (SSFV) promoter.

FIG. 1B Generation of mLPA-specific T cell lines in vitro upon transduction of polyclonal T cells with the lentivirus described in (A). TCR expression by transduced (TrT, blue line) and untransduced (UTrT, red line) T cells at day 0 and day 15, and after sorting. TCR expression was detected using mouse Cβ-specific (mTCRβ) mAbs. Data are representative of three experiments.

FIG. 1C Recognition C1R-CD1c LCL by T cells transduced with the DN4.99 TCR (TrT) but not by untransduced ones (UTrT). T cells were cultured without (no APCs) or with C1R-CD1c cells in the presence (α-CD1c) or absence (ctrl) of anti-CD1c blocking mAbs. Bars indicate mean±s.d. of IFN-γ production of triplicates.

Figures 2, 2D:
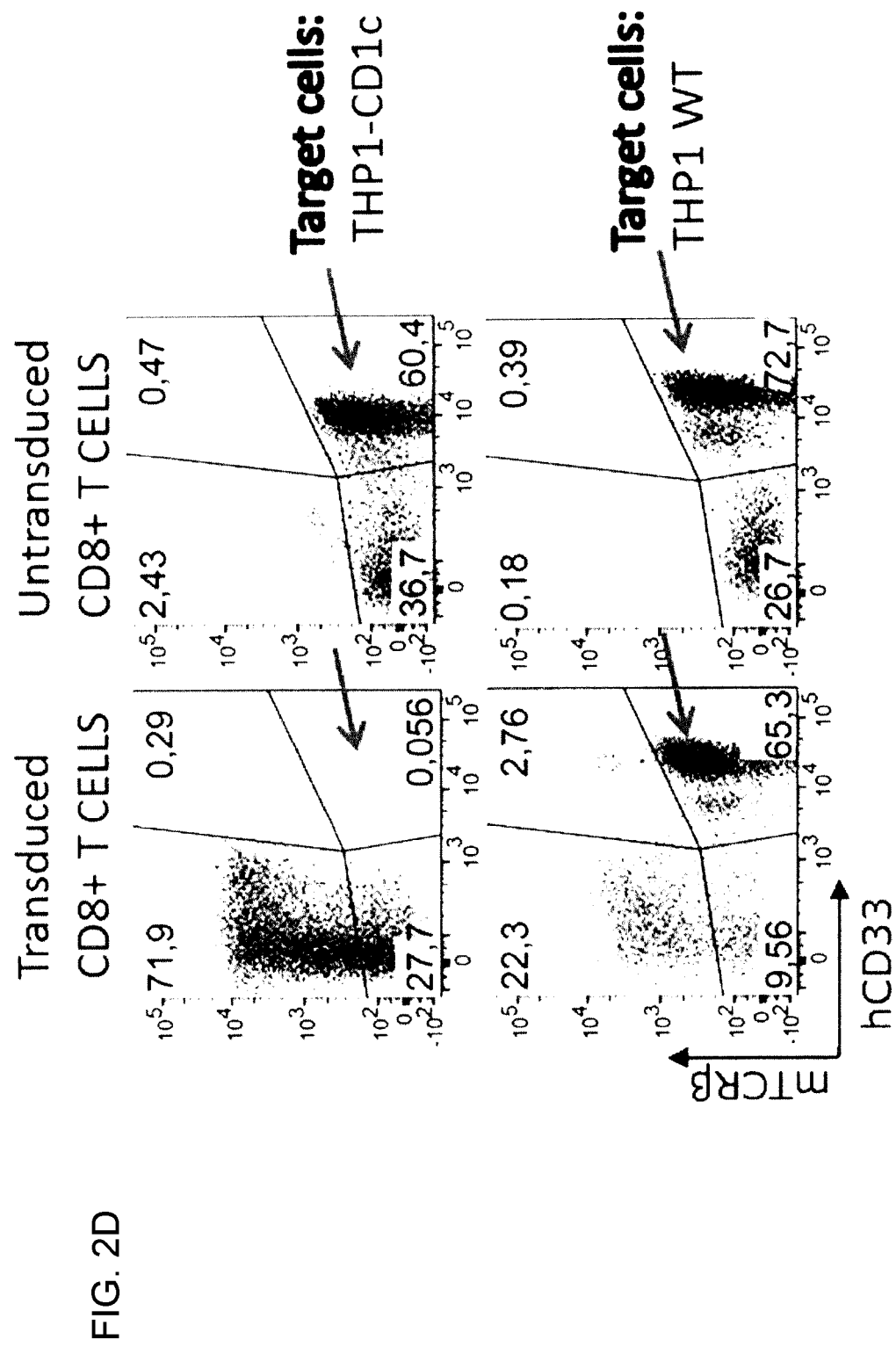

FIG. 2. CD4 and CD8 Peripheral blood-derived T cells transduced with the CD1c self-reactive TCR DN 4.99 efficiently recognize CD1c-expressing acute leukemia cell line THP1. T cells were activated in vitro with anti-CD3/CD28 beads plus IL-2 and IL-7 and transduced with a lentivirus encoding the chimeric humanV-mouseC TCR DN 4.99. FIG. 2A. The transduced T cells expressing or not-expressing the chimeric TCR (mTCRbeta) were sorted based on the expression of CD4 or CD8 co-receptor. FIG. 2B. The sorted CD4+ T cells were assayed for the recognition of CD1c+ or WT THP1 cells, as determined by the specific release of IFNg by ELISA after 12 h of co-culture. FIG. 2C. The sorted CD8+ T cells were assayed for the recognition of CD1c+ or negative (WT) THP1 cells, as determined by the specific release of IFNg by ELISA after 12 h of co-culture. FIG. 2D. The sorted CD8+ T cells were tested for specific killing of CD1c+ or WT THP1 cells in a 72 h co-culture assay. Arrows indicate quadrants containing THP1 cells, detected by the expression of CD33. CD1c+ THP1 cells, but not WT THP1 ones, disappear only in the co-culture with TCR-transduced CD8+ T cells, indicating specific killing by T cells transduced with the CD1c self-reactive TCR.

FIG. 3. Jurkat 76 cells transduced with CD1c self-reactive TCRs recognize K562-CD1c AML cell line. FIG. 3A expression of the chimeric CD1c self-reactive TCRs on transduced and untransduced Jurkat 76 determined by flow cytometry with anti m TCR mAb FIG. 3B Assessing the reactivity of Jurkat 76 cells transduced with the CD1c self-reactive TCRs. Transduced Jurkat 76 cells were plated in 96 U bottomwells containing 4×105 CD1c$^+$ K562-CD1c cells, loaded or not with mLPA (black bars) at 2.5:1 Effector T cell: leukemia Target cell (E:T=effector T cell: Target cell (ie leukemioa cell) ratio. K562 WT cells were used as negative control (white bars). After ON in vitro culture CD69 expression on Jurkat 76 cells was measured by flow citometry.

FIG. 4. Jurkat 76 β2m$^-$ cells transduced with CD1c self-reactive TCRs recognize K562-CD1c AML cell line. FIG. 4A expression of the chimeric CD1c self-reactive TCRs on transduced and untransduced Jurkat 76 β2m$^-$ determined by flow cytometry with anti-mTCRβ mAb. FIG. 4B Assessing the reactivity of Jurkat 76 cells transduced with the CD1c self-reactive TCRs. Transduced Jurkat 76 cells were plated in 96 u bottom-wells containing 4×105 CD1c$^+$ K562-CD1c cells loaded or not with mLPA (black bars) at E:T=2.5:1 ratio. K562 WT cells were used as negative control (white bars). After ON culture CD69 expression on Jurkat 76 cells was measured by flow citometry.

Figure 5:
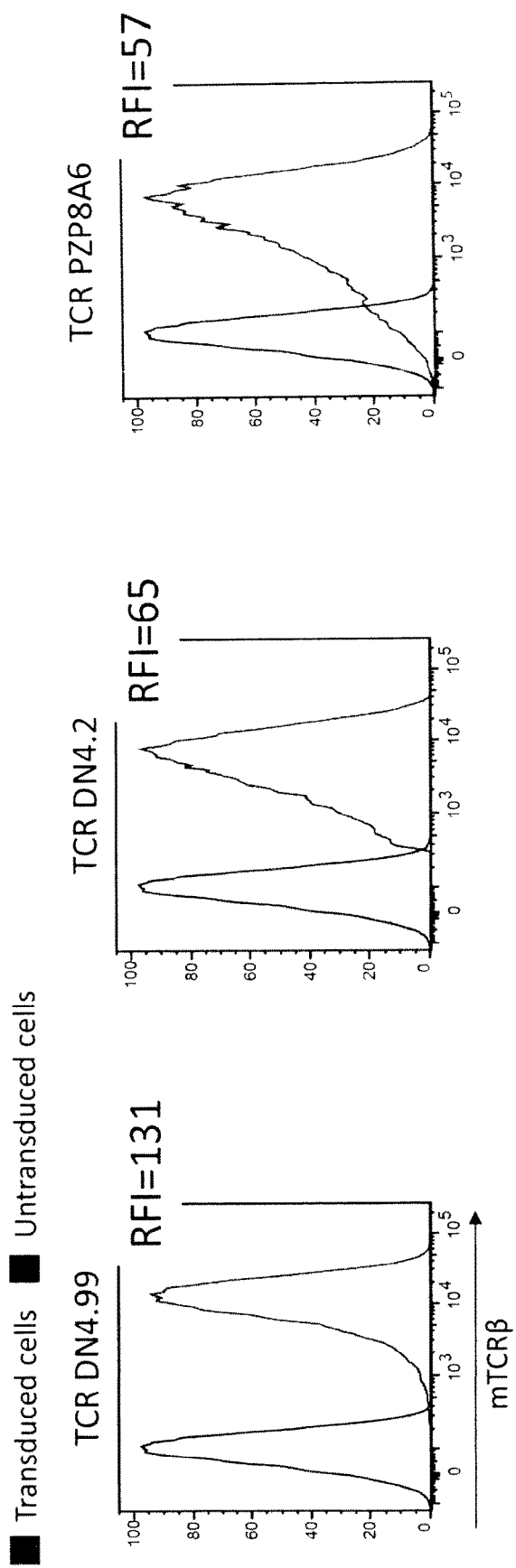
Figure 5:
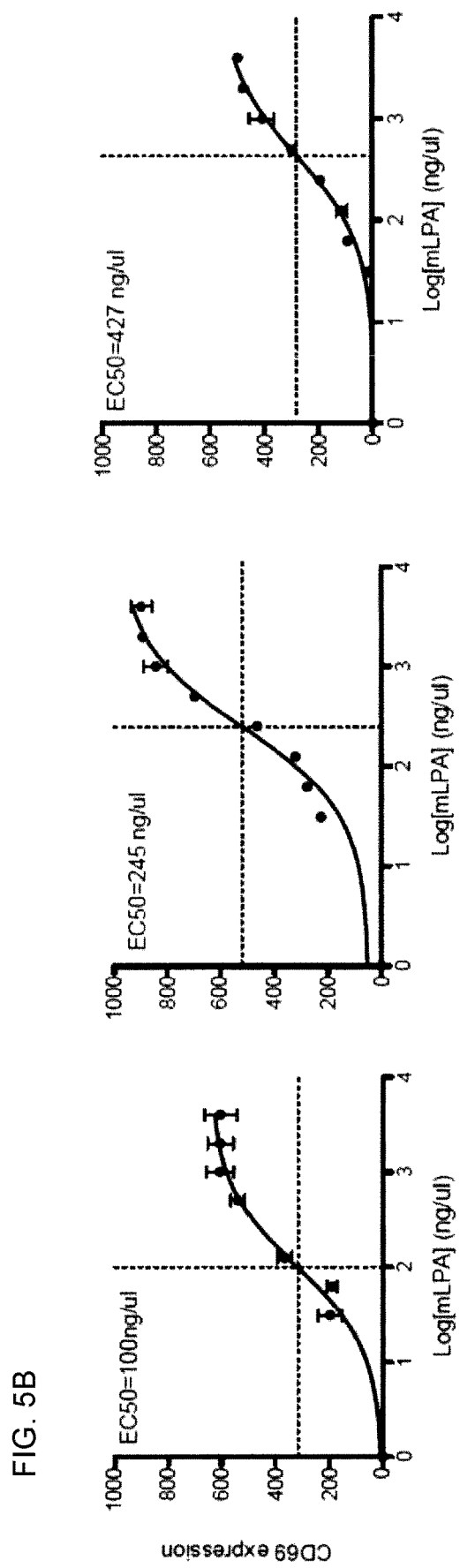

FIG. 5. TCR affinity for mLPA. FIG. 5A Expression of the CD1c self-reactive TCRs on the transduced and untransduced Jurkat 76 β2m$^-$ cells utilized for the mLPA titration reported in (B), as determined by flow cytometry with anti-mTCRβ mAb. FIG. 5B Lipid titration assay. Interpolation curve of CD69 expression on TCRtransduced Jurkat 76 β2m$^-$ cells in response to K562-CD1c cells loaded with indicated mLPA dilutions.

FIG. 6. Primary T cells transduced with mLPA-specific TCRs recognize leukemia cell lines. FIG. 6A TCRs expression on transduced and untransduced primary T cells as determined by flow cytometry with anti-mouse TCRb mAb, gating on CD3$^+$ cells. FIG. 6B Reactivity of primary T cells transduced with the mLPA-specific TCRs. Transduced primary T cells were plated in 96 U bottom-wells containing 4×10$^5$ THP1 either expressing (black bars) or not expressing (white bars) CD1c at E:T=2.5:1 ratio. After 24 h, IFNγ secreted in the supernatant was measured by ELISA assay. FIG. 6C Reactivity of primary T cells transduced with the mLPA-specific TCRs. Transduced primary T cells were plated in 96 U bottom-wells containing 4×10$^5$ K562 either expressing (black bars) or not expressing (white bars) CD1c at E:T=2.5:1 ratio. After 24 h, IFNγ secreted in the supernatant was measured by ELISA assay.

FIG. 7. Primary T cells transduced with the lead mLPA-specific TCR DN4.99 recognize and kill THP1-CD1c AML cell line. FIG. 7A CD8$^+$ T cells were sorted at day 10 post TCR-transduction and restimulated with anti-CD3/CD28 immunomagnetic beads and cytokines. TCR transduced or mock transduced T cells were plated in 96 u bottom-wells with 10$^5$ THP1-CD1c or THP1 WT cells at E:T=1:1 ratio. After 24 h, supernatant was collected and IFNγ production was measured by ELISA assay. FIG. 7B CD4+ T cells were sorted at day 10 post TCR-transduction and restimulated with anti-CD3/CD28 immunomagnetic beads and cytokines. TCR transduced or mock transduced T cells were plated in 96 u bottom-wells with $10^5$ THP1-CD1c or THP1 WT cells at E:T=1:1 ratio. After 24 h, supernatant was collected and IFN$\gamma$ production was measured by ELISA assay. FIG. 7C Killing of THP1-CD1c or THP1 WT AML cells by TCR-transduced or mock-transduced CD8+ T cells was evaluated by flow cytometry after 72 hours of coculture. FIG. 7D Killing of THP1-CD1c or THP1 WT AML cells by TCR-transduced or mock-transduced CD4+ T cells was evaluated by flow cytometry after 72 hours of coculture.

FIG. 8. Primary T cells transduced with the lead mLPA-specific TCR DN4.99 kill primary CD1c+ AML blasts. FIG. 8A CD1c expression on primary circulating Acute Myeloid Leukemia blasts (AML-04). FIG. 8B killing of primary CD1c+ AML-04 blasts (CD33+, arrows) by TCR DN4.99-transduced primary T cells after 72 h of co-culture at 10:1 E:T ratio.

Figure 9A:
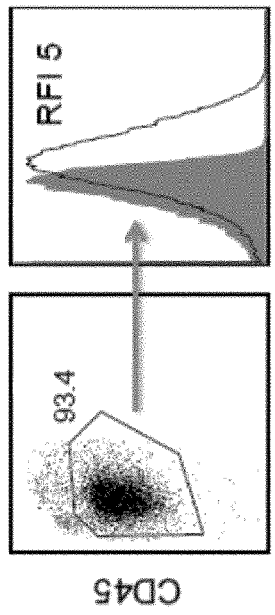
Figure 9B:
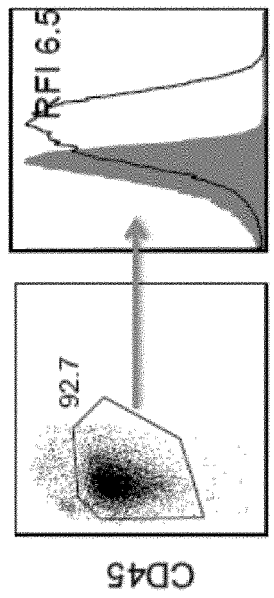
Figure 9:
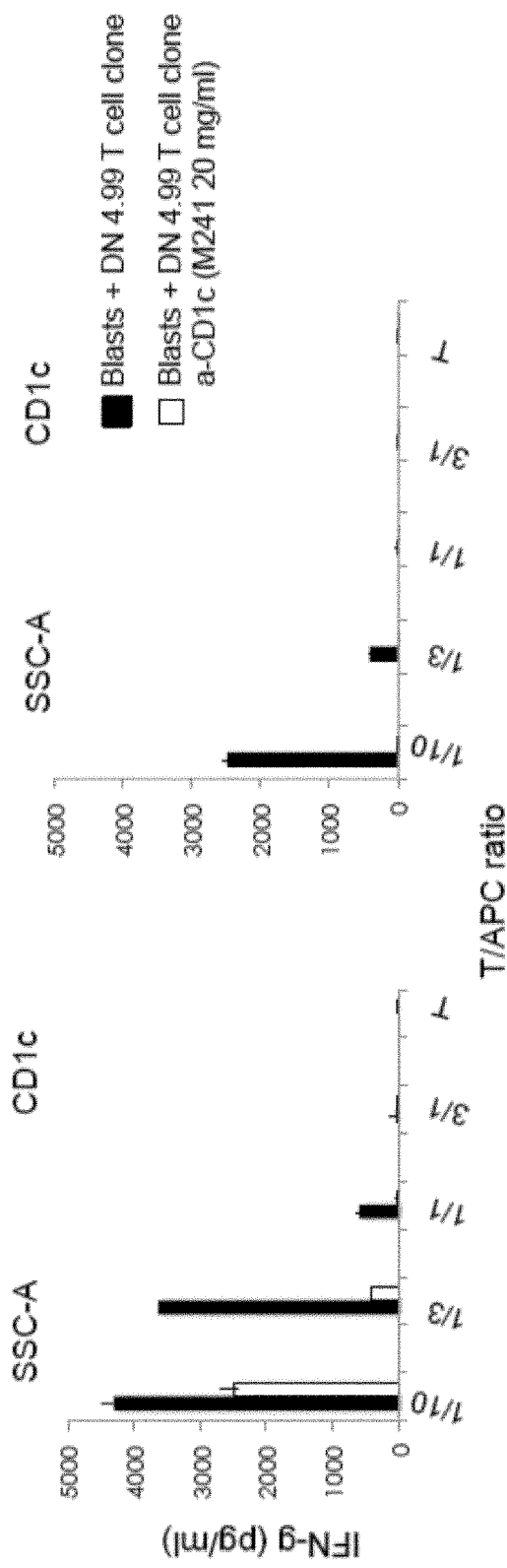

FIG. 9. the lead mLPA-specific T cell clone DN4.99 recognizes CD1c expressing blasts from a relapsing patient. FIG. 9A CD1c expression on primary circulating AML blasts (AML-34) at first diagnosis (left) and at post-transplant disease relapse (right). FIG. 9B IFN$\gamma$ production by DN 4.99 T cells upon 24 h coculture with primary blasts at first diagnosis (left) and relapse (right).

Figure 10:
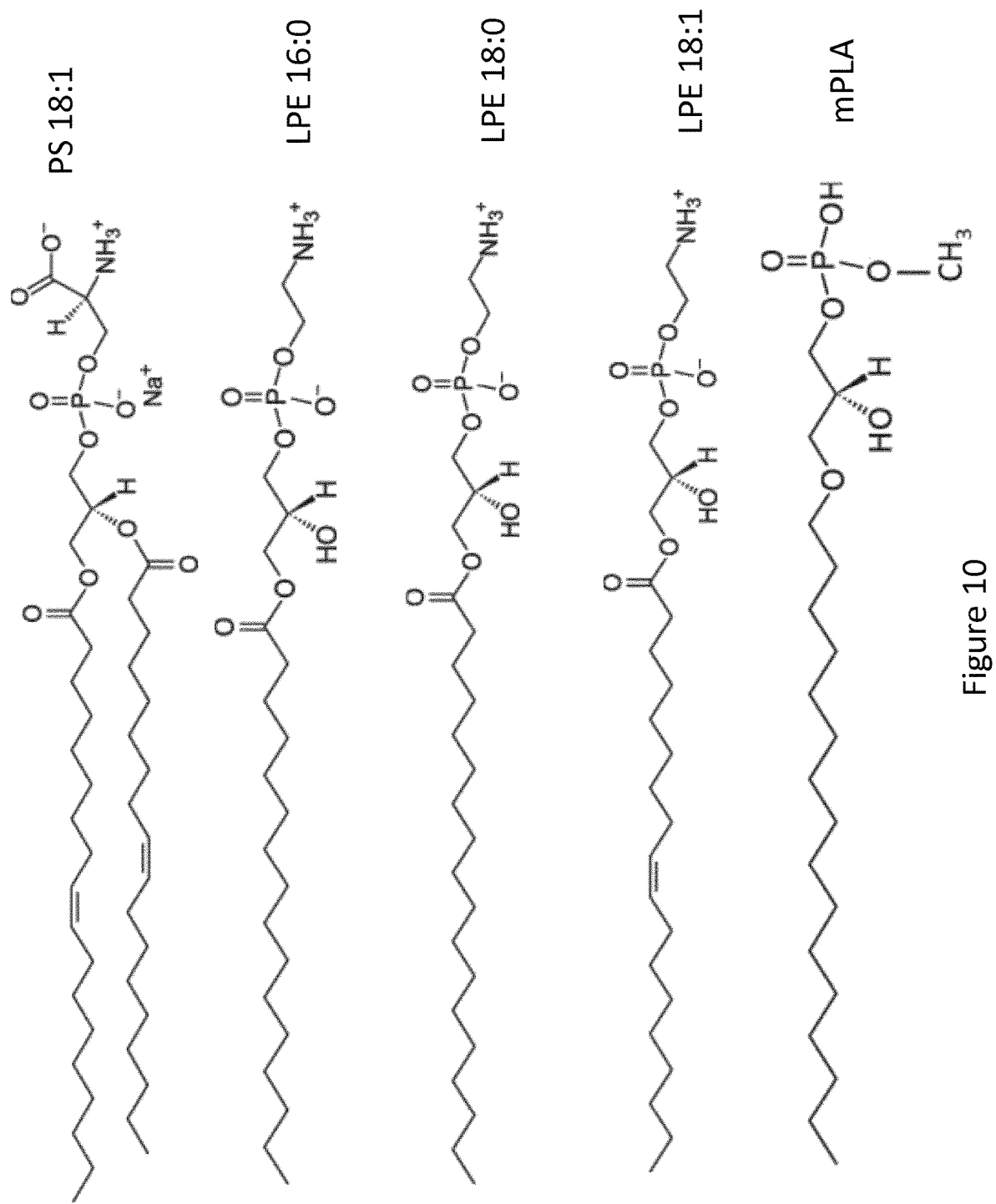

FIG. 10. Structure of the phospholipids tested for recognition by mLPA-specific TCRs.

FIG. 11. FIG. 11A Quantification of CD69 expression on Jurkat 76 cells transduced with mLPA specific TCR DN4.99 after ON co-culture with K562-CD1c AML cells loaded with 4 µg/ml of the indicated lipids. FIG. 11B Quantification of CD69 expression on Jurkat 76 cells transduced with mLPA specific TCR DN4.2 after ON co-culture with K562-CD1c AML cells loaded with 4 g/ml of the indicated lipids.

DETAILED DESCRIPTION OF THE INVENTION

Material and Methods

TCR$\alpha\beta$ Constructs and Cloning in Lentiviral Vectors cDNA coding for the TCR$\alpha$ and $\beta$ chains of the CD1c self-reactive T cell clones were synthetized by GeneArt and codon optimized for expression in eukaryotic cells. The sequence coding the TCR V$\alpha$ portions, fused in frame to the mouse C$\alpha$ sequence (SEQ NO. 11), are followed by the 2A peptide (EGRGSLLTCGDVEENPGP, SEQ ID NO. 57) and by the sequence coding the V regions of the TCR$\beta$ chain fused in frame with the murine C$\beta$ segment (SEQ NO. 12) which ends with a stop codon. The chimeric constructs were cloned into the pHR-SIN-BX-IRES-Em LV vector (a gift from E. Cerundolo, University of Oxford and Lepore M. et al J Exp Med. 2014 Jun. 30; 211(7):1363-77. doi: 10.1084/jem.20140410), in which the IRES-GFP cassette allows the identification of cells expressing the construct and can be easily excised by NotI/NotI digestion.

Production of Lentivirus in 293T Cells $9\times10^6$ 293T cells (HEK-293, ATCC® CRL-1573™) were seeded 24 h before transfection in a 15 cm petri dish with 20 ml of IMDM with L-glutamine, 10% FBS, and 100 U/ml Penicillin-Streptomycin. The medium was changed 2 h before transfection. The DNA mix was prepared by mixing 32 µg of transfer vector plasmid plus 9 µg pMD2.G-ENV (Addgene plasmid #12259), 16.25 µg of CMV$\Delta$R8.74 (Addgene plasmid #22036) and 6.25 µg of pRSV-REV (Addgene plasmid #12253, Dull T, Zufferey R, Kelly M, Mandel R J, Nguyen M, Trono D, Naldini L. J Virol. 1998 November 72(11):8463-71.) plasmids in a final volume of 1125 µl of TE 0.1×/H$_2$O (2:1; H$_2$O). 125 µl of 2.5M CaCl$_2$ were added to the plasmid mix and the precipitate was formed by drop wise addition of 1250 µl of HBS 2× solution to the DNA-TE-CaCl$_2$ mixture. The precipitate was immediately added to the 293T cells. After 14 h, the media in each dish was replaced with 16 ml of fresh complete medium and after further 30 h, the supernatant containing virus was collected, concentrated by ultracentrifugation and stored at -80° C.

Lentivirus Titration in Jurkat 76 Cells

Lentivirus was titrated by transducing Jurkat 76 cells that do not express the endogenous TCR. $25\times10^5$ Jurkat 76 cells were seeded in 48 wells plate and transduced with 7 serial dilution of supernatant from the packaging 293T cells containing the produce lentivirus ($10^{-2}$, $10^{-3}$, $10^{-4}$, $10^{-5}$, $10^{-6}$, $10^{-7}$, $10^{-8}$) in a final volume of 200 µl of RPMI medium 1640+GlutaMAX™, 10% FBS, 100 U/ml Penicillin-Streptomycin, 1 mM Sodium Pyruvate and 0.1 mM MEM NEAA. Fresh media was added 24 h after transduction to a final volume of 1 ml per well. After 4 days from the transduction, the expression of chimeric TCRs were detected by flow cytometry with anti-mouse TCR C$\beta$ mAb (Biolegend) or GFP. To calculate viral titer (transducing unit (TU)/ml) the following equation was used:

$$TU/ml = \frac{\left(\frac{\text{positive cells percentage}}{100}\right)(\text{dilution factor})}{\text{Inoculum Volume (ml)}} (\text{infected cells number})$$

To have a reliable estimation of lentivirus titer, the range of positive cells between 5-30% was considered.

Jurkat 76 Cells Transduction with Lentiviral Vectors $5\times10^5$ Jurkat 76 cells (Hart D P, Xue S A, Thomas S, Cesco-Gaspere M, Tranter A, Willcox B, Lee S P, Steven N, Morris E C, Stauss H J. Gene Ther. 2008 April; 15(8):625-31) were seeded in 48 wells plate in a final volume of 200 µl RPMI medium 1640+GlutaMAX™, 10% FBS, 100 U/ml Penicillin-Streptomycin, 1 mM Sodium Pyruvate and 0.1 mM MEM NEAA. Jurkat 76 cells were transduced with MOI 100 and 24 hs after the transduction fresh media was added to a final volume of 1 ml per well. The expression of chimeric TCRs was detected 4 days after the transduction by flow cytometry analysis with anti mouse TCR C$\beta$ mAb.

Jurkat 76 $\beta$2m$^-$ Cells Transduction with Lentiviral Vectors $5\times10^5$ Jurkat 76 $\beta$2m$^-$ cells were seeded in 48 wells plate in a final volume of 200 µl RPMI medium 1640+GlutaMAX™, 10% FBS, 100 U/ml Penicillin-Streptomycin, 1 mM Sodium Pyruvate and 0.1 mM MEM NEAA, and transduced with MOI 100. The expression of chimeric TCRs was detected 4 days after the transduction by flow cytometry analysis staining the cells with anti-mouse TCR Cβ mAb.

Primary Human T Cells Transduction with Lentiviral Vector

Peripheral blood mononuclear cells were purified from healthy donors. CD3+ cells were activated and expanded with Dynabeads® human T-Activator CD3/CD28, using the beads:T cells ratio=3:1. After 48 h in culture, $5\times10^5$ T cells were seeded in 48 wells plate in a final volume of 200 µl RPMI medium 1640+GlutaMAX™, 10% FBS, 100 U/ml Penicillin-Streptomycin, 1 mM Sodium Pyruvate, 0.1 mM MEM NEAA, 100 U/ml rhIL2 and 10 ng/ml hrIL-7. T cells were transduced with MOI 100 and 24 h after fresh media was added to a final volume of 1 ml per well. The expression of the transduced TCRs was verified after 4 days by flow cytometry using anti-mouse TCR Cβ mAb. CD4+ and CD8+ T cells expressing or not expressing the transduced TCRs were sorted 14 days after the transduction. Sorted T cells were re-expanded with Dynabeads® human T-Activator CD3/CD28 at a beads:T cells ratio=1:10 and 100 U/ml rhIL2 and 10 ng/ml hrIL-7.

Recognition of Leukemia Cell Lines by TCR-Transduced Jurkat 76 Cells $4\times10^4$ THP1-CD1c, or K562-CD1c (a gift of Dr. D. Branch Moody, Harvard University, Boston, USA de Jong A, Peña-Cruz V, Cheng T Y, Clark R A, Van Rhijn I, Moody D B. Nat Immunol. 2010 December; 11(12):1102-9) target cells or THP1 (ATCC® TIB-202™) or K562 (ATCC® CCL243™) WT cells, were plated complete medium (RPMI 10% FCS+1% P/S+1% NEAA+1% NaPyr, 2-ME) in 96 U bottom-wells. When indicated, THP1-CD1c or K562-CD1c cells were also pre-loaded with 4 µg/ml of mLPA for 4 h at 37° C. 105 Jurkat 76 cells expressing the transduced TCRs were added to the target cells in a final volume of 100 µl of complete medium. After overnight (ON) at 37° C., the expression of CD69 were analyzed by flow cytometry with anti-CD69 mAb (Biolegend).

Recognition Assay of THP1 Cells by Transduced Jurkat 76 Cells $4\times10^4$ THP1-CD1c target cells, or negative control THP1 WT cells, were plated in 50 ul of complete medium (RPMI 10% FCS+1% P/S+1% NEAA+1% NaPyr, 2-ME) in 96 U bottom-wells. When indicated, THP1-CD1c cells were also pulsed with 4 µg/ml of mLPA for 4 h at 37° C. $10^5$ Jurkat 76 cells expressing the transduced TCRs were added to the target cells in a final volume of 100 ul of complete medium. After ON at 37° C., the expression of CD69 were analyzed by flow cytometry with anti-CD69 mAb (Biolegend).

Recognition of Leukemia Cell Lines by TC-Transduced Primary Human T Cells

For primary T cell recognition, $10^5$ THP1-CD1c or K562-CD1c target cells, or negative control THP1 and K562 WT cells, were plated in complete medium (RPMI 10% FCS+ 1% P/S+1% NEAA+1% NaPyr, 2-ME) in 96 U bottom-wells. $10^5$ T cells expressing or not expressing the transduced TCRs were added to target cells in 100 µl of complete medium and incubated at 37° C. ON. When indicated, TCR-transduced CD4+ or CD8+ T cells were separated by cell sorting before the assay. A 50 µl aliquot of supernatant from each condition was collected and the secreted IFNγ was measured by ELISA. After additional 4 days of coculture, the killing of target cells was evaluated by flow cytometry analysis, by staining cells with DAPI, anti-mTCR Cβ and anti-CD33 to determine the elimination of CD33+ leukemia cells.

Recognition Assay of THP1 Cells by Transduced Human T Cells

For primary T cell recognition, $10^5$ THP1-CD1c target cells, or negative control THP1 WT cells, were plated in 50 ul of complete medium (RPMI 10% FCS+1% P/S+1% NEAA+1% NaPyr, 2-ME) in 96 U bottom-wells. $10^5$ CD4+ or CD8+ T cells expressing or not expressing the transduced TCRs were added to target cells in 100 ul of complete medium and incubated at 37° C. A 50 µl aliquot of supernatant from each condition was collected after ON and the secreted IFNγ was measured by ELISA. After additional 4 days of coculture, the killing of target cells was evaluated by flow cytometry analysis staining cells with DAPI, anti-mTCR Cβ and anti-hCD33.

Killing Assay

Killing assays were performed using primary AML blasts (obtained from the San Raffaele Biobank) incubated either alone or with T cells ($2\times10^4$ cells/ml) at 10:1 Effector T cell:Target leukemia cell, in the presence or absence of the CD1c blocking antibody anti-CD1c mAb (clone M241 Santa Cruz, Calif.). After 72 h residual viable target cells were identified and quantitated as DAPI−/CD33+/CD3− by flow cytometry.

T Cell Activation Assay

T cell activation assay was performed by co-culturing the indicated numbers of target cells with T cells ($20\times10^4$/well) in the presence or in the absence of anti-CD1c (clone M241, Santa Cruz, Calif.) blocking monoclonal antibody. Supernatants were collected after 48 h and IFN-γ was measured by ELISA.

In FIG. 11, $4\times10^4$ THP1-CD1c target cells were plated in 50 ul of complete medium (RPMI 10% FCS+1% P/S+1% NEAA+1% NaPyr, 2-ME) in 96 U bottom-wells. THP1-CD1c cells were also pulsed with 4 µg/ml of the indicated lipids for 4 h at 37° C. Synthetic PS18:1, LPE16:0, LPE18:0, LPE18:1 were obtained by Dr Matthew Skaley, University of Oklahoma Health Sciences Center Oklahoma City, USA. Synthetic mLPA was obtained from Prof. Gennaro De Libero, University of Basel, CH) $10^5$ Jurkat 76 cells expressing the transduced TCRs were added to the target cells in a final volume of 100 ul of complete medium. After ON at 37° C., the expression of CD69 were analyzed by flow cytometry with anti-CD69 mAb (Biolegend).

| CLONES V segment N region (bold) J segment (lower case) Underlined: CDR regions | Sequences |
|---|---|
| CLONE DN4.99 TRAV3 8.2-Ja44 | MACPGFLWALVISTCLEFSMAQTVTQSQPEMSVQEAETVTLSCTYDTSESDYILFWYKQPPSRQ<br>                                              CDR1<br>MILVIRQEAYKQQNATENRFSVNFQKAAKSFSLKISDSQLGDAAMYFCAYRSPLntgtaskltfgtgtrl<br>       CDR2                                                   CDR3<br>qvtl (SEQ ID NO. 1) |
| TRBV28-Jb2.7 | MGIRLLCRVAFCFLAVGLVDVKVTQSSRYLVKRTGEKVFLECVQDMDHENMFWYRQDPGLGLR<br>                                      CDR1<br>LIYFSYDVKMKEKGDIPEGYSVSREKKERPSLILESASTNQTSMYLCASSPWVssyegyfgpgtrltvt<br>       CDR2                                             CDR3<br>(SEQ ID NO. 2) |
| CLONE CD4P8E3 TRAV38-1-J31 | MTRVSLLWAVVSTCLESGMAQTVTQSQPEMSVQEAETVTLSCTYDTSENNYYLFWYKQPPSR<br>                                      CDR1<br>QMILVIRQEAYKQQNATENRFSVNFQKAAKSFSLKISDSQLGDTAMYFCAFAnnarlmfgdgtqlvvk<br>       CDR2                                                 CDR3<br>p (SEQ ID NO. 3) |
| TRBV28-J1.1 | MGIRLLCRVAFCFLAVGLVDVKVTQSSRYLVKRTGEKVFLECVQDMDHENMFWYRQDPGLGLR<br>                                      CDR1<br>LIYFSYDVKMKEKGDIPEGYSVSREKKERPSLILESASTNQTSMYLCASTDTgnteaffgqgtrltyv<br>       CDR2                                             CDR3<br>(SEQ ID NO. 4) |
| CLONE DN4.2 TRAV26-2-J53 | MKLVTSITVLLSLGIMGDAKTTQPNSMESNEEEPVHLPCNHSTISGTDYIHWYRQLPSQGPEYVI<br>                                        CDR1<br>HGLTSNVNNRMASLAIAEDRKSSTLLIHRATLRDAAVYYCILRLRggsnykltfgkgtlltvmp (SEQ ID<br>       CDR2                                       CDR3<br>NO. 5) |
| TRBV4-1-J2.1 | MGCRLLCCAVLCLLGAGPIDTEVTQTPKHLVMGMTNKKSLKCEQHMGHRAMYWYKQKAKKPP<br>                                          CDR1<br>ELMFVYSYEKLSINESVPSRFSPECPNSSLLNLHLHALQPEDSALYLCASSPIMGLAATHneqffgpg<br>       CDR2                                                  CDR3 |

-continued

| | Sequences |
|---|---|
| trltvl (SEQ ID NO. 6) | |
| CLONE PZ-CD8 P8A6 TRAV26-2-J44 | MKLVTSITVLLSLGIMGDAKTTQPNSMESNEEEPVHLPCNHSTISGTDYIHWYRQLPSQGPEYVI<br>                                              CDR1<br>HGLTSNVNNRMASLAIAEDRKSSTLILHRATLRDAAVYYCILRDvntgtasklfgtgtrlqvtld (SEQ<br>   CDR2                               CDR3<br>ID NO. 7) |
| TRBV4-1-J2-3 | MGCRLLCCAVLCLLGAGPIDTEVTQTPKHLVMGMTNKKSLKCEQHMGHRAMYWYKQKAKKPP<br>                                              CDR1              CDR2<br>ELMFVYSYEKLSINESVPSRFSPECPNSSLLNLHLHALQPEDSALYLCASSRLGLstdtcyfgpgtrltvl<br>                                                   CDR3<br>(SEQ ID NO. 8) |
| CLONE DN7.6.16 TRAV13.1-J28 | MTSIRAVFIFLWLQLDLVNGENVEQHPSTLSVQEGDSAVIKCTYSDSASNYFPWYKQELGKGPQL<br>                                           CDR1<br>IIDIRSNVGEKKDQRIAVTLNKTAKHFSLHITETQPEDSAVYFCAAPRglgvtnelsgrgpnsrsyqn<br>    CDR2                                        CDR3<br>(SEQ ID NO. 9) |
| TRBV27-J2.1 | MGPQLLGYVVLCLLGAGPLEAQVTQNPRYLITVTGKKLTVTCSQNMNHEYMSWYRQDPGLGLR<br>                                              CDR1<br>QIYYSMNVEVTDKGDVPEGYKVSRKEKRNFPLILESPSPNQTSLYFCASSLVWGTyneqfgpgtrltv<br>      CDR2                                          CDR3<br>1 (SEQ ID NO. 10) |
| Murine constant region alpha | D I Q N P E P A V Y Q L K D P R S Q D S T L C L<br>F T D F D S Q I N V P K T M K S G T F I T D K T<br>V L D M K A M D S K S N G A I A W S N Q T S F T<br>C Q D I F K E T N A T Y P S S D V P C D A T L T<br>E K S F E T D M N L N F Q N L S V M G L R I L L<br>L K V A G F N L L M T L R L W S S (SEQ ID NO. 11) |
| Codon optimized mCa nucleotide sequence | atCcagaaccagagcctgctgtgtaccagtcagaaagatcctcgtgttcaccgactttgactcc<br>caaatcaatgtgccgaaaactatgaaatcgggaacgttcatcactgacaaaactgctgacatgaaagctgatggattccaaga<br>gcaatgggcagccatgcctgagcaacgaacaagcttcactgacctgccaagatatcttcaaagagaccaacgcaacctacccagttc<br>agacgttccctgtcctgatgcaccgtgaagtagcggaaaagtttgaacaagacatgatgaacctaaactttcaaaacctgagtgtgatggga<br>ccgaatcccctgctgaaagtagcggggattaacctgctcatgacgctgaggctgtggtctccagt (SEQ ID NO. 58) |
| Murine constant region beta 1 | E D L R N V T P P K V S L F E P S K A<br>E I A N K Q K A T L V C L A R G F F P<br>D H V E L S W W V N G K E V H S G V S |

-continued

| | Sequences |
|---|---|
| | T D P Q A Y K E S N Y S Y C L S S R L<br>R V S A T F W H N P R N H F R C Q V Q<br>F H G L S E E D K W P E G S P K P V T<br>Q N I S A E A W G R A D C G I T S A S<br>Y H Q G V L S A T I L Y E I L L G K A<br>T L Y A V L V S G L V L M A M V K K K<br>N S (SEQ ID No. 12) |
| | Codon optimized mCb 1 nucleotide sequence<br>Gaggatctgagaaatgaactccaccaagtctccttgttgagccatcaaaagtcagagaattgcaaacaaacaaaaggctaccc<br>tcgtgcttggccagggctctccctgaccacgtgagctgagctgtgggtgaatgcaaggagtccacagtgggtcagc<br>acggacccaggcctacaaggagagcaattatgctactgcctgagcagccgctgagggtctctgctacctctggcacaatcc<br>tcgaaaccactccgctgccaagtcagttccatggcttcagaggaggacaagtggcagaggcttcacccaaacctgtcaca<br>cagaacatcagtcagagggctgggcgcagagctgcagcagctgtgaatcctcagcaggggttctgtctgcaaccat<br>ccctcatgagatcctactgggaaggccacctatgctgtcagtggctgtcagtggcctggtgctgatggccatggtcaagaaaaaa<br>attcctga (SEQ ID NO. 59) |
| | Human Constant region alpha sequence:<br>IQNPDPAVYQLRDSKSSDKSVCLFTDFDSQTNVSQSKDSDVYITDKTVLDMRSMDFKSNSAVAW<br>SNKSDFACANAFNNSIIPEDTFFPSPESSCDVKLVEKSFETDTNLNFQNLSVIGFRILLLKVAGFNL<br>LMTLRLWSS (SEQ ID No. 13) |
| | Codon optimized hCa nucleotide sequence<br>ATCCAGAACCCCGACCCCGCCGTGTACCAGCTGCGGGACAGCAAGTCGGACAAGAGCGTGT<br>GCCTGTTCACCGACTTCGACAGCCAGACCAACGTGAGCCAGAGCAAGGACTCCGACGTGTACAT<br>CACCGACAAGTGCGTGCTGGACATGCGGAGCATGGACTTCAAGAGCAACTCCGCCGTGGCCTGG<br>TCCAACAAGAGCGACTTCGCCTGCGCCAACGCCTTCAACAACAGCATCATCCCCGAGGACACCT<br>TTTTCCCCAGCCCCGAGAGCAGCTGCGACGTGAAACTGGTGGAGAAGAGCTTCGAGACCGACAC<br>CAACCTGAACTTCCAGAACCTGAGCGTGATCGGCTTCAGAATCCTGCTGCTGAAGGTGGCCGGC<br>TTCAACCTGCTGATGACCCTGCGGCTGTGGAGCAGC (SEQ ID NO. 60) |
| | Human Constant beta sequence:<br>EDLKNVFPPEVAVFEPSEAEISHTQKATLVCLATGFYPDHVELSWWVNGKEVHSGVSTDPQPLK<br>EQPALNDSRYCLSSRLRVSATFWQNPRNHFRCQVQFYGLSENDEWTQDRAKPVTQIVSAEAWG<br>RADCGFTSESYQQGVLSATILYEILLGKATLYAVLVSALVLMAMVKRKDSRG (SEQ ID No. 14) |
| | Codon optimized hCb nucleotide sequence<br>GAGGACCTGAAGAACGTGTTCCCCCCGAGGTGGCCGTGTTCGAGCCCAGCGAGGCCGAGATCA<br>GCCACACCCAGAAAGCCACCCTGGTCTGCCTGGCCACCGGCTTCTACCCCGACCACGTGAGCTG<br>TCTTGTGGGTGAACGGCAAAGAGGTGCACAGCGGCGTCTGCACCGACCCCCAGCCCTGAAAG<br>AGCAGCCCGCCTGAACGACAGCCGGTACTGCCTGAGCAGCCGGCTGAGAGTGAGCGCCACCTT<br>CTGGCAGAACCCCCGGAACCACTTCCGGTGCCAGGTGCAGTTCTACGGCCTGAGCGAGAACGAC<br>GAGTGGACCCAGGACCGAGAGCCGTGACCCAGATCGTGAGCGCCGAGGCCTGGGGCAGAG<br>CCGACTGCGGCTTCACCAGCGAGAGCTACCAGCAGGGCGTGCTGTCCGCCACCATCCTGTACGA<br>GATCCTGCTGGGCAAGGCCACACTGTACGCCGTGCTGGTGTCCGCCCCTGTGCTGATGGCTATG<br>GTGAAGCGGAAGGACAGCCGGGGCTGA (SEQ ID NO. 61) |

In bold = N region
In underlined = J region

TCR from clone DN4.99

-continued

Sequences

Sequence of the TCR Va region of T cell clone DN4.99
TRAV38-2 (Va14.1)-Ja44

```
1/1                                                 31/11                                              61/21
GAA TTC GCC CTT GTG CAG CAG GGA CCT GTG AGC ATG GCA TGC CCT GGC TTC CTG TGG GCA CTT GTG ATC TCC ACC TGT CTT GAA TTT AGC
                                        M   A   C   P   G   F   L   W   A   L   V   I   S   T   C   L   E   F   S
                                                            TRAV38-2 (Va14.2)
91/31                                               121/41                                             151/51
ATG GCT CAG ACA GTC CTG CAG CAG TCT CCA CAA GAG ATG TCT GTG CAG GAG GCA GAG ACC GTG ACC CTG AGC TGC ACA TAT GAC ACC AGT GAG
 M   A   Q   T   V   L   Q   Q   S   P   Q   E   M   S   V   Q   E   A   E   T   V   T   L   S   C   T   Y   D   T   S   E

181/61                                              211/71                                             241/81
AGT GAT TAT TAT TTA TTC TGG TAC AAG CAG CCT CCC AGC CAG AGG ATG ATT CTC GTT ATT CGC CAA GAA GCT TAT AAG CAA CAG AAT GCA
 S   D   Y   Y   L   F   W   Y   K   Q   P   P   S   Q   R   M   I   L   V   I   R   Q   E   A   Y   K   Q   Q   N   A

271/91                                              301/101                                            331/111
ACA GAG AAT CGT TTC TCT GTG AAC TTC CAG AAA GCC AAA TCC TTC AGT CTC AAG ATC AGT GAC TCA CAG CTT TCA GAT GCT GCG ATG
 T   E   N   R   F   S   V   N   F   Q   K   A   K   S   F   S   L   K   I   S   D   S   Q   L   S   D   A   A   M
                                            Ja44
361/121                                             391/131                                            421/141
TAT TTC TGT GCT TAT AGG AGC AGC TTA CCC AAT ACC GGC ACT GCC AGT AAA CTC ACC TTT GGG ACT GGA ACA AGA CTT CAG GTC ACG CTC    (SEQ ID No. 15)
 Y   F   C   A   Y   R   S   S   L   P   N   T   G   T   A   S   K   L   T   F   G   T   G   T   R   L   Q   V   T   L    (SEQ ID NO. 1)
                N-region
```

Sequence of the TCR Vb region of T cell clone DN4.99
TRBV28 (Vb3.1)-Jb2.7

```
1/1                                                 31/11                                              61/21
ccc acc atg gga atc agg agg ctc ctc tgt cgt gtg gcc ttt ctg gct gta ggc ctc gta gat gtg aaa gta acc cag agc tcg aga
         M   G   I   R   R   L   L   C   R   V   A   F   L   A   V   G   L   V   D   V   K   V   T   Q   S   S   R
                 TRBV28 (Vb3.1)
91/31                                               121/41                                             151/51
tat cta gtc aaa agg acg gga gag aaa gtt ttt ctg gaa tgt gaa cag cat atg gac cat gaa aat atg ttc tgg tat cga caa gac cca
 Y   L   V   K   R   T   G   E   K   V   F   L   E   C   E   Q   H   M   D   H   E   N   M   F   W   Y   R   Q   D   P 181/61                                              211/71                                             241/81
ggt ggg cta cgg ctg atc tat ttc tca tat gtt gat gta aaa gaa aaa gga gat att cct gag ggg tac agt gtc tct aga gag
 G   G   L   R   L   I   Y   F   S   Y   V   D   V   K   M   K   E   K   G   D   I   P   E   G   Y   S   V   S   R   E 271/91                                              301/101                                            331/111
aag gag cgc ttc tcc ctg att ctg gag tcc gcc agc acc aac cag agc aca tct atg tac ctc tgt gcc agc agt CCA TGG GTA AGC TCC
 K   E   R   F   S   L   I   L   E   S   A   S   T   N   Q   S   T   S   M   Y   L   C   A   S   S   P   W   V   S   S
                                                                                          N region    | Jb2.7
361/121                                             391/131
```

-continued

| | Sequences |
|---|---|

TAC GAG CAG TAC TTC GGG CCG GGC ACC AGG CTC ACG GTC ACA SEQ ID No. 16
 Y   E   Q   Y   F   G   P   G   T   R   L   T   V   T  SEQ ID NO. 2

TCR from clone CD4-P8E3
TCR Valfa chain clone CD4 P8E3 TRAV38-1 (Va14.2)-Ja31
1/1                                      31/11                                    61/21
─────────────────────────────────────────┬──────────────────────────────────────┬─
atg aca cga gtt agc ttg ctg tgg gca gtc gtg gtc tcc acc tgt ctt gaa tcc ggc atg gcc cag aca gtc act cag tct caa cca gag
 M   T   R   V   S   L   L   W   A   V   V   V   S   T   C   L   E   S   G   M   A   Q   T   V   T   Q   S   Q   P   E 91/31                                    121/41                                   151/51
─────────────────────────────────────────┬──────────────────────────────────────┬─
atg tct gtg cag gca gag act gtg acc ctg agt tgc aca tat gac acc agt gag agt aat tat tat ttg ttc tgg tac aag cag cct
 M   S   V   Q   A   E   T   V   T   L   S   C   T   Y   D   T   S   E   N   Y   Y   L   F   W   Y   K   Q   P 181/61                                   211/71                                   241/81
─────────────────────────────────────────┬──────────────────────────────────────┬─
ccc agc cag cag atg att ctc gtt att cgc caa gaa gct tat aag caa cag aat gca acg gag aat cgt ttc tct gtg aac ttc cag aaa
 P   S   Q   Q   M   I   L   V   I   R   Q   E   A   Y   K   Q   Q   N   A   T   E   N   R   F   S   V   N   F   Q   K 271/91                                   301/101                                  331/111                  N region        Ja31
─────────────────────────────────────────┬──────────────────────────────────────┬──────────────────────────────────────
GCA AAA TCC TTC AGT CTC AAG ATC TCA GAC CAG GGG GAC ACT GCG ATG TAT TTC TGT GCT TTC GCA AAC AAT GCC AGA CTC
 A   K   S   F   S   L   K   I   S   D   Q   G   D   T   A   M   Y   F   C   A   F   A   N   N   A   R   L 361/121                                  391/131
─────────────────────────────────────────┬─
ATG TTT GGA GAT GGA ACT CAG CTG GTG GTG AAG CCC (SEQ ID No. 17)
 M   F   G   D   G   T   Q   L   V   V   K   P  (SEQ ID No. 3)

TCR Vbeta clone CD4 P8E3 (= P11D10) TRBV28 (Vb3)-Jb1.1
                                    TRBV28
1/1                                      31/11                                    61/21
─────────────────────────────────────────┬──────────────────────────────────────┬─
act gcc tgg tcc tgg gag aag acc tat tct ttc ttc aaa gca gcc atg ggg atc agg ctc ctc tgt gtg gcc ttt tgc ttt ctg gct
 T   A   W   S   W   E   K   T   Y   S   F   F   K   A   A   M   G   I   R   L   L   C   V   A   F   C   F   L   A 91/31                                    121/41                                   151/51
─────────────────────────────────────────┬──────────────────────────────────────┬─
gta ggc ctc gta gat gta aaa gta acc cag agc tcg aga tat cta gtc aaa agg acg gga gag aaa gtt ttt ctg gaa tgt gtc cag gat
 V   G   L   V   D   V   K   V   T   Q   S   S   R   Y   L   V   K   R   T   G   E   K   V   F   L   E   C   V   Q   D 181/61                                   211/71                                   241/81
─────────────────────────────────────────┬──────────────────────────────────────┬─
atg gac cat gaa aat atg ttc tgg tat cga caa gac cca ggg cta cgg ctg ctc ctg atc tat ttc tca tat gat gtt aaa atg aaa gaa
 M   D   H   E   N   M   F   W   Y   R   Q   D   P   G   L   R   L   L   I   Y   F   S   Y   D   V   K   M   K   E 271/91                                   301/101                                  331/111
─────────────────────────────────────────┬──────────────────────────────────────┬─
aaa gga gat att cct gag ggg tac agt gtc TCT AGA GAG AAG AAG GAG CGC TTC TCC CTG ATT CTG GAG TCC GCC AGC ACC AAC CAG ACA
 K   G   D   I   P   E   G   Y   S   V   S   R   E   K   K   E   R   F   S   L   I   L   E   S   A   S   T   N   Q   T -continued Sequences

```
361/121                                   N-region  391/131      Jb1.1                                         421/141
TCT ATG TAC CTC TGT GCC AGC ACT GAC ACT GGG AAC ACT GAA GCT TTC TTT GGA CAA GGC ACC AGA CTC ACA GTT GTA (SEQ ID No. 18)
 S   M   Y   L   C   A   S   T   D   T   G   N   T   E   A   F   F   G   Q   G   T   R   L   T   V   V    (SEQ ID NO.  4)

TCR from clone DN4.2
TCR alfa chain clone DN 4.2 TRAV26-2 (Va4.1)-Ja53
1/1                                                                            31/11
cac aga gtc tga gtt ctg ggg cct gga acc atg tgc act tca aca atg gag agt aac atg gag agt aac atg gag agt aac
                                                                                M   E   S   N   M   E   S
                                                                                TRAV26                          M 91/31                                                     121/41
ATT ATG GGT GAT GCT AAG ACC ACA CAG CCA AAT TCA ATG  GAG AGT AAC
 I   M   G   D   A   K   T   T   Q   P   N   S   M   E   S   N 181/61                                                     211/71
AGT GGA ACT GAT CAT TGG TAT CGA CAG CTT CCC TCC CAG  GGT CAG CTT CCC TCC CAG
 S   G   T   D   Y   I   H   W   Y   R   Q   L   P   S   Q   G   Q   L   P   S   Q 271/91                                                     301/101
aga atg gcc tct ctg gca atc gct gaa gac aga gct gaa  tcc agt acc ttg atc ctg
 R   M   A   S   L   A   I   A   E   D   R   K   S   S   T   L   I   L 361/121           N-region          Ja52                              391/131
tgc atc ctg aga tta aga gga ggt agc aac tat aaa ctg  aca ttt gga aaa gga act
 C   I   L   R   L   R   G   G   S   N   Y   K   L   T   F   G   K   G   T 421/141
                                                                                 ctc tta acc gtg aat cca (SEQ ID No. 19)
                                                                                  L   L   T   V   N   P   (SEQ ID NO.  5)

TCR beta chain clone DN4.2 TRBV4-1 (Vb7)-Jb2.1
1/1                                                                             31/11
atg ggc tgc agg ctc ctc tgc tgt gcg gtt ctc tgt ctt  cta gga gca ggt ccc ata gac act gaa gtt acc cag aca cca aaa cac ctg
 M   G   C   R   L   L   C   C   A   V   L   C   L   L   G   A   G   P   I   D   T   E   V   T   Q   T   P   K   H   L
                                           TRBV4-1                                                                      61/21

91/31                                                     121/41
gtc atg gga atg aca aat aag aag tct ttg aaa tgt gaa  caa cat atg ggg cac agg gct atg tat tgg tac aag cag aaa gct aag aag
 V   M   G   M   T   N   K   K   S   L   K   C   E   Q   H   M   G   H   R   A   M   Y   W   Y   K   Q   K   A   K   K
                                                                                                                  151/51

181/61                                                     211/71
cca ccg gag ctc atg ttt gtc tac agt tat gag aaa ctc  tct ata aat gaa agt gtg cca agt cgc ttc tca cct gaa tgc ccc aac agc
 P   P   E   L   M   F   V   Y   S   Y   E   K   L   S   I   N   E   S   V   P   S   R   F   S   P   E   C   P   N   S
                                                                                                                  241/81

271/91                                                     301/101                                          331/111
TCT CTC TTA AAC CTT CAC CTA CAC GCC CTG CAG CCA GAA GAC TCA GCC GCC AGC CCA ATC ATG GGA CTA GCA GCG GCG
                                                                                N-region
```

```
                                     -continued
                                     Sequences S   L   L   N   L   H   L   H   H   A   L   Q   P   E   D   S   A   L   Y   L   C   A   S   S   P   I   M   G   L   A   A
361/121     Jb2.1
ACC CAC AAT GAG CAG TTC TTC GGG CCA GGG ACA CGG CTC ACC GTG CTA              (SEQ ID NO. 20)
 T   H   N   E   Q   F   F   G   P   G   T   R   L   T   V   L              (SEQ ID NO. 6)

TCR from clone PZ-CD8 P8A6
TCR alfa chain clone PZ-CD8 P8A6 TRAV26-2 (Va4.1) -Ja44
1/1     TRAV26-2                                                    61/21
atg aag ttg gtg aca agc att act gta ctc tct ttg ggt att atg gat gct aag acc aca cag cca aat tca atg gag agt aac
 M   K   L   V   T   S   I   T   V   L   S   L   G   I   M   D   A   K   T   T   Q   P   N   S   M   E   S   N
91/31                                                    121/41
gaa gag cct gtt cac cct tgt aac cac tcc aca atc agt gga act gat tac ata cat tgg tat cga cag ctt cac tcc cag ggt
 E   E   P   V   H   P   C   N   H   S   T   I   S   G   T   D   Y   I   H   W   Y   R   Q   L   H   S   Q   G
181/61  211/71  241/81
CCA GAG TAC GTG ATT CAT CTT ACA AGO AAT GTG AAC AAC AGA ATG GCC TCT CTG GCA ATC GCT GAA GAC AGA AAG TCC AGT ACC TTG
 P   E   Y   V   I   H   L   T   S   N   V   N   N   R   M   A   S   L   A   I   A   E   D   R   K   S   S   T   L
271/91                                                   301/101                                         331/111    Ja44
ATC CAC CGT GCT ACC TTG AGA GAT GCT GCT GTG TAC TAC TGC GTA ATA ACC GGT ATA AAT ACC GGA ACT GCC AGT AAA CTC ACC TTT
 I   H   R   A   T   L   R   D   A   A   V   Y   Y   C   V   I   T   G   I   N   T   G   T   A   S   K   L   T   F
361/121                                              391/131
GGG ACT GGA ACA AGA CTT CAG GTC ACC CTC GAT              (SEQ ID NO. 21)
 G   T   G   T   R   L   Q   V   T   L   D              (SEQ ID NO. 7)

TCR beta chain clone PZ-CD8 P8A6 TRBV4-1 (Vb7.1) Jb2.3
1/1     TRBV4-1                                                    61/21
atg ggc tgc agg ctc ctc tgc tgt gcg gtt ctc tgt ctc ctg gga gca ggt ccc ata gac act gaa gtt acc cag aca cca aaa cac ctg
 M   G   C   R   L   L   C   C   A   V   L   C   L   L   G   A   G   P   I   D   T   E   V   T   Q   T   P   K   H   L
91/31                                                    121/41                                         151/51
gtc atg gga atg aca aat aag aag tct ttg aaa tgt gaa caa cat atg ggg cac agg gct atg tat tgg tac aag cag aag gct aaa
 V   M   G   M   T   N   K   K   S   L   K   C   E   Q   H   M   G   H   R   A   M   Y   W   Y   K   Q   K   A   K
181/61                                              211/71                                              241/81
cca ccg gag ctc atg ttt gtc tac agc tac gag aaa ctc tct ata aat gaa agt gtg cca agt cgc ttc tca CCT GAA TGC CCC AAC AGC
 P   P   E   L   M   F   V   Y   S   Y   E   K   L   S   I   N   E   S   V   P   S   R   F   S   P   E   C   P   N   S
271/91                                                   301/101                                         331/111
```

-continued

| Sequences |
|---|

```
TCT CTC TTA AAC CTT CAC CTA CAC GCC CTG CAG CCA GAA GAC TCA GCC CTG TAT CTC TGC GCC AGC AGC        CGG CTA GGA CTA TCC ACG GAT
 S   L   L   N   L   H   L   H   A   L   Q   P   E   D   S   A   L   Y   L   C   A   S   S         R   L   G   L   S   T   D
                                                                                                                       Jb2.3
                                                                                         N-region
361/121                                                                                 391/131

ACG CAG TAT TTT GGC CCA GGC ACC CGG CTG ACA GTG CTC      (SEQ ID No. 22)
 T   Q   Y   F   G   P   G   T   R   L   T   V   L       (SEQ ID NO. 8)

TCR from clone DN7.6.16
TCR alfa chain clone DN7.6.16 TRAV13.1 (Va8.1)-Ja28
1/1                                                                                              31/11

ATG aca tcc att cga gct gta ttt ata ttc ctg tgg ctg cag ctg gac Ttg gtg aat gga gag cat cct tca acc ctg
 M   T   S   I   R   A   V   F   I   F   L   W   L   Q   L   D   L   V   N   G   E   H   P   S   T   L 91/31                                                                                           121/41 agt gtc cag gag gac agc gct gtc tac ctt att ata gac att cgT TCA AAT GTG GGC tca gac agt tac tgt gtt act
 S   V   Q   E   D   S   A   V   Y   L   I   I   D   I   R   S   N   V   G   S   D   S   Y   C   V   T 181/61                                                                                          211/71 aaa gga cct cag CAC CTG CTG CAC ACC GAG ACC CAA CCT GAA GAC TCG GCT GTC TAC TTC TGT GCA GCA CCT CGC
 K   G   P   Q   H   L   L   H   T   E   T   Q   P   E   D   S   A   V   Y   F   C   A   A   P   R 271/91                                                                                          301/101

CAT TTC TCC CAC ATC ATC ACA GAG ACC CAA CCT GAA GAC TCG GCT GTC TAC TTC TGT GCA GCA CCT CGC         GGG CTG GGA GTT ACC AAC TCA
 H   F   S   L   H   I   I   T   E   T   Q   P   E   D   S   A   V   Y   F   C   A   A   P   R      G   L   G   V   T   N   S

331/111

CTT TCG GGA AGG GGA CCA AAC TCT CGG TCA TAC CAA AAT      (SEQ ID No. 23)
 L   S   G   R   G   P   N   S   R   S   Y   Q   N       (SEQ ID NO. 9)

TCR beta chain clone DN7.6.16 TRBV27 (Vb14) Jb2.1
1/1                                                                                              31/11

ATG ccc ccc ctt ggc ctt tat gtc ctt gcc cta gga gca ggc ccc ctg gaa gca ggc cca gcc cag acc cag cta atc
 M   P   P   L   G   L   Y   V   L   L   A   L   G   A   G   P   L   E   A   G   P   A   Q   T   Q   L   I 91/31                                                                                           121/41 aca gga act gga aag aag ttg aca gtg act cag tgt cct cag aat gtg acc caa aac cca gga cag gac gac ttc atc
 T   V   T   G   K   K   L   T   V   T   Q   C   P   Q   N   V   T   Q   N   P   R   Y   L   I 181/61                                                                                          211/71 tta agg cag atA tac tat tca atg aat gtt gag gtg act gat aag gga gat gtt cct gaa ggg tac aaa gtc tct cga aaa gAG AAG AGG
 L   R   Q   I   Y   Y   S   M   N   V   E   V   T   D   K   G   D   V   P   E   G   Y   K   V   S   R   K   E   K   R

241/81
```

```
                                    271/91                                                           301/101
                                    AAT TTC CCC CTG ATC GAG TCG CCC AAC CAG ACC CTG TAC TTC TGT GCC AGT AGC TTG GTC TGG GGA ACC TAC AAT GAG
                                     N   F   P   L   I   E   S   P   N   Q   T   L   Y   F   C   A   S   S   L   V   W   G   T   Y   N   E
                                                                                                 N-region       Jb2.1

361/121                                                          391/131
                                    CAG TTC TTC GGG CCA GGG ACA CGG CTC ACC GTG CTA                   (SEQ ID No. 24)
                                     Q   F   F   G   P   G   T   R   L   T   V   L                   (SEQ ID NO. 10)

In bred = N region
                                    In blue = J region
                                    In green murine constant region TCR from clone DN4.99
                                    Sequence of the TCR Va region of T cell clone DN4.99
                                    TRAV38 (Va14.2)-Ja44 fused with mCa
                                    1/1                                           31/11             TRAV38 (Va14.2)                   61/21
                                    GAA TTC GCC CTT CTG CAG CAG GGA CCT GTG AGC ATG GCA TGC CCT GGC TTC CTG TGG GCA CTT GTG ATC TCC ACC
                                     E   F   A   L   L   Q   Q   G   P   V   S   M   A   C   P   G   F   L   W   A   L   V   I   S   T 91/31                                         121/41                                              151/51
                                    ATG GCT CAG ACA GTC ACT CAG TCT CAA CCA GAG ATG TCT GTG CAG GAG GCA GAG ACC GTG ACC CTG AGC TGC ACA
                                     M   A   Q   T   V   T   Q   S   Q   P   E   M   S   V   Q   E   A   E   T   V   T   L   S   C   T 181/61                                        211/71                                              241/81
                                    AGT GAT TAT TAT TTA TTC TGG TAC AAG CAG CCT CCC AGC AGG CAG ATG ATT CTC GTT ATT CGC CAA GAA GCT TAT
                                     S   D   Y   Y   L   F   W   Y   K   Q   P   P   S   R   Q   M   I   L   V   I   R   Q   E   A   Y 271/91                                        301/101                                             331/111
                                    ACA GAG AAT TTC CGT AGT GTC AAT TTC CAG AAA GCA AAA AAA TCC TTC AGT CTC AAG ATC TCA GAC TCA CAG CTG
                                     T   E   N   F   R   S   V   N   F   Q   K   A   K   K   S   F   S   L   K   I   S   D   S   Q   L 361/121       JA44                            391/131                                             421/141
                                    TAT TTC TGT CCT TAT AGG AGC CCC TTA AAT ACC GGC CAG GCA AGT AAA CTC ACC TTT GGT ACT GGA ACA AGA CTT
                                     Y   F   C   P   Y   R   S   P   L   N   T   G   Q   A   S   K   L   T   F   G   T   G   T   R   L
                                         N-region 451/151                                       481/161                                             511/171
                                    ATC CAG AAC CCA GAT CCT GCT GTG TAC CAG CTA AGA GAT TCT AAA AGC TCT GAC AAG TCA GTC TGC CTG TTC ACC
                                     I   Q   N   P   D   P   A   V   Y   Q   L   R   D   S   K   S   S   D   K   S   V   C   L   F   T 541/181                                       571/191                                             601/201
                                    GAT TTT GAT TCT CAA ACA AAT GTG TCA CAA AGT AAG GAT TCT GAT GTG TAT ATC ACA GAC AAA ACT GTG CTA GAC
                                     D   F   D   S   Q   T   N   V   S   Q   S   K   D   S   D   V   Y   I   T   D   K   T   V   L   D mCA
                                    ATG AAA TCT ATG GAC TTC AAG AGC AAC AGT GCT GTG GCC TGG AGC AAC AAA TCT GAC TTT GCC TGT GCA AAT GCC
                                     M   K   S   M   D   F   K   S   N   S   A   V   A   W   S   N   K   S   D   F   A   C   A   N   A ATC AAT GTG CCG AAA ACC ATG GAA TCT GGA ACC TTC ATC ACT GAC AAA ACT GTG CTG GAC ATG AAA GCT ATG GAT TCC AAG AGC AAT GGG
                                     I   N   V   P   K   T   M   E   S   G   T   F   I   T   D   K   T   V   L   D   M   K   A   M   D   S   K   S   N   G
```

```
                                                 Sequences

I  N  V  P  K  T  M  E  S  G  T  F  I  T  D  K  T  V  L  D  M  K  A  M  D  S  K  S  N  G
631/211                                    662/221                                   691/231
 GCC ATT GCC TGG AGC AAC ACA AGC TTC ACC GAG ACC TGC CAA GAT ATC AAA GAG ACC AAC CCC AGT TCA GAC GTT CCC TGT
  A  I  A  W  S  N  Q  T  S  F  T  C  Q  D  I  F  K  E  T  N  A  T  Y  P  S  S  D  V  P  C
721/241                                    751/251                                   781/261
 GAT GCC ACG TTG ACC GAG AAA AGC TTT GAA ACA GAT ATG AAC CTA AAC TTT CAA AAC CTG TCA GTT ATG GGA CTC CGA ATC CTC CTG
  D  A  T  L  T  E  K  S  F  E  T  D  M  N  L  N  F  Q  N  L  S  V  M  G  L  R  I  L  L
811/271                                    841/281                                   871/291
 AAA GTA GCG GGA TTT AAC CTG CTC ACG CTG AGG TGG TCC AGT TGA GGA TCC CGA AGG GCG AAT TC (SEQ ID NO: 55)
  K  V  A  G  F  N  L  L  M  T  L  R  L  W  S  S  *

Sequence of the TCR Vb region of T cell clone DN4.99
TRBV28 (Vb3.1)-Jb2.7 fused with mCb
1/1 31/11 61/21
                                                                   TRBV28 (Vb3.1)
 ccc acc atg gga atc ctc cgt gtg gcc ctt tgt ctc ctg ggc cta gtg gat gta acc cag agc tcg aga
  P  T  M  G  I  L  R  V  A  L  C  L  L  G  L  V  D  V  T  Q  S  S  R
91/31                                     121/41                                   151/51
 tat cta gtc aaa agg acg gag aaa gtt ctg gaa tgt gtc cag gat atg gac cat gaa aat atg ttc tgg tat agt gtt
  Y  L  V  K  R  T  E  K  V  L  E  C  V  Q  D  M  D  H  E  N  M  F  W  Y  S  V
181/61                                    211/71                                   241/81
 ggt ctg ggg cta cgg ctg atc tat ttc tca tat gat gtc aaa atg aaa gaa gag aag ggt gat att cct gag ggg tac agt gtc tct aga gag
  G  L  G  L  R  L  I  Y  F  S  Y  D  V  K  M  K  E  E  K  G  D  I  P  E  G  Y  S  V  S  R  E
271/91                                    301/101                                  331/111 N region
 aag gag cgc ttc tcc ctg att ctg gag tcc gcc agc acc agc aca tct atg tac ctc tgt gcc agt                   |Jb2.7
  K  E  R  F  S  L  I  L  E  S  A  S  T  S  T  S  M  Y  L  C  A  S
361/121 391/131 421/141                                                            |Jb2.7
 tca aaa gca gag att gca aac aaa caa aag gct acc ctc gtg tgc ctg gcc gag gat ctg aga aat gtg act cca ccc aag gtc tcc ttg ttt gag cca CCA TGG GTA AGC TCC
  S  K  A  E  I  A  N  K  Q  K  A  T  L  V  C  L  A  E  D  L  R  N  V  T  P  P  K  V  S  L  F  E  P  P  W  V  S  S
                                                             mCb                                              E  D  L  R  N  V  T  P  P  K  V  S  L  P  E  P
451/151                                   481/161                                  511/171
 TAC GAG CAG TAC TTC GGG CCG GGC ACC AGG CTC ACG GTC ACA                                        tgg tat cgg cgg ttc ccg gtc cct ttc cct gac cac tgt gag ctg
  Y  E  Q  Y  F  G  P  G  T  R  L  T  V  T
541/181                                   571/191                                  601/201
 tca aaa gca gag att gca aac aaa caa aag gct acc ctc gtg tgc ctg gcc gag ggc ttc ttt gac cat gtg gag ctg agc tgg tgg
  S  K  A  E  I  A  N  K  Q  K  A  T  L  V  C  L  A  E  G  F  F  D  H  V  E  L  S  W  W
```

```
gtg aat ggc aag gag gtc cac agt ggg gtc agc acg gac cct cag gcc tac aag gag agc aat tac tgc agc agc cgc ctg
 V   N   G   K   E   V   H   S   G   V   S   T   D   P   Q   A   Y   K   E   S   N   Y   C   S   S   R   L 631/211                                    661/221                                       691/231
agg gtc tct gct acc ttc tgg cac aat cct cga aac cac ttc cgc tgc caa gtg cag ttc cat ggg ctt tca gag gag aag tgg cca
 R   V   S   A   T   F   W   H   N   P   R   N   H   F   R   C   Q   V   Q   F   H   G   L   S   E   E   D   K   W   P 721/241                                    751/251                                       781/261
gag ggc tca ccc aaa cct gtc aca cag aac atc agt gag gcc tgg ggc cga gac tgt gga atc act tca gca tcc tat cat cag
 E   G   S   P   K   P   V   T   Q   N   I   S   E   A   W   G   R   A   D   C   G   I   T   S   A   S   Y   H   Q 811/271                                    841/281                                       871/291
ggg gtt ctg tct gca acc atc ctc tat gag atc ctc ctg ggg aag gcc acc cta tat gct gtg gtc agt ggc ctg gtg ctg atg gcc
 G   V   L   S   A   T   I   L   Y   E   I   L   L   G   K   A   T   L   Y   A   V   L   V   S   G   L   V   L   M   A 901/301
atg gtc aag aaa aat tcc tga gac (SEQ ID NO: 56)
 M   V   K   K   N   S   *

SEQ ID NO. 25  YDTSESDYY

SEQ ID NO. 26  RQEAYK

SEQ ID NO. 27  RSPLNTGTASKLT

SEQ ID NO. 28  QDMDHENMF

SEQ ID NO. 29  SYDVKMK

SEQ ID NO. 30  SPWVSSYEQY

SEQ ID NO. 31  YDTSENNYY

SEQ ID NO. 32  RQEAYK

SEQ ID NO. 33  FANNARLM

SEQ ID NO. 34  QDMDHENMF

SEQ ID NO. 35  SYDVKMK

SEQ ID NO. 36  TDTGNTEAF

SEQ ID NO. 37  HSTISGTDY

SEQ ID NO. 38  GLTSNV
```

-continued

| | Sequences |
|---|---|
| SEQ ID NO. 39 | RLRGGSNYKLT |
| SEQ ID NO. 40 | QHMGHRAMY |
| SEQ ID NO. 41 | FVYSYEK |
| SEQ ID NO. 42 | SPIMGLAATHNEQF |
| SEQ ID NO. 43 | HSTISGTDYI |
| SEQ ID NO. 44 | GLTSNV |
| SEQ ID NO. 45 | RDVNTGTASKLT |
| SEQ ID NO. 46 | QHMGHRAMY |
| SEQ ID NO. 47 | FVYSYEK |
| SEQ ID NO. 48 | SRLGLSTDTQY |
| SEQ ID NO. 49 | YSDSASNYF |
| SEQ ID NO. 50 | DIRSNV |
| SEQ ID NO. 51 | PRGLGVTNSL |
| SEQ ID NO. 52 | QNMNHEYMS |
| SEQ ID NO. 53 | SMNVEV |
| SEQ ID NO. 54 | SLVWGTYNEQF |

Example 1

T Cell Transduction with Lentivirus Encoding the mLPA-Specific TCR Genes

To assess whether it was possible to generate primary T cell lines endowed with CD1c self-reactivity, the inventors transduced PBMCs from healthy donors with a lentivirus expressing the TCR α and β chains of a CD1c self-reactive mLPA-specific T cell clone. The inventors generated a lentivirus vector pHR-SIN-EGFP (provided by V. Cerundolo, Oxford, UK) encoding the TCR α and β genes from the mLPA specific T cell clone DN4.99, linked by 2A peptide. To improve the homologous pairing of the CD1c-restricted TCR and minimize mispairing with endogenous TCR chains, the inventors generated chimeric genes with the human V and the mouse C regions, as described (Canderan et al., 2010 Canderan G, Gruarin P, Montagna D, Fontana R, Melloni G, Traversari C, Dellabona P, Casorati G. An efficient strategy to induce and maintain in vitro human T cells specific for autologous non-small cell lung carcinoma. PLoS One. 2010 Aug. 9; 5(8):e12014.) (FIG. 1A). To generate the chimeric TCR chains, the TRAV38-TRAJ44 (SEQ ID NO: 15) and TRBV28-TRBJ2-7 (SEQ ID NO: 16) segments were fused with the mouse TRAC and TRBC cDNA, respectively, by PCR.

T cells were purified form healthy donors and activated with anti-CD3/CD28 immunomagnetic beads (Dynal) in RPMI-FCS complete medium supplemented with 100 U/ml hrIL-2 and 10 ng/ml IL-7 (R&D Systems). Two days after activation, $4 \times 10^5$ T cells were infected by lentivirus in 500 µl complete medium at a MOI of 5. After 15 days, transduced T cells were sorted for mouse TCRβ expression. Both positive and negative cells were stimulated with anti-CD3/CD28 immunomagnetic beads and cytokines and tested for antigen recognition after 10 days. Only the T cells displaying surface expression of the transduced TCR chains (i.e. only the mouse Cβ expressing cells), and not the untransduced ones sorted from the same cell line (FIG. 1B), recognized a CD1c expressing tumor cell line (FIG. 1C). Anti-CD1c-mAbs inhibited recognition, underscoring the specificity of the immune reaction.

These results indicated that mLPA-specific T cells, able to recognize leukemia blasts in CD1c-dependent manner, could be generated in vitro upon transduction of mLPA-specific TCR genes. This strategy might represent a relatively safe approach for immunotherapy of acute leukemia. Indeed allogeneic T cells from stem cell donors might be transduced and their eventual alloreactivity might be prevented by editing the endogenous TCR genes (Canderan et al., 2010 Canderan G, Gruarin P, Montagna D, Fontana R, Melloni G, Traversari C, Dellabona P, Casorati G. An efficient strategy to induce and maintain in vitro human T cells specific for autologous non-small cell lung carcinoma. PLoS One. 2010 Aug. 9; 5(8):e12014; Provasi et al., 2012 Provasi E, Genovese P, Lombardo A, Magnani Z, Liu PQ, Reik A, Chu V, Paschon D E, Zhang L, Kuball J, Camisa B, Bondanza A, Casorati G, Ponzoni M, Ciceri F, Bordignon C, Greenberg P D, Holmes M C, Gregory P D, Naldini L, Bonini C. Editing T cell specificity towards leukemia by zinc finger nucleases and lentiviral gene transfer. Nat Med. 2012 May; 18(5):807-15.). An issue that deserves careful evaluation is that mLPA-specific T cells killed also normal monocytes in vitro. In the case of mLPA-specific adoptive T cell therapy in the course of HSCT, this side effect might be tolerated by patients during the peritransplant period, when the control of minimal residual leukemia is paramount.

To determine the capacity to recognize leukemic cells by the two main T cell subsets present in transduced T cells, $CD4^+$ and $CD8^+$ T cells were sorted from a PBMC transduced with the lentiviral vector expressing the DN4.99 TCR (FIG. 2A) and tested for their ability to recognize $CD1c^+$ leukemia cells. Both $CD4^+$ (FIG. 2B) and $CD8^+$ (FIG. 2C) subsets were able to recognize the THP1-$CD1c^+$ target cell line. TCR-transduced $CD8^+$ T cells were also assessed for killing leukemia target cells. Only the TCR-transduced T cells specifically killed the leukemia cell line THP1 expressing CD1c, and not the THP1 WT cells (FIG. 2D). The arrows indicate the $CD33^+$ THP1 leukemia cell line that disappears after 72 hs of co-culture with $CD8^+$ T cells transduced with DN4.99 TCR.

These results show that both CD4+ and $CD8^+$ T cells can be successfully retargeted against CD1c+ leukemia cell lines by transducing CD1c self-reactive TCR, and confirm that transduced $CD8^+$ T cells are strongly cytotoxic against malignant cells

Generation of a Library of CD1c Self-Reactive TCRs to Target Leukemia Cells

To investigate the anti-leukemia efficacy of additional mLPA-specific TCRs, the inventors cloned the cDNA coding the TCRs from five different CD1c self-reactive T cell clones isolated from either healthy donors or leukemia patients. Table 1 reports the sequences of the TCRs.

TABLE 1

Sequences of the CDR3 regions of the TCR Va and Vb portions of the CD1c self reactive T cell clones.

| clone | TRAV | Va seq | N reg | Ja seq | | TRBV | Vb seq | N reg | Jb seq | |
|---|---|---|---|---|---|---|---|---|---|---|
| DN4.99 | TRAV38-1 | CAYRS | PL | NTGTASKLTFGTGTRLQVTL | J44 | TRBV28 | CASS | PWV | SSYEQYFGPGTRLTVT | J2-7 |
| CD4P8E3 | TRAV38-1 | CAF | A | NNARLMFGDGTQLVVKP | J31 | TR13V28 | CAS | TDTG | NTEAFFGTRLTVV | J1-1 |
| DN4.2 | TRAV26-1 | CILR | LR | GGSNYKLTFGKGTLLTVNP | J53 | TRBV4-1 | CASSP | IMGLAATH | NEQFFGPGTRLTVL | J2-1 |
| PZP8A6 | TRAV26-2 | CILRD | | VNTGTASKLTFGTGTRLQVTLD | J44 | TRBV4-1 | CASS | RLGL | STDTQYFGPGTRLTVL | J2.3 |
| DN7.6.16 | TRAV13.1 | CAA | PR | GLGVTNSLSGRGPNSRSYQN | J28 | TRBV27 | CASS | LVWGT | YNEQFFGPGTRLTVL | J2-1 |

For each TCR is reported the name of the clone, the name of the Va (TRAV) and Vb (TRBV) gene segments, the sequence of the last aa of the V regions (Va and Vb seq) starting from the conserved Cystein, the N-regions (N reg) and the sequences of the J segment (Ja seq and Jb seq).

As shown in Table 1, CD1c self-reactive T cell clones preferentially express either TRAV38 paired with TRBV28 or TRAV26 paired with TRBV4, even though they were isolated from different donors. The TCR Valpha chains are characterized by a very short N region sequence, while the Vbeta chains utilize very similar Jbeta segments. Both TCR Valpha and Vbeta chains contain diverse N regions, each characterizing a specific T cell clone (underlined in the sequence).

For each TCR the inventors generated a lentiviral vector in which the cDNA coding the TCR Valpha and Vbeta chains were joined with mouse Calpha and Cbeta, respectively, and linked together using the 2A peptide. In the lentivector, the chimeric TCRs genes are followed by an IRES sequence to allow the transcription of the eGFP reporter marker. The GFP gene can be excised by a simple digestion in order to obtain the same constructs devoid of the fluorescent marker.

To verify whether the cloned TCRs could be expressed on the surface of T cells, each construct has been transduced into Jurkat 76 cells, which is a T-cell acute leukemia cell line that does not express the endogenous TCR, but allows the membrane expression of any exogenous TCR. Moreover, the TCR-signaling machinery is intact, therefore Jurkat 76 cells can be utilized to investigate the antigen recognition by the exogenous TCRs. FIG. 3A shows the expression of transduced TCRs detected by mAb specific for mouse Cbeta. Four out of five TCRs are expressed well on the cell surface. Only the TCR cloned from the self-reactive T cell clone DN 7.6.16 is weakly expressed. In initial experiments, Jurkat 76 cells expressing the DN4.99 and CD4P8E3 TCRs were also challenged with THP1-CD1c cells, in the absence or in the presence of the synthetic lipid antigen mLPA. As shown in FIG. 3B, upon recognition of CD1c$^+$ THP1 cells, transduced Jurkat 76 cells upregulate the activation marker CD69, which is an indicator of TCR signaling. The upregulation of CD69 by the TCR-transduced Jurkat 76 cells is further enhanced by the addition of mLPA to the assay, confirming the antigen specificity of the two clones TCRs.

Example 2

Identification of the Lead CD1c-Restricted TCR to Engineer T Cells for Adoptive Immunotherapy The inventors have cloned into lentiviral vectors five different mLPA-specific TCRs from five independent CD1c self-reactive T cell clones bearing seemingly different affinities. To assess expression and relative Ag-affinities of these TCRs, the inventors transduced them into Jurkat 76 cells and tested their ability to recognize leukemia target cells by analyzing CD69 upregulation on the cell surface. As shown in FIG. 3A, the 5 TCRs are expressed at variable level: 4 out of 5 (TCR DN4.99, DN4.2, PZ-P8A6 and P8E3) are well expressed; one (TCR DN7.6.16) is retained inside the Jurkat 76 cells (data not shown)

Further, 3 out of the 4 expressed TCRs (TCR DN4.99, DN4.2, PZ-P8A6) recognize the K562 acute myeloid leukemia cell line expressing CD1c and the recognition is further increased by the addition of synthetic mLPA antigen to the target cells (FIG. 3B). These data confirm the lipid Ag-specificity of the TCRs of the present invention.

The inventors noticed that Jurkat 76 cells express CD1c and reasoned that this might result in a "tonic" stimulation of the Jurkat 76 cells transduced with the mLPA-specific TCRs, increasing their threshold of responsiveness to subsequent Ag stimulation and ultimately impacting their functional response. To avoid this confounding factor, the inventors hence generated Jurkat 76 cells devoid of all CD1 surface expression by deleting β2m gene with CRISP/Cas9 technology. Jurkat 76 cells wee electroporated with a plasmid encoding Cas9 recombinase together with guide RNA targeting β2m gene. After 45 days, electroporated cells that lost MHC class I expression were isolated by cell sorting and further cultured until day 85, when CD1c was also found downregulated from the cell surface) Jurkat 76 β2m$^-$ cells were transduced with the 5 CD1c self reactive TCRs, obtaining surface expression similar to those displayed by Jurkat 76 cells (FIG. 4A), and challenged with the leukemia cell line K562-CD1c with or without mLPA. As shown in FIG. 4B, TCR-transduced Jurkat 76 β2m$^-$ cells displayed a comparable pattern of recognition observed with Jurkat 76 cells, although with a markedly increased CD69 RFI suggesting a much increased Ag responsiveness despite overall similar surface TCR expression compared to Jurkat 76 cells.

Jurkat 76 β2m$^-$ cells expressing the TCR DN4.99, TCR DN4.2 and TCR PZP8A6 were challenged with mLPA lipid titration to assess the affinity of the transduced TCRs.

The level of expression of the transduced TCRs on the very same Jurkat cells utilized for the antigen recognition is shown in FIG. 5A.

This assay provides Ag affinities independent of the surface expression of tested TCR. As shown in FIG. 5B, TCR DN4.99 displayed the highest TCR affinity (EC50=100 ng/ul), suggesting that this could represent the lead TCR to arm T cells for adoptive immunotherapy protocols.

To confirm that large amount of T cells expressing the transduced mLPA-specific TCRs can be generated, viruses coding for TCR DN4.99, TCR DN4.2 and TCR PZP8A6 were transduced into polyclonal T cells isolated from the peripheral blood of healthy donors. As shown in FIG. 6A, more than 60% of T cells express the transduced chimeric TCR. Furthermore, T cells engineered with each of the three mLPA-specific TCRs specifically recognized two different AML cell lines (THP1, K562) expressing CD1c (FIG. 6B).

This supports the feasibility of the approach to retarget large numbers of T cells against CD1c-expressing leukemia cells by the transduction of mLPA-specific TCRs.

The inventors also assessed whether both major CD4$^+$ and CD8$^+$ T cell subsets expressing the transduced mLPA-specific TCRs recognized CD1c-expressing AML cell cell lines. Indeed, either TCR-transduced CD4$^+$ or CD8$^+$ T cells specifically recognized (FIGS. 7A-B) and killed THP1-CD1c$^+$ leukemia cells, as shown by the disappearance of CD33+ cells after overnight of co-culture with transduced T cells (FIG. 7C-D).

The transfer of mLPA-specific TCR into primary polyclonal CD4+ and CD8+ T cells generates effector cells that can kill a CD1c-expressing leukemia cell line, which is the pre-requisite for their clinical use.

Example 3

Assessing the Anti-Leukemia Efficacy of T Cells Engineered with the Lead mLPA-Specific TCR DN4.99

The inventors first tested whether total primary T cells engineered with the lead TCR DN4.99 killed also primary blasts freshly isolated from an AML patient. As shown in FIG. 8, TCR DN 4.99 transduced T cells, and not mock transduced one, specifically killed primary AML blasts supporting the potential efficacy of this strategy.

FIG. 8A confirms that primary AML blasts express CD1c, making them targettable by mLPA-specific T cells. FIG. 8B shows that the transfer of mLPA-specific TCR into primary polyclonal cells generates effector T cells that can kill the primary CD1c-expressing leukemia blast, which is the ultimate target for the therapeutic application of these TCRs.

Currently, it is envisaged to apply adoptive cell therapy with leukemia-specific T cells at disease relapse after stem cell transplantation or induction chemotherapy. This could rescue relapsing patients. In this therapeutic scenario, one crucial point to be verified for the proposed leukemia targeting by CD1c self reactive T cells is the expression of CD1c on relapsed leukemia blasts and their recognition by mLPA-specific T cells. To address this critical issue, freshly isolated leukemia blasts were assessed for CD1c expression and for their ability to activate the DN4.99 mLPA-specific T cells both at diagnosis and at post-transplant relapse. FIG. 9 shows representative results.

The expression of CD1c on primary blasts at diagnosis is maintained at prost-transplant relapse and both primary and relapsed leukemia cells are recognized at similar extent by mLPA-specific T cells.

Collectively, the results shown in FIGS. 9A and B support the application of adoptive cell therapy with redirected mLPA-specific T cells at disease relapse after stem cell transplantation or induction chemotherapy.

Example 4

Assessing the Safety of T Cells Engineered with the Lead mLPA-Specific TCR DN4.99

The inventors are also assessing the safety of the adoptive cell therapy approach with T cells engineered with the lead mLPA-specific TCR DN4.99. The main issue is to rule out possible detrimental on-target off-tumor recognition by the transduced T cells. mLPA is highly enriched in leukemia cells and in primary activated dendritic cells derived from circulating monocytes by culture with GM-CSF and IL-4, whereas it is very low in circulating monocytes and B cells at steady state. In principle, this Ag expression pattern should selectively target the reactivity of T cells engineered with the lead mLPA-specific TCR DN4.99 against the leukemia cells and a selected subset of normal mature DCs.

Moreover, CD1c expression is absent in hematopoietic precursors (Lepore, de Lalla et al J Exp Med 2014 Lepore M, de Lalla C, Gundimeda S R, Gsellinger H, Consonni M, Garavaglia C, Sansano S, Piccolo F, Scelfo A, Hiussinger D, Montagna D, Locatelli F, Bonini C, Bondanza A, Forcina A, Li Z, Ni G, Ciceri F, Jen6 P, Xia C, Mori L, Dellabona P, Casorati G, De Libero G. A novel self-lipid antigen targets human T cells against CD1c+ leukemias. J Exp Med. 2014 Jun. 30; 211(7):1363-77), ruling out the recognition of essential cells for the maintenance of normal hematopoiesis. However, as a further measure to assess safety in vitro, the inventors have investigated a possible cross-reactivity of the lead mLPA-specific TCR DN4.99 with common and abundant phospholipids that share structural features with mLPA and may trigger off-tumor T cell recognition. Phosphatidilserine (PS) is a component of all cells and blood platelet membranes, while lysophosphatidylethanolamine (LPE) is a phospholipid found at high concentration in circulation as well as in biological membranes (FIG. 10).

As shown in FIG. 11, Jurkat 76 cells expressing the mLPA-specific TCRs DN4.99 (A) or TCR DN4.2 (B) did not recognize PS and three different LPE species. By contrast, cells were activated by mLPA, as suggested by the up regulation of CD69 expression on TCR transduced Jurkat 76 cells upon co-culture with lipid-loaded K562-CD1c cells.

This supports the safety of the adoptive cell therapy with T cells engineered with mLPA-specific TCRs, because they will selectively recognize the leukemia-enriched mLPA antigen, and not the other widely distributed and abundant phospholipids with analog structures.

The ability of the TCR transduced T cells to control leukemia cells in NSG mice is also assessed. CD1c-expressing acute leukemia cell lines or primary blasts are transplanted into immunodeficient NSG mice, followed by the transfer of polyclonal allogeneic and, also patient-autologous T cells transduced or not transduced with the mLPA-specific TCRs. To follow leukemia progression in vivo, the inventors have generated THP-1 cells expressing the luciferase with or without CD1c (data not shown). Progression of the primary leukemia is monitored by flowcytometry on blood samples.

The invention claimed is:

1. An isolated or purified T-cell receptor (TCR) having antigenic specificity for a self-lipid associated to CD1c molecule, wherein the self-lipid is a methyl-lysophosphatidic acid or derivative thereof wherein the TCR is in monomeric form and comprises:
a complementary determining region (CDRa1) amino acid sequence of SEQ. ID NO: 25; and
a complementary determining region (CDRa2) amino acid sequence of SEQ. ID NO: 26; and
a complementary determining region (CDRa3) amino acid sequence of SEQ. ID NO: 27; and
a complementary determining region (CDRb1) amino acid sequence of SEQ. ID NO: 28; and
a complementary determining regions (CDRb2) amino acid sequence of SEQ. ID NO: 29; and
complementary determining regions (CDRb3) amino acid sequence of SEQ. ID NO: 30.

2. The isolated or purified T-cell receptor (TCR) according to claim 1 wherein the methyl-lysophosphatidic acid is selected from the group consisting of: methyl-lysophosphatidic acid (mLPA), C16-methyl-lysophosphatidic acid (C16-mLPA) or C18-methyl-lysophosphatidic acid (C18-mLPA) or a derivative thereof.

3. An isolated or purified nucleic acid comprising a nucleotide sequence encoding the TCR as defined in claim 1.

4. The isolated or purified nucleic acid according to claim 3, wherein the nucleotide sequence comprises a) a nucleotide sequence of SEQ ID NOs: 15 and b) a nucleotide sequence of SEQ ID NOs: 16.

5. A recombinant expression vector comprising the nucleic acid according to claim 3.

6. An isolated host cell comprising the recombinant expression vector of claim 5.

7. A pharmaceutical composition comprising
a T cell comprising a recombinant expression vector including a nucleic acid encoding for a TCR
and a pharmaceutically acceptable carrier;
wherein the TCR has antigenic specificity for a self-lipid associated to CD1c molecule, wherein the self-lipid is a methyl-lysophosphatidic acid or derivative thereof;
wherein the TCR is in monomeric form and comprises;
a complementary determining region (CDRa1) amino acid sequence of SEQ. ID NO: 25; and
a complementary determining region (CDRa2) amino acid sequence of SEQ. ID NO: 26; and
a complementary determining region (CDRa3) amino acid sequence of SEQ. ID NO: 27; and
a complementary determining region (CDRb1) amino acid sequence of SEQ. ID NO: 28; and
a complementary determining regions (CDRb2) amino acid sequence of SEQ. ID NO: 29; and
complementary determining regions (CDRb3) amino acid sequence of SEQ. ID NO: 30.

8. The pharmaceutical composition according to claim 7 further comprising methyl lysophosphatidic acid (mLPA).

9. A method of treating a hematological disorder in a subject, the method comprising administering the pharmaceutical composition of claim 7, wherein the hematological disorder is characterized by mLPA+ CD1c+ cancer cells.

10. The method of claim 9 wherein the hematological disorder is characterized by blood and bone marrow accumulation of immature and abnormal cells derived from hematopoietic precursors.

11. The method of claim 9, wherein the hematological disorder is acute leukemia.

12. The method of claim 9, further comprising administering at least one of asparaginase, busulfan, carboplatin, cisplatin, daunorubicin, doxorubicin, fluorouracil, gemcitabine, hydroxyurea, methotrexate, paclitaxel, rituximab, vinblastine, vincristine, and/or azacytidine.

13. The method of claim 9, wherein the method further comprises preventing hematological disorder relapse following hematopoietic stem cell transplantation (HSCT).

14. The method of claim 9, wherein the pharmaceutical composition further comprises methyl lysophosphatidic acid (mLPA).

15. A method for the production of a host cell as defined in claim 6 comprising the step of transducing said host cell with a nucleic acid encoding for a TCR in monomeric form, wherein the TCR comprises:
a complementary determining region (CDRa1) amino acid sequence of SEQ. ID NO: 25; and
a complementary determining region (CDRa2) amino acid sequence of SEQ. ID NO: 26; and
a complementary determining region (CDRa3) amino acid sequence of SEQ. ID NO: 27; and
a complementary determining region (CDRb1) amino acid sequence of SEQ. ID NO: 28; and
a complementary determining regions (CDRb2) amino acid sequence of SEQ. ID NO: 29; and
complementary determining regions (CDRb3) amino acid sequence of SEQ. ID NO: 30.

16. The method according to claim 15 further comprising expanding said host cell.

17. The isolated or purified nucleic acid according to claim 3, wherein the nucleotide sequence is codon optimized.

18. The isolated or purified T-cell receptor (TCR) according to claim 1, wherein the TCR further comprises a murine, a human or a humanized amino acid sequence of a constant region.

19. The isolated host cell according to claim 6, wherein the host cell is a T cell.

20. An isolated or purified T-cell receptor (TCR) having antigenic specificity for a self-lipid associated to CD1c molecule, wherein the self-lipid is a methyl-lysophosphatidic acid or derivative thereof, wherein the TCR is in monomeric form and comprises:
the amino acid sequence of SEQ ID NO: 1; and
the amino acid sequence of SEQ ID NO: 2.

21. An isolated or purified T-cell receptor (TCR) having antigenic specificity for a self-lipid associated to CD1c molecule, wherein the self-lipid is a methyl-lysophosphatidic acid or derivative thereof, wherein the TCR is in monomeric form and comprises:
the amino acid sequence of SEQ ID NO: 1; and
the amino acid sequence of SEQ ID No: 2, and
wherein the TCR further comprises a murine, a human or a humanized amino acid sequence of a constant region.

22. The method of claim 11 wherein the acute leukemia is primary acute myeloid leukemia or B-cell acute leukemia.

23. The method according to claim 16 wherein said host cell is expanded in the presence of methyl lysophosphatidic acid (mLPA).

24. The isolated or purified T-cell receptor (TCR) according to claim 18, wherein the murine, human or humanized amino acid sequence of the constant region comprises:
the amino acid sequence of SEQ ID NO: 11;
the amino acid sequence of SEQ ID NO: 12; or
the amino acid sequence of SEQ ID NO: 13; or
the amino acid sequence of SEQ ID NO: 14.

25. The isolated or purified T-cell receptor (TCR) according to claim 21, wherein the murine, human or humanized amino acid sequence of the constant region comprises:
the amino acid sequence of SEQ ID NO: 11;
the amino acid sequence of SEQ ID NO: 12; or
the amino acid sequence of SEQ ID NO: 13; or
the amino acid sequence of SEQ ID NO: 14.

* * * * *

SEQUENCE LISTING

<160> NUMBER OF SEQ ID NOS: 61

<210> SEQ ID NO 1
<211> LENGTH: 138
<212> TYPE: PRT
<213> ORGANISM: Artificial Sequence
<220> FEATURE:
<223> OTHER INFORMATION: synthetic

<400> SEQUENCE: 1

```
Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80
```

```
Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Arg Ser Pro Leu Asn Thr Gly Thr Ala Ser Leu Thr Phe
        115                 120                 125

Gly Thr Gly Thr Arg Leu Gln Val Thr Leu
        130                 135

<210> SEQ ID NO 2
<211> LENGTH: 138
<212> TYPE: PRT
<213> ORGANISM: Artificial Sequence
<220> FEATURE:
<223> OTHER INFORMATION: synthetic

<400> SEQUENCE: 2

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Cys
    50                  55                  60

Asp Arg Cys Asp Arg Leu Ile Tyr Phe Ser Tyr Asp Val Lys Met Lys
65                  70                  75                  80

Glu Lys Gly Asp Ile Pro Glu Gly Tyr Ser Val Ser Arg Glu Lys Lys
                85                  90                  95

Glu Arg Phe Ser Leu Ile Leu Glu Ser Ala Ser Thr Asn Gln Thr Ser
            100                 105                 110

Met Tyr Leu Cys Ala Ser Ser Pro Trp Val Ser Ser Tyr Glu Gln Tyr
        115                 120                 125

Phe Gly Pro Gly Thr Arg Leu Thr Val Thr
        130                 135

<210> SEQ ID NO 3
<211> LENGTH: 138
<212> TYPE: PRT
<213> ORGANISM: Artificial Sequence
<220> FEATURE:
<223> OTHER INFORMATION: synthetic

<400> SEQUENCE: 3

Met Thr Arg Val Ser Leu Leu Trp Ala Val Val Val Ser Thr Cys Leu
1               5                   10                  15

Glu Ser Gly Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Asn Asn Tyr Tyr Leu Phe Trp Tyr Lys Gln Pro Pro Ser Arg Cys
    50                  55                  60

Asp Arg Cys Asp Arg Gln Met Ile Leu Val Ile Arg Gln Glu Ala Tyr
65                  70                  75                  80

Lys Gln Gln Asn Ala Thr Glu Asn Arg Phe Ser Val Asn Phe Gln Lys
                85                  90                  95
```

```
Ala Ala Lys Ser Phe Ser Leu Lys Ile Ser Asp Ser Gln Leu Gly Asp
                100                 105                 110

Thr Ala Met Tyr Phe Cys Ala Phe Ala Asn Asn Ala Arg Leu Met Phe
            115                 120                 125

Gly Asp Gly Thr Gln Leu Val Val Lys Pro
130                 135

<210> SEQ ID NO 4
<211> LENGTH: 137
<212> TYPE: PRT
<213> ORGANISM: Artificial Sequence
<220> FEATURE:
<223> OTHER INFORMATION: synthetic

<400> SEQUENCE: 4

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Cys
    50                  55                  60

Asp Arg Cys Asp Arg Leu Ile Tyr Phe Ser Tyr Asp Val Lys Met Lys
65                  70                  75                  80

Glu Lys Gly Asp Ile Pro Glu Gly Tyr Ser Val Ser Arg Glu Lys Lys
                85                  90                  95

Glu Arg Phe Ser Leu Ile Leu Glu Ser Ala Ser Thr Asn Gln Thr Ser
                100                 105                 110

Met Tyr Leu Cys Ala Ser Thr Asp Thr Gly Asn Thr Glu Ala Phe Phe
            115                 120                 125

Gly Gln Gly Thr Arg Leu Thr Val Val
        130                 135

<210> SEQ ID NO 5
<211> LENGTH: 135
<212> TYPE: PRT
<213> ORGANISM: Artificial Sequence
<220> FEATURE:
<223> OTHER INFORMATION: synthetic

<400> SEQUENCE: 5

Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
            20                  25                  30

Glu Pro Val His Leu Pro Cys Asn His Ser Thr Ile Ser Gly Thr Asp
        35                  40                  45

Tyr Ile His Trp Tyr Arg Gln Leu Pro Ser Gln Gly Pro Glu Tyr Val
    50                  55                  60

Ile Cys Asp Arg Cys Asp Arg His Gly Leu Thr Ser Asn Val Asn Asn
65                  70                  75                  80

Arg Met Ala Ser Leu Ala Ile Ala Glu Asp Arg Lys Ser Ser Thr Leu
                85                  90                  95

Ile Leu His Arg Ala Thr Leu Arg Asp Ala Ala Val Tyr Tyr Cys Ile
                100                 105                 110
```

```
Leu Arg Leu Arg Gly Gly Ser Asn Tyr Lys Leu Thr Phe Gly Lys Gly
        115                 120                 125

Thr Leu Leu Thr Val Asn Pro
    130                 135

<210> SEQ ID NO 6
<211> LENGTH: 142
<212> TYPE: PRT
<213> ORGANISM: Artificial Sequence
<220> FEATURE:
<223> OTHER INFORMATION: synthetic

<400> SEQUENCE: 6

Met Gly Cys Arg Leu Leu Cys Cys Ala Val Leu Cys Leu Leu Gly Ala
1               5                   10                  15

Gly Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Cys Asp
    50                  55                  60

Arg Cys Asp Arg Glu Leu Met Phe Val Tyr Ser Tyr Glu Lys Leu Ser
65                  70                  75                  80

Ile Asn Glu Ser Val Pro Ser Arg Phe Ser Pro Glu Cys Pro Asn Ser
                85                  90                  95

Ser Leu Leu Asn Leu His Leu His Ala Leu Gln Pro Glu Asp Ser Ala
            100                 105                 110

Leu Tyr Leu Cys Ala Ser Ser Pro Ile Met Gly Leu Ala Ala Thr His
        115                 120                 125

Asn Glu Gln Phe Phe Gly Pro Gly Thr Arg Leu Thr Val Leu
    130                 135                 140

<210> SEQ ID NO 7
<211> LENGTH: 137
<212> TYPE: PRT
<213> ORGANISM: Artificial Sequence
<220> FEATURE:
<223> OTHER INFORMATION: synthetic

<400> SEQUENCE: 7

Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
            20                  25                  30

Glu Pro Val His Leu Pro Cys Asn His Ser Thr Ile Ser Gly Thr Asp
        35                  40                  45

Tyr Ile His Trp Tyr Arg Gln Leu Pro Ser Gln Gly Pro Glu Tyr Val
    50                  55                  60

Ile Cys Asp Arg Cys Asp Arg His Gly Leu Thr Ser Asn Val Asn Asn
65                  70                  75                  80

Arg Met Ala Ser Leu Ala Ile Ala Glu Asp Arg Lys Ser Ser Thr Leu
                85                  90                  95

Ile Leu His Arg Ala Thr Leu Arg Asp Ala Ala Val Tyr Tyr Cys Ile
            100                 105                 110

Leu Arg Asp Val Asn Thr Gly Thr Ala Ser Lys Leu Thr Phe Gly Thr
        115                 120                 125
```

```
Gly Thr Arg Leu Gln Val Thr Leu Asp
        130                 135

<210> SEQ ID NO 8
<211> LENGTH: 139
<212> TYPE: PRT
<213> ORGANISM: Artificial Sequence
<220> FEATURE:
<223> OTHER INFORMATION: synthetic

<400> SEQUENCE: 8

Met Gly Cys Arg Leu Leu Cys Cys Ala Val Leu Cys Leu Leu Gly Ala
1               5                   10                  15

Gly Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Cys Asp
50                  55                  60

Arg Cys Asp Arg Glu Leu Met Phe Val Tyr Ser Tyr Glu Lys Leu Ser
65                  70                  75                  80

Ile Asn Glu Ser Val Pro Ser Arg Phe Ser Pro Glu Cys Pro Asn Ser
                85                  90                  95

Ser Leu Leu Asn Leu His Leu His Ala Leu Gln Pro Gly Asp Ser Ala
            100                 105                 110

Leu Tyr Leu Cys Ala Ser Ser Arg Leu Gly Leu Ser Thr Asp Thr Gln
        115                 120                 125

Tyr Phe Gly Pro Gly Thr Arg Leu Thr Val Leu
        130                 135

<210> SEQ ID NO 9
<211> LENGTH: 139
<212> TYPE: PRT
<213> ORGANISM: Artificial Sequence
<220> FEATURE:
<223> OTHER INFORMATION: synthetic

<400> SEQUENCE: 9

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
50                  55                  60

Leu Cys Asp Arg Cys Asp Arg Ile Ile Asp Ile Arg Ser Asn Val Gly
65                  70                  75                  80

Glu Lys Lys Asp Gln Arg Ile Ala Val Thr Leu Asn Lys Thr Ala Lys
                85                  90                  95

His Phe Ser Leu His Ile Thr Glu Thr Gln Pro Glu Asp Ser Ala Val
            100                 105                 110

Tyr Phe Cys Ala Ala Pro Arg Gly Leu Gly Val Thr Asn Ser Leu Ser
        115                 120                 125

Gly Arg Gly Pro Asn Ser Arg Ser Tyr Gln Asn
        130                 135
```

```
<210> SEQ ID NO 10
<211> LENGTH: 139
<212> TYPE: PRT
<213> ORGANISM: Artificial Sequence
<220> FEATURE:
<223> OTHER INFORMATION: synthetic

<400> SEQUENCE: 10

Met Gly Pro Gln Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
                20                  25                  30

Val Thr Gly Lys Lys Leu Thr Val Thr Cys Ser Gln Asn Met Asn His
            35                  40                  45

Glu Tyr Met Ser Trp Tyr Arg Gln Asp Pro Gly Leu Gly Leu Arg Cys
        50                  55                  60

Asp Arg Cys Asp Arg Gln Ile Tyr Tyr Ser Met Asn Val Glu Val Thr
65                  70                  75                  80

Asp Lys Gly Asp Val Pro Glu Gly Tyr Lys Val Ser Arg Lys Glu Lys
                85                  90                  95

Arg Asn Phe Pro Leu Ile Leu Glu Ser Pro Ser Pro Asn Gln Thr Ser
                100                 105                 110

Leu Tyr Phe Cys Ala Ser Ser Leu Val Trp Gly Thr Tyr Asn Glu Gln
            115                 120                 125

Phe Phe Gly Pro Gly Thr Arg Leu Thr Val Leu
        130                 135

<210> SEQ ID NO 11
<211> LENGTH: 137
<212> TYPE: PRT
<213> ORGANISM: Artificial Sequence
<220> FEATURE:
<223> OTHER INFORMATION: synthetic

<400> SEQUENCE: 11

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
                20                  25                  30

Asn Val Pro Lys Thr Met Glu Ser Gly Thr Phe Ile Thr Asp Lys Thr
            35                  40                  45

Val Leu Asp Met Lys Ala Met Asp Ser Lys Ser Asn Gly Ala Ile Ala
        50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
                100                 105                 110

Val Met Gly Leu Arg Ile Leu Leu Lys Val Ala Gly Phe Asn Leu
            115                 120                 125

Leu Met Thr Leu Arg Leu Trp Ser Ser
        130                 135

<210> SEQ ID NO 12
<211> LENGTH: 173
<212> TYPE: PRT
<213> ORGANISM: Artificial Sequence
<220> FEATURE:
```

<223> OTHER INFORMATION: synthetic

<400> SEQUENCE: 12

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr His Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Gly Leu Val Leu Met Ala Met Val Lys Lys Lys Asn Ser
                165                 170

<210> SEQ ID NO 13
<211> LENGTH: 140
<212> TYPE: PRT
<213> ORGANISM: Artificial Sequence
<220> FEATURE:
<223> OTHER INFORMATION: synthetic

<400> SEQUENCE: 13

Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Thr Val
        35                  40                  45

Leu Asp Met Arg Ser Met Asp Phe Lys Ser Asn Ser Ala Val Ala Trp
    50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
    130                 135                 140

<210> SEQ ID NO 14
<211> LENGTH: 179
<212> TYPE: PRT
<213> ORGANISM: Artificial Sequence
<220> FEATURE:
<223> OTHER INFORMATION: synthetic

<400> SEQUENCE: 14

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 15
<211> LENGTH: 447
<212> TYPE: DNA
<213> ORGANISM: Artificial Sequence
<220> FEATURE:
<223> OTHER INFORMATION: synthetic

<400> SEQUENCE: 15
gaattcgccc ttctgcagca gggacctgtg agcatggcat gccctggctt cctgtgggca      60
cttgtgatct ccacctgtct tgaatttagc atggctcaga cagtcactca gtctcaacca     120
gagatgtctg tgcaggaggc agagaccgtg accctgagct gcacatatga ccaccagtgag    180 agtgattatt atttattctg gtacaagcag cctcccagca ggcagatgat tctcgttatt     240
cgccaagaag cttataagca acagaatgca acagagaatc gtttctctgt gaacttccag     300
aaaagcagcc aatccttcag tctcaagatc tcagactcac agctggggga tgccgcgatg     360
tatttctgtg cttataggag ccccttaaat accggcactg ccagtaaact caccttgggg     420
actggaacaa gacttcaggt cacgctc                                         447

<210> SEQ ID NO 16
<211> LENGTH: 402
<212> TYPE: DNA
<213> ORGANISM: Artificial Sequence
<220> FEATURE:
<223> OTHER INFORMATION: synthetic

<400> SEQUENCE: 16
cccaccatgg gaatcaggct cctctgtcgt gtggcctttt gtttcctggc tgtaggcctc      60
gtagatgtga agtaaccca gagctcgaga tatctagtca aaaggacggg agagaaagtt     120

```
tttctggaat gtgtccagga tatggaccat gaaaatatgt tctggtatcg acaagaccca    180
ggtctggggc tacggctgat ctatttctca tatgatgtta aatgaaaga aaaggagat     240 attcctgagg ggtacagtgt ctctagagag aagaaggagc gcttctccct gattctggag   300
tccgccagca ccaaccagac atctatgtac ctctgtgcca gcagtccatg ggtaagctcc   360
tacgagcagt acttcgggcc gggcaccagg ctcacggtca ca                      402

<210> SEQ ID NO 17
<211> LENGTH: 396
<212> TYPE: DNA
<213> ORGANISM: Artificial Sequence
<220> FEATURE:
<223> OTHER INFORMATION: synthetic

<400> SEQUENCE: 17
atgacacgag ttagcttgct gtgggcagtc gtggtctcca cctgtcttga atccggcatg    60
gcccagacag tcactcagtc tcaaccagag atgtctgtgc aggaggcaga gactgtgacc   120
ctgagttgca catatgacac cagtgagaat aattattatt tgttctggta caagcagcct   180
cccagcaggc agatgattct cgttattcgc caagaagctt ataagcaaca gaatgcaacg   240
gagaatcgtt tctctgtgaa cttccagaaa gcagccaaat ccttcagtct caagatctca   300
gactcacagc tgggggacac tgcgatgtat ttctgtgctt cgcaaacaa tgccagactc    360 atgtttggag atggaactca gctggtggtg aagccc                             396

<210> SEQ ID NO 18
<211> LENGTH: 438
<212> TYPE: DNA
<213> ORGANISM: Artificial Sequence
<220> FEATURE:
<223> OTHER INFORMATION: synthetic

<400> SEQUENCE: 18
actgcctggt cctgggagaa gacctattct ttcttcaaag cagccatggg aatcaggctc    60
ctctgtcgtg tggccttttg tttcctggct gtaggcctcg tagatgtgaa agtaacccag   120
agctcgagat atcagtcaa aaggacggga gagaaagttt ttctggaatg tgtccaggat    180
atggaccatg aaaatatgtt ctggtatcga caagacccag gtctggggct acggctgatc   240
tatttctcat atgatgttaa aatgaaagaa aaggagata ttcctgaggg gtacagtgtc    300
tctagagaga agaaggagcg cttctccctg attctggagt ccgccagcac caaccagaca   360
tctatgtacc tctgtgccag caccgacact gggaacactg aagctttctt tggacaaggc   420
accagactca cagttgta                                                 438

<210> SEQ ID NO 19
<211> LENGTH: 435
<212> TYPE: DNA
<213> ORGANISM: Artificial Sequence
<220> FEATURE:
<223> OTHER INFORMATION: synthetic

<400> SEQUENCE: 19
cacagagtct gagttctggg gcctggaacc tcaatgtgca cttgaacaat gaagttggtg    60
acaagcatta ctgtactcct atctttgggt attatgggtg atgctaagac cacacagcca   120
aattcaatgg agagtaacga agaagagcct gttcacttgc cttgtaacca ctccacaatc   180
agtggaactg attacataca ttggtatcga cagcttcccc cccagggtcc agagtacgtg   240
```

| | |
|---|---|
| attcatggtc ttacaagcaa tgtgaacaac agaatggcct ctctggcaat cgctgaagac | 300 |
| agaaagtcca gtaccttgat cctgcaccgt gctaccttga gagatgctgc tgtgtactac | 360 |
| tgcatcctga gattaagagg aggtagcaac tataaactga catttggaaa aggaactctc | 420 |
| ttaaccgtga atcca | 435 |

<210> SEQ ID NO 20
<211> LENGTH: 408
<212> TYPE: DNA
<213> ORGANISM: Artificial Sequence
<220> FEATURE:
<223> OTHER INFORMATION: synthetic

<400> SEQUENCE: 20

| | |
|---|---|
| atgggctgca ggctgctctg ctgtgcggtt ctctgtctcc tgggagcagg tcccatagac | 60 |
| actgaagtta cccagacacc aaaacacctg gtcatgggaa tgacaaataa gaagtctttg | 120 |
| aaatgtgaac aacatatggg gcacagggct atgtattggt acaagcagaa agctaagaag | 180 |
| ccaccggagc tcatgtttgt ctacagctat gagaaactct ctataaatga agtgtgcca | 240 |
| agtcgcttct cacctgaatg ccccaacagc tctctcttaa accttcacct acacgccctg | 300 |
| cagccagaag actcagccct gtatctctgc gccagcagcc aatcatggg actagcggcg | 360 |
| acccacaatg agcagttctt cgggccaggg acacggctca ccgtgcta | 408 |

<210> SEQ ID NO 21
<211> LENGTH: 393
<212> TYPE: DNA
<213> ORGANISM: Artificial Sequence
<220> FEATURE:
<223> OTHER INFORMATION: synthetic

<400> SEQUENCE: 21

| | |
|---|---|
| atgaagttgg tgacaagcat tactgtactc ctatctttgg gtattatggg tgatgctaag | 60 |
| accacacagc caaattcaat ggagagtaac gaagaagagc ctgttcactt gccttgtaac | 120 |
| cactccacaa tcagtggaac tgattacata cattggtatc gacagcttca ctcccagggt | 180 |
| ccagagtacg tgattcatgg tcttacaagc aatgtgaaca acagaatggc ctctctggca | 240 |
| atcgctgaag acagaaagtc cagtaccttg atcctgcacc gtgctacctt gagagatgct | 300 |
| gctgtgtact actgcatcct gagagacgta ataccggca ctgccagtaa actcaccttt | 360 |
| gggactggaa caagacttca ggtcacgctc gat | 393 |

<210> SEQ ID NO 22
<211> LENGTH: 399
<212> TYPE: DNA
<213> ORGANISM: Artificial Sequence
<220> FEATURE:
<223> OTHER INFORMATION: synthetic

<400> SEQUENCE: 22

| | |
|---|---|
| atgggctgca ggctgctctg ctgtgcggtt ctctgtctcc tgggagcagg tcccatagac | 60 |
| actgaagtta cccagacacc aaaacacctg gtcatgggaa tgacaaataa gaagtctttg | 120 |
| aaatgtgaac aacatatggg gcacagggct atgtattggt acaagcagaa agctaagaag | 180 |
| ccaccggagc tcatgtttgt ctacagctat gagaaactct ctataaatga agtgtgcca | 240 |
| agtcgcttct cacctgaatg ccccaacagc tctctcttaa accttcacct acacgccctg | 300 |
| cagccagaag actcagccct gtatctctgc gccagcagcc ggctaggact atccacggat | 360 |
| acgcagtatt ttggcccagg cacccggctg acagtgctc | 399 |

<210> SEQ ID NO 23
<211> LENGTH: 399
<212> TYPE: DNA
<213> ORGANISM: Artificial Sequence
<220> FEATURE:
<223> OTHER INFORMATION: synthetic

<400> SEQUENCE: 23

```
atgacatcca ttcgagctgt atttatattc ctgtggctgc agctggactt ggtgaatgga      60
gagaatgtgg agcagcatcc ttcaaccctg agtgtccagg agggagacag cgctgttatc     120
aagtgtactt attcagacag tgcctcaaac tacttccctt ggtataagca agaacttgga     180
aaaggacctc agcttattat agacattcgt tcaaatgtgg gcgaaaagaa agaccaacga     240
attgctgtta cattgaacaa gacagccaaa catttctccc tgcacatcac agagacccaa     300
cctgaagact cggctgtcta cttctgtgca gccccccgcg ggctgggagt taccaactca     360
ctttcgggaa ggggaccaaa ctctcggtca taccaaaat                            399
```

<210> SEQ ID NO 24
<211> LENGTH: 396
<212> TYPE: DNA
<213> ORGANISM: Artificial Sequence
<220> FEATURE:
<223> OTHER INFORMATION: synthetic

<400> SEQUENCE: 24

```
atgccccagc tccttggcta tgtggtcctt tgccttctag gagcaggccc cctggaagcc      60
caagtgaccc agaacccaag atacctcatc acagtgactg aaagaagtt aacagtgact     120
tgttctcaga atatgaacca tgagtatatg tcctggtatc gacaagaccc agggctgggc     180
ttaaggcaga tatactattc aatgaatgtt gaggtgactg ataagggaga tgttcctgaa     240
gggtacaaag tctctcgaaa agagaagagg aatttccccc tgatcctgga gtcgcccagc     300
cccaaccaga cctctctgta cttctgtgcc agcagtttgg tctggggaac ctacaatgag     360
cagttcttcg ggccagggac acggctcacc gtgcta                               396
```

<210> SEQ ID NO 25
<211> LENGTH: 9
<212> TYPE: PRT
<213> ORGANISM: Artificial Sequence
<220> FEATURE:
<223> OTHER INFORMATION: synthetic

<400> SEQUENCE: 25

Tyr Asp Thr Ser Glu Ser Asp Tyr Tyr
1               5

<210> SEQ ID NO 26
<211> LENGTH: 6
<212> TYPE: PRT
<213> ORGANISM: Artificial Sequence
<220> FEATURE:
<223> OTHER INFORMATION: synthetic

<400> SEQUENCE: 26

Arg Gln Glu Ala Tyr Lys
1               5

<210> SEQ ID NO 27
<211> LENGTH: 13
<212> TYPE: PRT

<213> ORGANISM: Artificial Sequence
<220> FEATURE:
<223> OTHER INFORMATION: synthetic

<400> SEQUENCE: 27

Arg Ser Pro Leu Asn Thr Gly Thr Ala Ser Lys Leu Thr
1               5                   10

<210> SEQ ID NO 28
<211> LENGTH: 9
<212> TYPE: PRT
<213> ORGANISM: Artificial Sequence
<220> FEATURE:
<223> OTHER INFORMATION: synthetic

<400> SEQUENCE: 28

Gln Asp Met Asp His Glu Asn Met Phe
1               5

<210> SEQ ID NO 29
<211> LENGTH: 7
<212> TYPE: PRT
<213> ORGANISM: Artificial Sequence
<220> FEATURE:
<223> OTHER INFORMATION: synthetic

<400> SEQUENCE: 29

Ser Tyr Asp Val Lys Met Lys
1               5

<210> SEQ ID NO 30
<211> LENGTH: 10
<212> TYPE: PRT
<213> ORGANISM: Artificial Sequence
<220> FEATURE:
<223> OTHER INFORMATION: synthetic

<400> SEQUENCE: 30

Ser Pro Trp Val Ser Ser Tyr Glu Gln Tyr
1               5                   10

<210> SEQ ID NO 31
<211> LENGTH: 9
<212> TYPE: PRT
<213> ORGANISM: Artificial Sequence
<220> FEATURE:
<223> OTHER INFORMATION: synthetic

<400> SEQUENCE: 31

Tyr Asp Thr Ser Glu Asn Asn Tyr Tyr
1               5

<210> SEQ ID NO 32
<211> LENGTH: 6
<212> TYPE: PRT
<213> ORGANISM: Artificial Sequence
<220> FEATURE:
<223> OTHER INFORMATION: synthetic

<400> SEQUENCE: 32

Arg Gln Glu Ala Tyr Lys
1               5

<210> SEQ ID NO 33
<211> LENGTH: 8
<212> TYPE: PRT
<213> ORGANISM: Artificial Sequence

```
<220> FEATURE:
<223> OTHER INFORMATION: synthetic

<400> SEQUENCE: 33

Phe Ala Asn Asn Ala Arg Leu Met
1               5

<210> SEQ ID NO 34
<211> LENGTH: 9
<212> TYPE: PRT
<213> ORGANISM: Artificial Sequence
<220> FEATURE:
<223> OTHER INFORMATION: synthetic

<400> SEQUENCE: 34

Gln Asp Met Asp His Glu Asn Met Phe
1               5

<210> SEQ ID NO 35
<211> LENGTH: 7
<212> TYPE: PRT
<213> ORGANISM: Artificial Sequence
<220> FEATURE:
<223> OTHER INFORMATION: synthetic

<400> SEQUENCE: 35

Ser Tyr Asp Val Lys Met Lys
1               5

<210> SEQ ID NO 36
<211> LENGTH: 9
<212> TYPE: PRT
<213> ORGANISM: Artificial Sequence
<220> FEATURE:
<223> OTHER INFORMATION: synthetic

<400> SEQUENCE: 36

Thr Asp Thr Gly Asn Thr Glu Ala Phe
1               5

<210> SEQ ID NO 37
<211> LENGTH: 9
<212> TYPE: PRT
<213> ORGANISM: Artificial Sequence
<220> FEATURE:
<223> OTHER INFORMATION: synthetic

<400> SEQUENCE: 37

His Ser Thr Ile Ser Gly Thr Asp Tyr
1               5

<210> SEQ ID NO 38
<211> LENGTH: 6
<212> TYPE: PRT
<213> ORGANISM: Artificial Sequence
<220> FEATURE:
<223> OTHER INFORMATION: synthetic

<400> SEQUENCE: 38

Gly Leu Thr Ser Asn Val
1               5

<210> SEQ ID NO 39
<211> LENGTH: 11
<212> TYPE: PRT
<213> ORGANISM: Artificial Sequence
<220> FEATURE:
```

<223> OTHER INFORMATION: synthetic

<400> SEQUENCE: 39

Arg Leu Arg Gly Gly Ser Asn Tyr Lys Leu Thr
1               5                   10

<210> SEQ ID NO 40
<211> LENGTH: 9
<212> TYPE: PRT
<213> ORGANISM: Artificial Sequence
<220> FEATURE:
<223> OTHER INFORMATION: synthetic

<400> SEQUENCE: 40

Gln His Met Gly His Arg Ala Met Tyr
1               5

<210> SEQ ID NO 41
<211> LENGTH: 7
<212> TYPE: PRT
<213> ORGANISM: Artificial Sequence
<220> FEATURE:
<223> OTHER INFORMATION: synthetic

<400> SEQUENCE: 41

Phe Val Tyr Ser Tyr Glu Lys
1               5

<210> SEQ ID NO 42
<211> LENGTH: 14
<212> TYPE: PRT
<213> ORGANISM: Artificial Sequence
<220> FEATURE:
<223> OTHER INFORMATION: synthetic

<400> SEQUENCE: 42

Ser Pro Ile Met Gly Leu Ala Ala Thr His Asn Glu Gln Phe
1               5                   10

<210> SEQ ID NO 43
<211> LENGTH: 10
<212> TYPE: PRT
<213> ORGANISM: Artificial Sequence
<220> FEATURE:
<223> OTHER INFORMATION: synthetic

<400> SEQUENCE: 43

His Ser Thr Ile Ser Gly Thr Asp Tyr Ile
1               5                   10

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

Gly Leu Thr Ser Asn Val
1               5

<210> SEQ ID NO 45
<211> LENGTH: 12
<212> TYPE: PRT
<213> ORGANISM: Artificial Sequence
<220> FEATURE:
<223> OTHER INFORMATION: synthetic

<400> SEQUENCE: 45

Arg Asp Val Asn Thr Gly Thr Ala Ser Lys Leu Thr
1               5                   10

<210> SEQ ID NO 46
<211> LENGTH: 9
<212> TYPE: PRT
<213> ORGANISM: Artificial Sequence
<220> FEATURE:
<223> OTHER INFORMATION: synthetic

<400> SEQUENCE: 46

Gln His Met Gly His Arg Ala Met Tyr
1               5

<210> SEQ ID NO 47
<211> LENGTH: 7
<212> TYPE: PRT
<213> ORGANISM: Artificial Sequence
<220> FEATURE:
<223> OTHER INFORMATION: synthetic

<400> SEQUENCE: 47

Phe Val Tyr Ser Tyr Glu Lys
1               5

<210> SEQ ID NO 48
<211> LENGTH: 11
<212> TYPE: PRT
<213> ORGANISM: Artificial Sequence
<220> FEATURE:
<223> OTHER INFORMATION: synthetic

<400> SEQUENCE: 48

Ser Arg Leu Gly Leu Ser Thr Asp Thr Gln Tyr
1               5                   10

<210> SEQ ID NO 49
<211> LENGTH: 9
<212> TYPE: PRT
<213> ORGANISM: Artificial Sequence
<220> FEATURE:
<223> OTHER INFORMATION: synthetic

<400> SEQUENCE: 49

Tyr Ser Asp Ser Ala Ser Asn Tyr Phe
1               5

<210> SEQ ID NO 50
<211> LENGTH: 6
<212> TYPE: PRT
<213> ORGANISM: Artificial Sequence
<220> FEATURE:
<223> OTHER INFORMATION: synthetic

<400> SEQUENCE: 50

Asp Ile Arg Ser Asn Val
1               5

<210> SEQ ID NO 51
<211> LENGTH: 10
<212> TYPE: PRT
<213> ORGANISM: Artificial Sequence
<220> FEATURE:
<223> OTHER INFORMATION: synthetic

<400> SEQUENCE: 51

Pro Arg Gly Leu Gly Val Thr Asn Ser Leu
1               5                   10

<210> SEQ ID NO 52
<211> LENGTH: 9
<212> TYPE: PRT
<213> ORGANISM: Artificial Sequence
<220> FEATURE:
<223> OTHER INFORMATION: synthetic

<400> SEQUENCE: 52

Gln Asn Met Asn His Glu Tyr Met Ser
1               5

<210> SEQ ID NO 53
<211> LENGTH: 6
<212> TYPE: PRT
<213> ORGANISM: Artificial Sequence
<220> FEATURE:
<223> OTHER INFORMATION: synthetic

<400> SEQUENCE: 53

Ser Met Asn Val Glu Val
1               5

<210> SEQ ID NO 54
<211> LENGTH: 11
<212> TYPE: PRT
<213> ORGANISM: Artificial Sequence
<220> FEATURE:
<223> OTHER INFORMATION: synthetic

<400> SEQUENCE: 54

Ser Leu Val Trp Gly Thr Tyr Asn Glu Gln Phe
1               5                   10

<210> SEQ ID NO 55
<211> LENGTH: 881
<212> TYPE: DNA
<213> ORGANISM: Artificial Sequence
<220> FEATURE:
<223> OTHER INFORMATION: synthetic

<400> SEQUENCE: 55

| | | | | | |
|---|---|---|---|---|---|
| gaattcgccc | ttctgcagca | gggacctgtg | agcatggcat | gccctggctt | cctgtgggca | 60 |
| cttgtgatct | ccacctgtct | tgaatttagc | atggctcaga | cagtcactca | gtctcaacca | 120 |
| gagatgtctg | tgcaggaggc | agagaccgtg | accctgagct | gcacatatga | caccagtgag | 180 |
| agtgattatt | atttattctg | gtacaagcag | cctcccagca | ggcagatgat | tctcgttatt | 240 |
| cgccaagaag | cttataagca | acagaatgca | acagagaatc | gtttctctgt | gaacttccag | 300 |
| aaagcagcca | aatccttcag | tctcaagatc | tcagactcac | agctggggga | tgccgcgatg | 360 |
| tatttctgtg | cttataggag | ccccttaaat | accggcactg | ccagtaaact | cacctttggg | 420 |
| actggaacaa | gacttcaggt | cacgctcgat | atccagaacc | cagaacctgc | tgtgtaccag | 480 |
| ttaaaagatc | tccggtctca | ggacagcacc | ctctgcctgt | tcaccgactt | tgactcccaa | 540 |
| atcaatgtgc | cgaaaaccat | ggaatctgga | acgttcatca | ctgacaaaac | tgtgctggac | 600 |
| atgaaagcta | tggattccaa | gagcaatggg | gccattgcct | ggagcaacca | gacaagcttc | 660 |
| acctgccaag | atatcttcaa | agagaccaac | gccacctacc | ccagttcaga | cgttccctgt | 720 |
| gatgccacgt | tgaccgagaa | aagctttgaa | acagatatga | acctaaactt | tcaaaacctg | 780 |

```
tcagttatgg gactccgaat cctcctgctg aaagtagcgg gatttaacct gctcatgacg      840
ctgaggctgt ggtccagttg aggatcccga agggcgaatt c                         881
```

<210> SEQ ID NO 56
<211> LENGTH: 927
<212> TYPE: DNA
<213> ORGANISM: Artificial Sequence
<220> FEATURE:
<223> OTHER INFORMATION: synthetic

<400> SEQUENCE: 56

```
cccaccatgg gaatcaggct cctctgtcgt gtggccttt gtttcctggc tgtaggcctc      60
gtagatgtga aagtaaccca gagctcgaga tatctagtca aaaggacggg agagaaagtt     120
tttctggaat gtgtccagga tatgaccat gaaaatatgt tctggtatcg acaagaccca     180
ggtctgggc tacggctgat ctatttctca tatgatgtta aaatgaaaga aaaggagat      240
attcctgagg ggtacagtgt ctctagagag aagaaggagc gcttctccct gattctggag     300
tccgccagca ccaaccagac atctatgtac ctctgtgcca gcagtccatg ggtaagctcc     360
tacgagcagt acttcgggcc gggcaccagg ctcacggtca cagaggatct gagaaatgtg     420
actccaccca aggtctcctt gtttgagcca tcaaaagcag agattgcaaa caacaaaag     480
gctaccctcg tgtgcttggc caggggcttc ttccctgacc acgtgagct gagctggtgg     540
gtgaatggca aggaggtcca cagtggggtc agcacggacc ctcaggccta caaggagagc     600
aattatagct actgcctgag cagccgcctg agggtctctg ctaccttctg gcacaatcct     660
cgaaaccact tccgctgcca agtgcagttc catgggcttt cagaggagga caagtggcca     720
gagggctcac ccaaacctgt cacacagaac atcagtgcag aggcctgggg ccgagcagac     780
tgtggaatca cttcagcatc ctatcatcag ggggttctgt ctgcaaccat cctctatgag     840
atcctactgg ggaaggccac ctatatgct gtgctggtca gtggcctggt gctgatggcc     900
atggtcaaga aaaaaattc ctgagac                                         927
```

<210> SEQ ID NO 57
<211> LENGTH: 18
<212> TYPE: PRT
<213> ORGANISM: Artificial Sequence
<220> FEATURE:
<223> OTHER INFORMATION: synthetic

<400> SEQUENCE: 57

Glu Gly Arg Gly Ser Leu Leu Thr Cys Gly Asp Val Glu Glu Asn Pro
1               5                   10                  15

Gly Pro

<210> SEQ ID NO 58
<211> LENGTH: 408
<212> TYPE: DNA
<213> ORGANISM: Artificial Sequence
<220> FEATURE:
<223> OTHER INFORMATION: synthetic

<400> SEQUENCE: 58

```
atccagaacc cagaacctgc tgtgtaccag ttaaagatc ctcggtctca ggacagcacc      60
ctctgcctgt tcaccgactt tgactcccaa atcaatgtgc cgaaaaccat ggaatctgga     120
acgttcatca ctgacaaaac tgtgctggac atgaaagcta ggattccaa gagcaatggg     180
gccattgcct ggagcaacca gacaagcttc acctgccaag atatcttcaa agagaccaac     240
```

```
gccacctacc ccagttcaga cgttccctgt gatgccacgt tgaccgagaa aagctttgaa      300
acagatatga acctaaactt tcaaaacctg tcagttatgg gactccgaat cctcctgctg      360
aaagtagcgg gatttaacct gctcatgacg ctgaggctgt ggtccagt                  408
```

<210> SEQ ID NO 59
<211> LENGTH: 522
<212> TYPE: DNA
<213> ORGANISM: Artificial Sequence
<220> FEATURE:
<223> OTHER INFORMATION: synthetic

<400> SEQUENCE: 59

```
gaggatctga gaaatgtgac tccacccaag gtctccttgt ttgagccatc aaaagcagag       60
attgcaaaca acaaaaggc taccctcgtg tgcttggcca ggggcttctt ccctgaccac      120
gtggagctga gctggtgggt gaatggcaag gaggtccaca gtggggtcag cacggaccct     180
caggcctaca aggagagcaa ttatagctac tgcctgagca gccgcctgag ggtctctgct     240
accttctggc acaatcctcg aaaccacttc cgctgccaag tgcagttcca tgggctttca     300
gaggaggaca gtggccaga gggctcaccc aaacctgtca cacagaacat cagtgcagag      360
gcctggggcc gagcagactg tggaatcact tcagcatcct atcatcaggg ggttctgtct     420
gcaaccatcc tctatgagat cctactgggg aaggccaccc tatatgctgt gctggtcagt     480
ggcctggtgc tgatggccat ggtcaagaaa aaaaattcct ga                       522
```

<210> SEQ ID NO 60
<211> LENGTH: 420
<212> TYPE: DNA
<213> ORGANISM: Artificial Sequence
<220> FEATURE:
<223> OTHER INFORMATION: synthetic

<400> SEQUENCE: 60

```
atccagaacc ccgaccccgc cgtgtaccag ctgcgggaca gcaagagcag cgacaagagc       60
gtgtgcctgt tcaccgactt cgacagccag accaacgtga gccagagcaa ggactccgac     120
gtgtacatca ccgacaagtg cgtgctggac atgcggagca tggacttcaa gagcaactcc     180
gccgtggcct ggtccaacaa gagcgacttc gcctgcgcca acgccttcaa caacagcatc     240
atccccgagg acaccttttt ccccagcccc gagagcagct cgacgtgaa actggtggag      300 aagagcttcg agaccgacac caacctgaac ttccagaacc tgagcgtgat cggcttcaga     360
atcctgctgc tgaaggtggc cggcttcaac ctgctgatga ccctgcggct gtggagcagc     420
```

<210> SEQ ID NO 61
<211> LENGTH: 540
<212> TYPE: DNA
<213> ORGANISM: Artificial Sequence
<220> FEATURE:
<223> OTHER INFORMATION: synthetic

<400> SEQUENCE: 61

```
gaggacctga agaacgtgtt ccccccccgag gtggccgtgt tcgagcccag cgaggccgag       60
atcagccaca cccagaaagc caccctggtc tgcctggcca ccggcttcta ccccgaccac     120
gtggagctgt cttggtgggt gaacggcaaa gaggtgcaca gcggcgtctg caccgacccc     180
cagccgctga agagcagcc cgccctgaac gacagccggt actgcctgag cagccggctg     240
agagtgagcg ccaccttctg gcagaacccc cggaaccact tccggtgcca ggtgcagttc     300
```

-continued

| | | | | |
|---|---|---|---|---|
| tacggcctga | gcgagaacga | cgagtggacc | caggacagag | ccaagccgt gacccagatc | 360 |
| gtgagcgccg | aggcctgggg | cagagccgac | tgcggcttca | ccagcgagag ctaccagcag | 420 |
| ggcgtgctgt | ccgccaccat | cctgtacgag | atcctgctgg | gcaaggccac actgtacgcc | 480 |
| gtgctggtgt | ccgccctggt | gctgatggct | atggtgaagc | ggaaggacag ccggggctga | 540 |